(12) United States Patent
Manwaring et al.

(10) Patent No.: US 8,372,066 B2
(45) Date of Patent: *Feb. 12, 2013

(54) INDUCTIVELY HEATED MULTI-MODE SURGICAL TOOL

(75) Inventors: Kim Manwaring, Phoenix, AZ (US); David McNally, Salt Lake City, UT (US)

(73) Assignee: Domain Surgical, Inc., Salt Lake City, UT (US)

( * ) Notice: Subject to any disclaimer, the term of this patent is extended or adjusted under 35 U.S.C. 154(b) by 260 days.

This patent is subject to a terminal disclaimer.

(21) Appl. No.: 12/647,329

(22) Filed: Dec. 24, 2009

(65) Prior Publication Data

US 2010/0268213 A1    Oct. 21, 2010

Related U.S. Application Data

(60) Provisional application No. 61/170,203, filed on Apr. 17, 2009, provisional application No. 61/170,220, filed on Apr. 17, 2009, provisional application No. 61/170,207, filed on Apr. 17, 2009.

(51) Int. Cl.
*A61B 18/04* (2006.01)
*A61B 7/00* (2006.01)

(52) U.S. Cl. .............. 606/31; 606/27; 606/28; 606/39; 606/40; 607/96

(58) Field of Classification Search ............. 606/47, 606/113; 607/103
See application file for complete search history.

(56) References Cited

U.S. PATENT DOCUMENTS

| | | |
|---|---|---|
| 300,155 A | 6/1884 | Starr |
| 770,368 A | 9/1904 | Heath |
| 1,104,053 A | 7/1914 | Lea |
| 1,280,052 A | 9/1918 | Lidberg |
| 1,335,987 A | 4/1920 | Reid |
| 1,366,231 A | 1/1921 | Winter et al. |
| 1,401,104 A | 12/1921 | Kruesheld |
| 1,794,296 A | 2/1931 | Hyams |
| 2,027,854 A | 1/1936 | Breth et al. |
| 2,050,904 A | 8/1936 | Trice |
| 2,250,602 A | 7/1941 | Pierce |
| 2,278,633 A | 4/1942 | Bagnall |
| 2,375,154 A | 5/1945 | Volterra |
| 2,412,977 A | 12/1946 | Eskin |
| 2,501,499 A | 3/1950 | Crowley |
| 2,670,425 A | 12/1954 | Stone |
| 2,735,797 A | 2/1956 | Schjeldahl |
| 2,782,290 A | 2/1957 | Lannan et al. |

(Continued)

FOREIGN PATENT DOCUMENTS

| | | |
|---|---|---|
| EP | 0 130 671 | 9/1985 |
| GB | 2 022 974 | 12/1978 |

(Continued)

OTHER PUBLICATIONS

Center for Research in Scientific Computation. *A Domain Wall Theory for Ferroelectric Hysteresis*, Jan. 1999.

(Continued)

*Primary Examiner* — Linda Dvorak
*Assistant Examiner* — Jaymi Della
(74) *Attorney, Agent, or Firm* — Bateman IP

(57) ABSTRACT

Thermal, electrosurgical and mechanical modalities may be combined in a surgical tool. Potentially damaging effects in a first modality may be minimized by using a secondary modality. In one example, thermal hemostasis may thus help electrosurgical applications avoid the adverse tissue effects associated with hemostatic monopolar electrosurgical waveforms while retaining the benefits of using monopolar incising waveforms.

35 Claims, 36 Drawing Sheets

U.S. PATENT DOCUMENTS

| | | | |
|---|---|---|---|
| 2,831,242 A | 4/1958 | Kieffer et al. | |
| 2,846,560 A | 8/1958 | Jacoby et al. | |
| 2,863,036 A | 12/1958 | Mitchell et al. | |
| 2,947,345 A | 8/1960 | Schjeldahl | |
| 2,960,592 A | 11/1960 | Pierce | |
| 3,084,242 A | 4/1963 | Vogler et al. | |
| 3,213,259 A | 10/1965 | Bennet et al. | |
| 3,350,544 A | 10/1967 | Lennox | |
| 3,352,011 A | 11/1967 | Alexander et al. | |
| 3,400,252 A | 9/1968 | Hayakawa | |
| 3,404,202 A | 10/1968 | Carlson et al. | |
| 3,413,442 A | 11/1968 | Buiting et al. | |
| 3,414,705 A | 12/1968 | Marcoux | |
| 3,434,476 A | 3/1969 | Shaw et al. | |
| 3,501,619 A | 3/1970 | Buiting et al. | |
| 3,520,043 A | 7/1970 | Darling | |
| 3,556,953 A | 1/1971 | Schulz | |
| 3,768,482 A | 10/1973 | Shaw | |
| 3,825,004 A | 7/1974 | Durden, III | |
| 3,834,392 A | 9/1974 | Lampman et al. | |
| 3,978,312 A | 8/1976 | Barton et al. | |
| RE29,088 E | 12/1976 | Shaw | |
| 4,089,336 A | 5/1978 | Cage et al. | |
| 4,091,813 A | 5/1978 | Shaw et al. | |
| RE30,190 E | 1/1980 | Shaw | |
| 4,185,632 A | 1/1980 | Shaw | |
| 4,196,734 A * | 4/1980 | Harris | 606/31 |
| 4,198,957 A | 4/1980 | Cage et al. | |
| 4,206,759 A | 6/1980 | Shaw | |
| 4,207,896 A | 6/1980 | Shaw | |
| 4,209,017 A | 6/1980 | Shaw | |
| 4,256,945 A | 3/1981 | Carter et al. | |
| 4,364,390 A | 12/1982 | Shaw | |
| 4,371,861 A | 2/1983 | Abdelrahman et al. | |
| 4,374,517 A | 2/1983 | Hagiwara | |
| RE31,723 E | 11/1984 | Shaw | |
| 4,481,057 A | 11/1984 | Beard | |
| 4,485,810 A | 12/1984 | Beard | |
| 4,492,231 A | 1/1985 | Auth | |
| 4,493,320 A | 1/1985 | Treat | |
| 4,523,084 A | 6/1985 | Tamura et al. | |
| 4,549,073 A | 10/1985 | Tamura et al. | |
| 4,600,018 A | 7/1986 | James et al. | |
| 4,622,966 A | 11/1986 | Beard | |
| 4,701,587 A | 10/1987 | Carter et al. | |
| 4,752,673 A | 6/1988 | Krumme | |
| 4,807,620 A | 2/1989 | Strul | |
| 4,839,501 A | 6/1989 | Cowell | |
| 4,848,337 A | 7/1989 | Shaw et al. | |
| 4,877,944 A | 10/1989 | Cowell et al. | |
| 4,914,267 A | 4/1990 | Derbyshire | |
| 4,938,761 A | 7/1990 | Ensslin | |
| 5,047,025 A | 9/1991 | Taylor et al. | |
| 5,053,595 A | 10/1991 | Derbyshire | |
| 5,057,106 A | 10/1991 | Kasevich et al. | |
| 5,071,419 A | 12/1991 | Rydell et al. | |
| 5,087,256 A | 2/1992 | Taylor et al. | |
| 5,087,804 A | 2/1992 | McGaffigan | |
| 5,098,429 A | 3/1992 | Sterzer | |
| 5,107,095 A | 4/1992 | Derbyshire | |
| 5,182,427 A | 1/1993 | McGaffigan | |
| 5,189,271 A | 2/1993 | Derbyshire | |
| 5,197,649 A | 3/1993 | Bessler et al. | |
| 5,203,782 A | 4/1993 | Gudov et al. | |
| 5,211,646 A | 5/1993 | Alperovich et al. | |
| 5,217,460 A | 6/1993 | Knoepfler | |
| 5,300,068 A | 4/1994 | Rosar et al. | |
| 5,300,750 A | 4/1994 | Carter, Jr. et al. | |
| 5,308,311 A | 5/1994 | Eggers et al. | |
| 5,318,564 A | 6/1994 | Eggers | |
| 5,376,094 A | 12/1994 | Kline | |
| 5,382,247 A | 1/1995 | Cimino et al. | |
| 5,411,508 A | 5/1995 | Bessler et al. | |
| 5,425,731 A | 6/1995 | Daniel et al. | |
| 5,445,635 A | 8/1995 | Denen et al. | |
| 5,472,443 A | 12/1995 | Cordis et al. | |
| 5,475,203 A | 12/1995 | McGaffigan | |
| 5,480,397 A | 1/1996 | Eggers | |
| 5,480,398 A | 1/1996 | Eggers | |
| 5,496,312 A * | 3/1996 | Klicek | 606/34 |
| 5,496,314 A | 3/1996 | Eggers | |
| 5,507,743 A * | 4/1996 | Edwards et al. | 606/41 |
| 5,540,679 A | 7/1996 | Fram et al. | |
| 5,540,681 A | 7/1996 | Strul et al. | |
| 5,542,916 A | 8/1996 | Hirsch et al. | |
| 5,571,153 A | 11/1996 | Wallsten | |
| 5,573,533 A | 11/1996 | Strul | |
| 5,593,406 A | 1/1997 | Eggers et al. | |
| 5,595,565 A | 1/1997 | Treat et al. | |
| 5,611,798 A | 3/1997 | Eggers | |
| 5,674,219 A | 10/1997 | Monson et al. | |
| 5,707,402 A | 1/1998 | Heim | |
| 5,807,392 A | 9/1998 | Eggers | |
| 5,836,874 A | 11/1998 | Swanson et al. | |
| 5,836,943 A | 11/1998 | Miller, III | |
| 5,911,719 A | 6/1999 | Eggers | |
| 5,964,759 A | 10/1999 | Yamanashi et al. | |
| 6,006,755 A | 12/1999 | Edwards | |
| 6,035,238 A | 3/2000 | Ingle et al. | |
| 6,066,138 A | 5/2000 | Sheffer et al. | |
| 6,161,048 A | 12/2000 | Sluijter et al. | |
| 6,228,084 B1 | 5/2001 | Kirwan, Jr. | |
| 6,241,723 B1 | 6/2001 | Heim et al. | |
| 6,287,305 B1 | 9/2001 | Heim et al. | |
| 6,358,273 B1 | 3/2002 | Strul et al. | |
| 6,533,781 B2 | 3/2003 | Heim et al. | |
| 6,602,252 B2 | 8/2003 | Mollenauer | |
| 6,604,003 B2 | 8/2003 | Fredricks et al. | |
| 6,626,901 B1 | 9/2003 | Treat et al. | |
| 6,632,182 B1 | 10/2003 | Treat | |
| 6,692,489 B1 | 2/2004 | Heim et al. | |
| 6,726,683 B1 | 4/2004 | Shaw | |
| 6,821,273 B2 | 11/2004 | Mollenauer | |
| 6,860,880 B2 | 3/2005 | Treat et al. | |
| 6,908,463 B2 | 6/2005 | Treat et al. | |
| 6,911,026 B1 | 6/2005 | Hall et al. | |
| 6,912,911 B2 | 7/2005 | Oh et al. | |
| 6,980,862 B2 | 12/2005 | Fredricks et al. | |
| 7,011,656 B2 | 3/2006 | McGaffigan | |
| 7,083,613 B2 | 8/2006 | Treat | |
| 7,122,030 B2 | 10/2006 | Flores et al. | |
| 7,164,968 B2 | 1/2007 | Treat et al. | |
| 7,175,621 B2 | 2/2007 | Heim et al. | |
| 7,211,079 B2 | 5/2007 | Treat | |
| 7,211,080 B2 | 5/2007 | Treat et al. | |
| 7,235,073 B2 | 6/2007 | Levine et al. | |
| 7,300,452 B2 | 11/2007 | Gleich | |
| 7,317,275 B2 | 1/2008 | Treat | |
| 7,326,202 B2 | 2/2008 | McGaffigan | |
| 7,329,255 B2 | 2/2008 | McGaffigan | |
| 7,377,919 B2 | 5/2008 | Heim et al. | |
| 7,396,356 B2 | 7/2008 | Mollenauer | |
| 7,473,250 B2 | 1/2009 | Makin et al. | |
| 7,494,492 B2 | 2/2009 | Da Silva et al. | |
| 7,528,663 B2 | 5/2009 | Naletov et al. | |
| 7,533,719 B2 | 5/2009 | Hinson et al. | |
| 7,540,324 B2 | 6/2009 | de Rouffignac | |
| 7,549,470 B2 | 6/2009 | Vinegar | |
| 7,556,095 B2 | 7/2009 | Vinegar | |
| 7,556,096 B2 | 7/2009 | Vinegar | |
| 7,559,367 B2 | 7/2009 | Vinegar | |
| 7,559,368 B2 | 7/2009 | Vinegar | |
| 7,562,706 B2 | 7/2009 | Li et al. | |
| 7,562,707 B2 | 7/2009 | Miller | |
| 7,578,815 B2 | 8/2009 | Howell | |
| 7,581,589 B2 | 9/2009 | Roes et al. | |
| 7,584,789 B2 | 9/2009 | Mo et al. | |
| 7,588,565 B2 | 9/2009 | Marchitto et al. | |
| 7,588,566 B2 | 9/2009 | Treat et al. | |
| 7,591,310 B2 | 9/2009 | Minderhoud | |
| 7,597,147 B2 | 10/2009 | Vitek | |
| 7,604,052 B2 | 10/2009 | Roes | |
| 7,610,962 B2 | 11/2009 | Fowler | |
| 7,613,523 B2 | 11/2009 | Eggers et al. | |
| 7,631,689 B2 | 12/2009 | Vinegar | |
| 7,631,690 B2 | 12/2009 | Vinegar | |
| 7,632,295 B2 | 12/2009 | Flores | |

| | | |
|---|---|---|
| 7,635,023 B2 | 12/2009 | Goldberg |
| 7,635,024 B2 | 12/2009 | Karanikas |
| 7,635,025 B2 | 12/2009 | Vinegar |
| 7,702,397 B2 | 4/2010 | Fredricks et al. |
| 7,871,406 B2 | 1/2011 | Nields et al. |
| 7,922,713 B2 | 4/2011 | Geisel |
| 7,938,779 B2 | 5/2011 | Sakurai et al. |
| 7,951,149 B2 | 5/2011 | Carlton |
| 8,100,896 B2 | 1/2012 | Podhajsky |
| 2001/0014804 A1* | 8/2001 | Goble et al. .................. 606/41 |
| 2002/0019644 A1 | 2/2002 | Hastings et al. |
| 2002/0173787 A1 | 11/2002 | Buysse et al. |
| 2003/0004507 A1 | 1/2003 | Francischelli et al. |
| 2003/0055417 A1 | 3/2003 | Truckai et al. |
| 2003/0055424 A1 | 3/2003 | Ciarrocca |
| 2003/0073987 A1 | 4/2003 | Sakurai et al. |
| 2003/0073989 A1 | 4/2003 | Hoey et al. |
| 2003/0144660 A1 | 7/2003 | Mollenauer |
| 2003/0171747 A1 | 9/2003 | Kanehira et al. |
| 2003/0199755 A1 | 10/2003 | Halperin |
| 2004/0006335 A1 | 1/2004 | Garrison |
| 2004/0030330 A1 | 2/2004 | Brassell et al. |
| 2004/0034349 A1 | 2/2004 | Kirwan, Jr. et al. |
| 2004/0049185 A1 | 3/2004 | Latterell et al. |
| 2004/0073256 A1 | 4/2004 | Marchitto |
| 2004/0167506 A1 | 8/2004 | Chen |
| 2004/0176756 A1 | 9/2004 | McGaffigan |
| 2005/0021016 A1 | 1/2005 | Malecki et al. |
| 2005/0072827 A1 | 4/2005 | Mollenauer |
| 2005/0107776 A1 | 5/2005 | Mcgaffigan et al. |
| 2005/0113824 A1 | 5/2005 | Sartor et al. |
| 2005/0273111 A1 | 12/2005 | Ferree et al. |
| 2005/0283067 A1 | 12/2005 | Sobe |
| 2005/0283149 A1 | 12/2005 | Thorne et al. |
| 2005/0288659 A1 | 12/2005 | Kimura et al. |
| 2006/0127706 A1 | 6/2006 | Goebel et al. |
| 2006/0161149 A1 | 7/2006 | Privitera et al. |
| 2006/0167450 A1 | 7/2006 | Johnson et al. |
| 2006/0212030 A1 | 9/2006 | McGaffigan |
| 2006/0212031 A1 | 9/2006 | McGaffigan et al. |
| 2006/0217706 A1 | 9/2006 | Lau et al. |
| 2006/0241587 A1 | 10/2006 | Heim et al. |
| 2006/0241588 A1 | 10/2006 | Heim et al. |
| 2006/0241589 A1 | 10/2006 | Heim et al. |
| 2006/0271037 A1 | 11/2006 | Maroney et al. |
| 2007/0005054 A1 | 1/2007 | Heim et al. |
| 2007/0005055 A1 | 1/2007 | Heim et al. |
| 2007/0005056 A1 | 1/2007 | Heim et al. |
| 2007/0005057 A1 | 1/2007 | Heim et al. |
| 2007/0005058 A1 | 1/2007 | Heim et al. |
| 2007/0005059 A1 | 1/2007 | Heim et al. |
| 2007/0005060 A1 | 1/2007 | Heim et al. |
| 2007/0060920 A1 | 3/2007 | Weitzner |
| 2007/0073282 A1 | 3/2007 | McGaffigan et al. |
| 2007/0100336 A1 | 5/2007 | McFarlin et al. |
| 2007/0106294 A1 | 5/2007 | Nesbitt |
| 2007/0127897 A1 | 6/2007 | John et al. |
| 2007/0131428 A1 | 6/2007 | Willem Cornelis den Boestert |
| 2007/0239151 A1 | 10/2007 | Atalar et al. |
| 2008/0017380 A1 | 1/2008 | Vinegar |
| 2008/0033419 A1 | 2/2008 | Nields et al. |
| 2008/0035346 A1 | 2/2008 | Nair et al. |
| 2008/0035347 A1 | 2/2008 | Brady |
| 2008/0035705 A1 | 2/2008 | Menotti |
| 2008/0038144 A1 | 2/2008 | Maziasz |
| 2008/0119841 A1 | 5/2008 | Geisel |
| 2008/0128134 A1 | 6/2008 | Mudunuri et al. |
| 2008/0135253 A1 | 6/2008 | Vinegar |
| 2008/0135254 A1 | 6/2008 | Vinegar |
| 2008/0142216 A1 | 6/2008 | Vinegar |
| 2008/0142217 A1 | 6/2008 | Pieterson |
| 2008/0173444 A1 | 7/2008 | Stone et al. |
| 2008/0174115 A1 | 7/2008 | Lambirth |
| 2008/0185147 A1 | 8/2008 | Vinegar |
| 2008/0217003 A1 | 9/2008 | Kuhlman |
| 2008/0217016 A1 | 9/2008 | Stegemeier |
| 2008/0236831 A1 | 10/2008 | Hsu |
| 2008/0277113 A1 | 11/2008 | Stegemeier |
| 2008/0281310 A1 | 11/2008 | Dunning et al. |
| 2009/0014180 A1 | 1/2009 | Stegemeier |
| 2009/0014181 A1 | 1/2009 | Vinegar |
| 2009/0112200 A1 | 4/2009 | Eggers |
| 2009/0118729 A1 | 5/2009 | Auth et al. |
| 2009/0118730 A1 | 5/2009 | Mollenauer |
| 2009/0198224 A1 | 8/2009 | Mcgaffigan |
| 2009/0248002 A1 | 10/2009 | Takashino et al. |
| 2009/0292347 A1 | 11/2009 | Asmus et al. |
| 2010/0152725 A1 | 6/2010 | Pearson et al. |
| 2010/0198216 A1 | 8/2010 | Palanker |
| 2010/0268205 A1 | 10/2010 | Manwaring |
| 2010/0268206 A1 | 10/2010 | Manwaring |
| 2010/0268207 A1 | 10/2010 | Manwaring |
| 2010/0268208 A1 | 10/2010 | Manwaring |
| 2010/0268209 A1 | 10/2010 | Manwaring |
| 2010/0268210 A1 | 10/2010 | Manwaring |
| 2010/0268211 A1 | 10/2010 | Manwaring |
| 2010/0268212 A1 | 10/2010 | Manwaring |
| 2010/0268213 A1 | 10/2010 | Manwaring |
| 2010/0268214 A1 | 10/2010 | Manwaring |
| 2010/0268215 A1 | 10/2010 | Manwaring |
| 2010/0268216 A1 | 10/2010 | Manwaring |

FOREIGN PATENT DOCUMENTS

| | | |
|---|---|---|
| GB | 1 546 624 | 5/1979 |
| RU | 2 072 118 | 1/1997 |
| WO | WO-82/00746 | 3/1982 |
| WO | WO 92/17121 | 10/1992 |
| WO | WO-93/21839 | 11/1993 |
| WO | WO-96/26677 | 11/1996 |
| WO | WO 9937227 A1 | 7/1999 |
| WO | WO-01/06943 | 2/2001 |
| WO | WO-2004/014217 | 2/2004 |
| WO | WO-2004/076146 | 9/2004 |
| WO | WO-2006/017517 | 2/2006 |
| WO | WO-2006/029649 | 3/2006 |
| WO | WO 2007080578 A2 | 7/2007 |
| WO | WO-2008/060668 | 5/2008 |

OTHER PUBLICATIONS

International Preliminary Report on Patentability from related PCT Patent Application No. PCT/US2010/031114, Nov. 1, 2011.
URSI EMTS 2004, pp. 489-491, *Electromagnetic Probes for Living Tissue Cauterization*.
Metcal Soldering Iron Catalog—2006.
International Preliminary Report from related PCT Patent Application No. PCT/US2010/031114, Apr. 14, 2010.
"High Temp Metals." NI2001201 Technical Data. High Temp Metals, Inc., n.d. Web. Jul. 13, 2012. <http://www.hightempmetals.com/techdatafnitempNi200data.php.

* cited by examiner

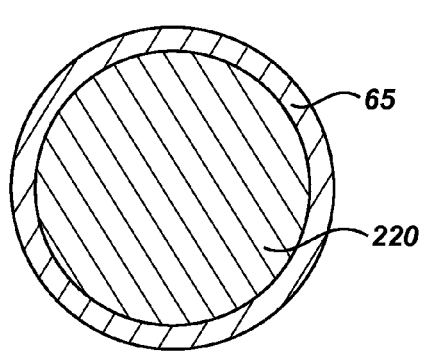
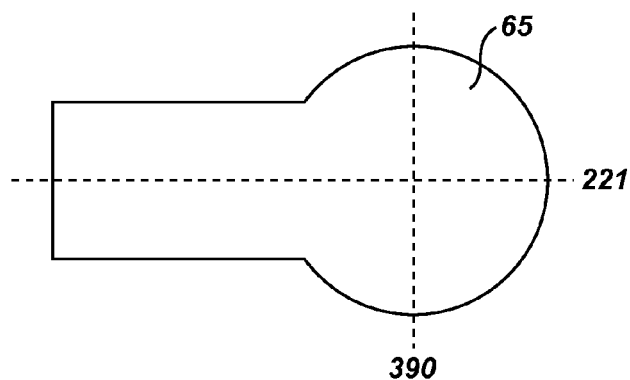
Fig. 13              Fig. 14A
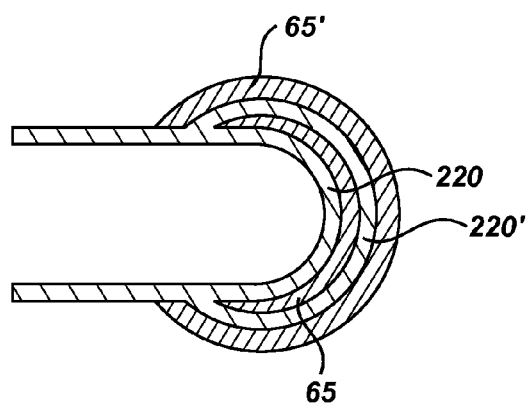
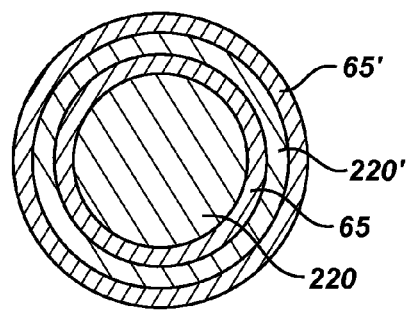
Fig. 14B            Fig. 15

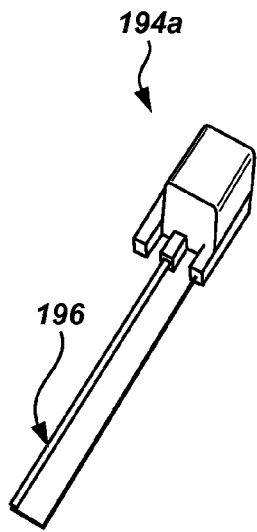 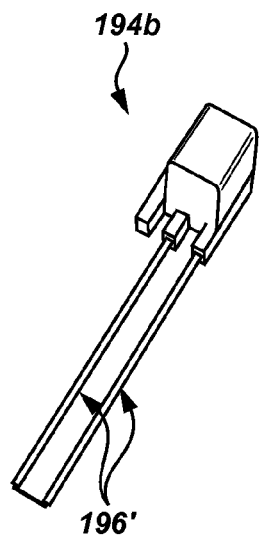 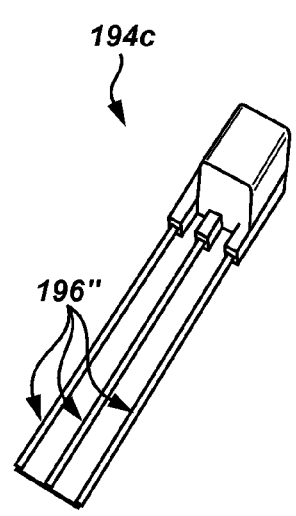
*Fig. 18A*    *Fig. 18B*    *Fig. 18C*
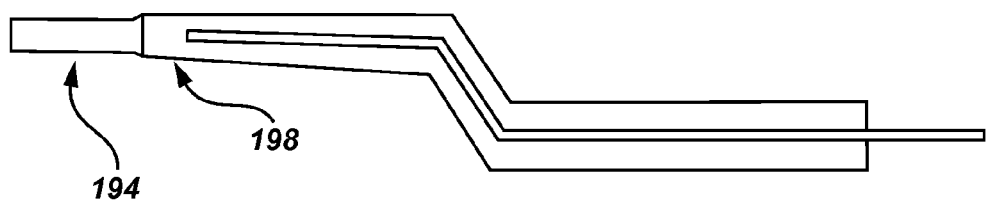
*Fig. 18D*

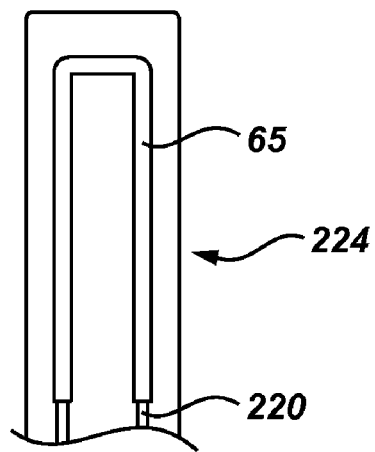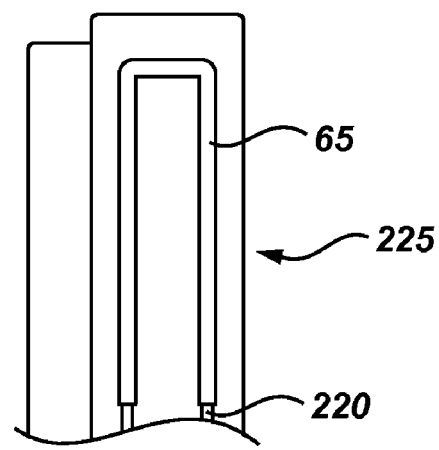
*Fig. 20A*      *Fig. 20B*
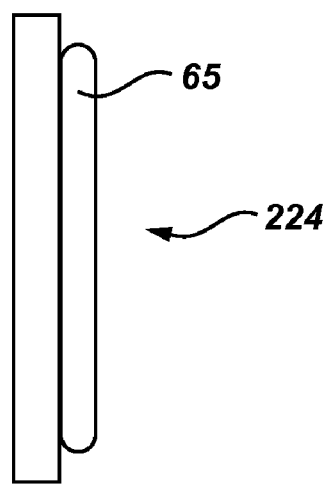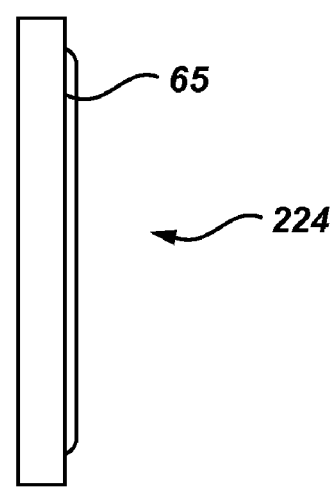
*Fig. 20C*      *Fig. 20D*

INDUCTIVELY HEATED MULTI-MODE SURGICAL TOOL

RELATED APPLICATIONS

The present application claims the benefit of U.S. Provisional Patent Application Ser. No. 61/170,203, filed Apr. 17, 2009, U.S. Provisional Patent Application Ser. No. 61/170,220, filed Apr. 17, 2009, and U.S. Provisional Patent Application Ser. No. 61/170,207, filed Apr. 17, 2009 which are incorporated hereby by references in their entirety.

This application is part of a group of similar applications including U.S. patent application Ser. No. 12/647,340, filed Dec. 24, 2009, U.S. patent application Ser. No. 12/647,344, filed Dec. 24, 2009, U.S. patent application Ser. No. 12/647,350, filed Dec. 24, 2009, U.S. patent application Ser. No. 12/647,355, filed Dec. 24, 2009, U.S. patent application Ser. No. 12/647,358, filed Dec. 24, 2009, U.S. patent application Ser. No. 12/647,363, filed Dec. 24, 2009, U.S. patent application Ser. No. 12/647,371, filed Dec. 24, 2009, U.S. patent application Ser. No. 12/647,302, filed Dec. 24, 2009, U.S. patent application Ser. No. 12/647,374, filed Dec. 24, 2009, U.S. patent application Ser. No. 12/647,376, filed Dec. 24, 2009, and U.S. patent application Ser. No. 12/647,380, filed Dec. 24, 2009, each of which is incorporated hereby by references in its entirety.

BACKGROUND OF THE INVENTION

1. The Field of the Invention

The present invention relates to surgical tools. More specifically, the present invention relates to thermally adjustable tools used in open and minimally invasive surgical procedures and interventional surgical and therapeutic procedures.

2. State of the Art

Surgery generally involves cutting, repairing and/or removing tissue or other materials. These applications are generally performed by cutting tissue, fusing tissue, or tissue destruction.

Current electrosurgery modalities used for cutting, coagulating, desiccating, ablating, or fulgurating tissue, have undesirable side effects and drawbacks.

Monopolar and bipolar electrosurgery modalities generally have disadvantages relating to "beyond the tip" effects. These effects are caused by passing alternating current through tissues in contact with conducting instruments or probes. One effect that is believed to be caused by both modalities is electrical muscle stimulation, which may interrupt surgical procedures and require administration of muscle relaxants.

Monopolar surgical instruments require electric current to pass through the patient. A return electrode is placed on the patient, often on the patient's thigh. Electricity is conducted from a "knife" electrode through the tissue and returns through the return electrode. Other forms of monopolar instruments exist, such as those which use the capacitive effect of the body to act as the return electrode or ground.

A low voltage high frequency waveform will incise, but has little hemostatic effect. A high voltage waveform will cause adjacent tissue hemostasis and coagulation. Therefore, when hemostasis is desirable, high voltage is used. The high voltage spark frequently has deeper tissue effects than the cut because the electricity must pass through the patient. The damage to the tissue extends away from the actual point of coagulation. Furthermore, there are complaints of return electrode burns. Yet, any reduction of voltage reduces the effectiveness of hemostasis. Further, the temperature of the spark or arc cannot be precisely controlled, which can lead to undesirable charring of target tissue.

Bipolar surgical instruments can produce tissue damage and problems similar to monopolar devices, such as sparking, charring, deeper tissue effects and electric current damage away from the application of energy with varying effects due to the differing electrical conductivity of tissue types, such as nerve, muscle, fat and bone, and into adjacent tissues of the patient. However, the current is more, but not completely, contained between the bipolar electrodes. These electrodes are also generally more expensive because there are at least two precision electrodes that must be fabricated instead of the one monopolar electrode.

Electrocautery resistive heating elements reduce the drawbacks associated with charring and deeper tissue damage caused by other electrosurgery methods. However, such devices often present other tradeoffs, such as the latency in controlling heating and cooling time, and effective power delivery. Many resistive heating elements have slow heating and cooling times, which makes it difficult for the surgeon to work through or around tissue without causing incidental damage.

Tissue destruction instruments generally heat tissue to a predetermined temperature for a period of time to kill, or ablate, the tissue. In some controlled heating of tissues, a laser is directed to an absorptive cap to reach and maintain a predetermined temperature for a predetermined amount of time. While this provides the benefits of thermal heating, it is expensive due to the complexity and expense of laser hardware.

In another tissue destruction procedure, a microwave antenna array is inserted into the tissue. These arrays are powered by instruments that cause microwave energy to enter and heat the tissue. While such devices are often effective at killing, or ablating, the desired tissue, they often cause deeper tissue effects than the desired area. Additionally the procedures can require expensive equipment.

Tissue destruction with resistively heated tools can produce unintended collateral tissue damage, in addition to having slow heating and cooling attributes.

Use of ferrite beads and alloy mixes in ceramics have been examined as alternatives. When excited by the magnetic field associated with high frequency current passing through a conductor, ferrite beads and alloy mixes in ceramics can reach high temperatures very quickly. However, one major problem with the use of these materials is that a large temperature differential can cause the material to fracture, especially when it comes into and out of contact with liquids. In other words, if a hot ferrite surgical instrument is quenched by a cooler pool of liquid, such as blood or other body fluids, the material's corresponding temperature drops rapidly and may cause the material to fracture. These fractures not only cause the tool to lose its effectiveness as a heat source, because the magnetic field is disrupted, but may require extraction of the material from the patient. Obviously, the need to extract small pieces of ferrite product from a patient is highly undesirable. Thus, there is a need for an improved thermal surgical tool.

SUMMARY OF THE INVENTION

It is an object of the present invention to provide an improved thermally adjustable surgical or therapeutic tool.

According to one aspect of the invention, a thermal surgical tool system is provided with a ferromagnetic coating over a conductor and an oscillating electrical energy source for generating heat at the location of the coating while generating an additional tissue effect through the use of a second energy mode. The oscillating electrical energy may cause inductive heating of the ferromagnetic coating (the inductive thermal mode). Moreover, the surgeon may be able to quickly turn the inductive thermal mode of the surgical or therapeutic tool on and off due to a small heat latency. This may provide the advantage of allowing the surgeon to only deliver a thermal effect at desired locations, which may also prevent the accidental delivery of undesired thermal effects while waiting for the tool to cool. At the same time, a similar or different tissue effect may be delivered simultaneously or in succession by the second mode. If similar, the use of both modes may cause an increase in efficiency. If different, the modes may complement each other such that drawbacks of a single mode may be reduced.

According to another aspect of the invention, a thermal surgical tool system may be configured so that the inductive thermal mode and/or a second mode may be altered by the surgeon in near real-time to achieve different tissue effects, including hemostasis, tissue welding and tissue destruction.

According to another aspect of the invention, controlled thermal tissue destruction may be performed by using the benefits of an inductive thermal mode combined with a second mode. The ferromagnetic coated conductor can be used as part of a cutting, lesioning or ablating probe with the ferromagnetic coating providing thermal heating, as well as a conductive path for monopolar electrosurgical energy to pass in the tissue.

According to another aspect of the invention, the second mode may include a monopolar or bipolar RF element, such as a monopolar or bipolar RF electrosurgical instrument, which may be used to cut and coagulate tissue. While RF electrosurgical instruments are highly effective, they tend to create tissue damage beyond the incision when used for sealing. Thus, an RF monopolar or bipolar electrosurgical instrument can be used in conjunction with a ferromagnetic coated conductor which seals the tissue being cut with the RF instrument.

In accordance with yet another aspect of the present invention, the multi-mode surgical tool may include a thermal and ultrasonic tool for cutting and/or treating tissue.

These and other aspects of the present invention are realized in a thermally adjustable surgical tool as shown and described in the following figures and related description.

BRIEF DESCRIPTION OF THE DRAWINGS

Various embodiments of the present invention are shown and described in reference to the numbered drawings wherein:

FIG. 13 shows an axial cross-sectional view of a single layer ferromagnetic coated conductor surgical tool in the ferromagnetic-coated region;

FIG. 14A shows a perspective view of a multi-layer ferromagnetic coated conductor surgical tool tip;

FIG. 14B shows a side cross-sectional view of a multi-layer ferromagnetic coated conductor surgical tool tip shown in 14A;

FIG. 15 shows an axial cross-section of the multi-layer ferromagnetic coated conductor surgical tool tip shown in FIG. 14A;

FIG. 18A shows a single edge ferromagnetic coated conductor surgical tip in accordance with one aspect of the invention;

FIG. 18B shows a double edge ferromagnetic coated conductor surgical tip;

FIG. 18C shows a three wire ferromagnetic coated conductor surgical tip;

FIG. 18D shows a receptacle for the tips shown in FIGS. 18A through 18C;

FIG. 20A shows a thermal surgical tool with a spatula shaped geometry;

FIG. 20B shows a thermal surgical tool with a spatula shaped geometry in a forceps configuration;

FIG. 20C shows a top view of the thermal surgical tool of FIG. 20A with the ferromagnetic coated conductor upon the primary geometry;

FIG. 20D shows a top view of the thermal surgical tool of FIG. 20A with the ferromagnetic coated conductor embedded within the primary geometry;

It will be appreciated that the drawings are illustrative and not limiting of the scope of the invention which is defined by the appended claims. The embodiments shown accomplish various aspects and objects of the invention. It is appreciated that it is not possible to clearly show each element and aspect of the invention in a single figure, and as such, multiple figures are presented to separately illustrate the various details of the invention in greater clarity. Similarly, not every embodiment need accomplish all advantages of the present invention.

DETAILED DESCRIPTION

The invention and accompanying drawings will now be discussed in reference to the numerals provided therein so as to enable one skilled in the art to practice the present invention. The drawings and descriptions are exemplary of various aspects of the invention and are not intended to narrow the scope of the appended claims.

As used herein, the term "ferromagnetic," "ferromagnet," and "ferromagnetism" refers to any ferromagnetic-like material that is capable of producing heat via magnetic induction, including but not limited to ferromagnets and ferrimagnets.

Figure 1:
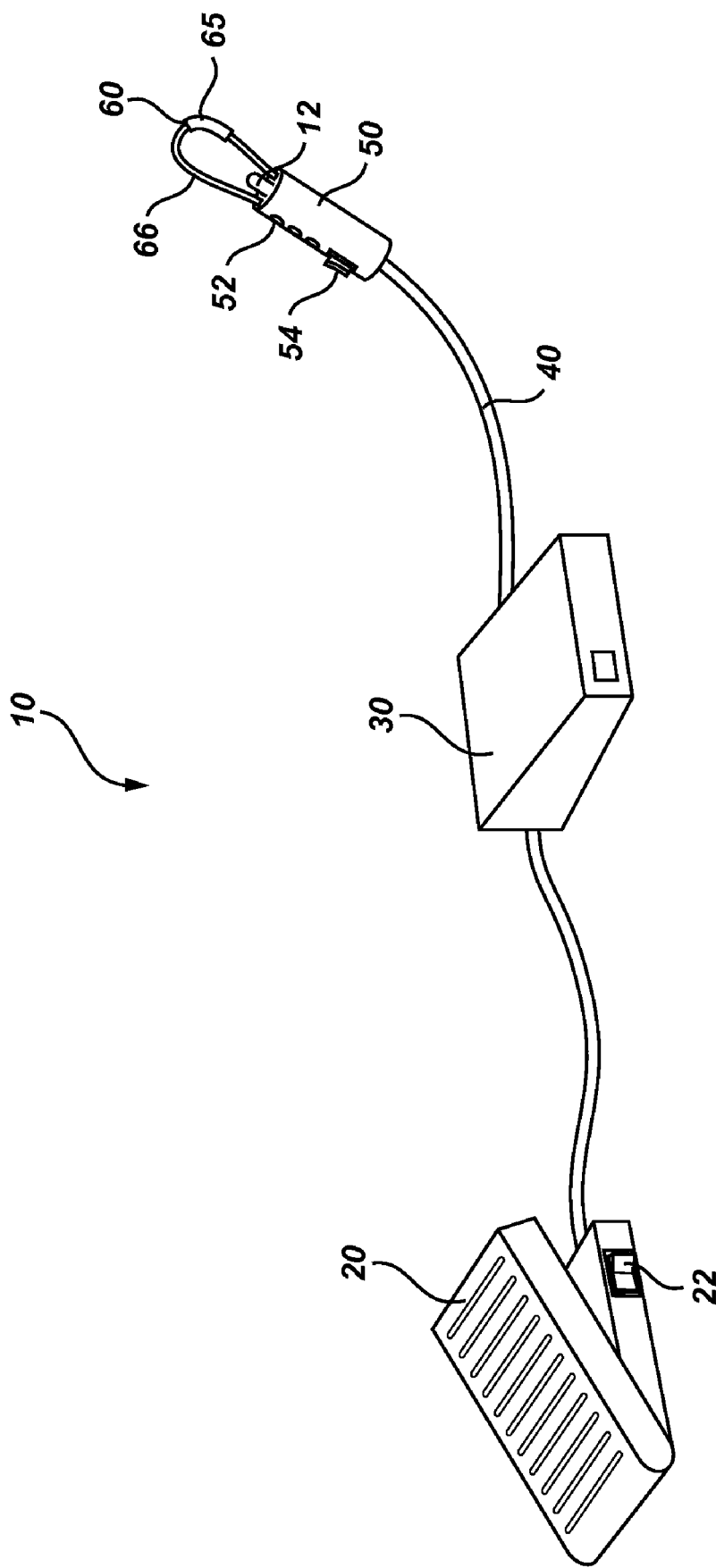
FIG. 1 shows a perspective view of a thermal surgical tool system in accordance with the principles of the present invention.

Turning now to FIG. 1, there is shown a perspective view of a thermal surgical tool system, generally indicated at 10. As will be discussed in additional detail below, the thermal tool system preferably uses a ferromagnetic coated conductor to treat or destroy tissue (i.e. endothelial tissue welding, homeostasis, ablation, etc).

It will be appreciated that the thermal surgical tool uses heat to incise tissue and does not cut tissue in the sense of a sharp edge being drawn across the tissue as with a conventional scalpel. While the embodiments of the present invention could be made with a relatively sharp edge so as to form a cutting blade, such is not necessary as the heated coating discussed herein will separate tissue without the need for a cutting blade or sharp edge. However, for convenience, the term cutting is used when discussing separating tissue.

In the embodiment shown as thermal surgical tool system 10, a control mechanism, such as a foot pedal 20 is used to control output energy produced by a power subsystem 30. The energy from the power subsystem 30 may be sent via radio frequency (RF) or oscillating electrical energy along a cable 40 to a handheld surgical tool 50, which contains a conductor 60 having a section thereof circumferentially coated with a ferromagnetic coating 65. The ferromagnetic coating 65 may transfer the electrical energy into available thermal energy via induction and corresponding hysteresis losses in the ferromagnetic material disposed around a conductor wire 66. (While conductor wire is used for ease of reference, it will be appreciated that the conductor material need not be a wire and those skilled in the art will be familiar with multiple conductors which will work in light of the disclosure of the present invention).

Application of a magnetic field (or magnetizing) to the ferromagnetic coating may produce an open loop B-H curve (also known as an open hysteresis loop), resulting in hysteresis losses and the resultant thermal energy. Electrodeposited films, such as a nickel-iron coating like PERMALLOY™, may form an array of randomly aligned microcrystals, resulting in randomly aligned domains, which together may have an open loop hysteresis curve when a high frequency current is passed through the conductor.

The RF energy may travel along the conductor's surface in a manner known as the "skin effect". The alternating RF current in the conductor's surface produces an alternating magnetic field, which may excite the domains in the ferromagnetic coating 65. As the domains realign with each oscillation of the current, hysteresis losses in the coating may cause inductive heating.

The RF conductor from the signal source up to and including the tip, may form a resonant circuit at a specific frequency (also known as a tuned circuit). Changes in the tip "detune" the circuit. Thus, should the ferromagnetic coating 65 or the conductor wire 66 become damaged, the circuit may likely become detuned. This detuning should reduce the efficiency of the heating of the ferromagnetic coating 65 such that the temperature will be substantially reduced. The reduced temperature should ensure little or no tissue damage after breakage.

It should be understood that the handheld surgical tool 50 may include indicia of the power being applied and may even include a mechanism for controlling the power. Thus, for example, a series of lights 52 could be used to indicate power level, or the handheld surgical tool 50 could include a switch, rotary dial, set of buttons, touchpad or slide 54 that communicates with the power source 30 to regulate power and thereby affect the temperature at the ferromagnetic coating 65 to having varying effects on tissue. While the controls are shown on the foot pedal 20 or the handheld surgical tool 50, they may also be included in the power subsystem 30 or even a separate control instrument. Safety features such as a button or touchpad that must be contacted to power the handheld surgical tool 50 may be employed, and may include a dead man's switch.

While the ferromagnetic coating 65 heats through induction, it also provides a temperature cap due to its Curie temperature. A Curie temperature is the temperature at which the material becomes paramagnetic, such that the alignment of each domain relative to the magnetic field decreases to such an extent that the magnetic properties of the coating are lost. When the material becomes paramagnetic, the heating caused by induction may be significantly reduced or even cease. This causes the temperature of the ferromagnetic material to stabilize around the Curie temperature if sufficient power is provided to reach the Curie temperature. Once the temperature has dropped below the Curie temperature, induction may again start causing heating of the material up to the Curie temperature. Thus, the temperature in the ferromagnetic coating may reach the Curie temperature during inductive heating with the application of sufficient power, but will not likely exceed the Curie temperature.

The thermal surgical tool system 10 allows the power output to be adjustable in order to adjust the temperature of the tool and its effect on tissue. This adjustability gives the surgeon precise control over the effects that may be achieved by the handheld surgical tool 50. Tissue effects such as cutting, hemostasis, tissue welding, tissue vaporization and tissue carbonization occur at different temperatures. By using the foot pedal 20 (or some other user control) to adjust the power output, the surgeon (or other physician, etc.) can adjust the power delivered to the ferromagnetic coating 65 and consequently control the tissue effects to achieve a desired result.

Thermal power delivery can be controlled by varying the amplitude, frequency or duty cycle of the alternating current waveform, or alteration of the circuit to affect the standing wave driving the ferromagnetic coated conductor, which may be achieved by input received by the foot pedal 20, the power subsystem 30, or the controls on the handheld surgical tool 50.

One additional advantage achieved by the inductive heating is that the ferromagnetic material can be heated to a cutting temperature in a small fraction of a second (typically as short as one quarter of a second). Additionally, because of the relatively low mass of the coating, the small thermal mass of the conductor, and the localization of the heating to a small region due to construction of the handheld surgical tool 50, the material will also cool extremely rapidly (i.e. approximately one half of a second). This provides a surgeon with a precise thermal tool while reducing accidental tissue damage caused by touching tissue when the thermal tool is not activated.

It will be appreciated that the time period required to heat and cool the handheld surgical tool 50 will depend, in part, on the relative dimensions of the conductor 60 and the ferromagnetic coating 65 and the heat capacity of the structure of the surgical tool. For example, the above time periods for heating and cooling of the handheld surgical tool 50 can be achieved with a tungsten conductor having a diameter of about 0.375 mm and a ferromagnetic coating of a Nickel Iron alloy (such as NIRON™ available from Enthone, Inc. of West Haven, Conn.) about the tungsten conductor about 0.0375 mm thick and two centimeters long.

One advantage of the present invention is that a sharp edge is not needed. When power is not being supplied to the surgical tool, the tool will not inadvertently cut tissue of the patient or of the surgeon if it is dropped or mishandled. If power is not being supplied to the conductor wire 66 and coating 65, the "cutting" portion of the tool may be touched without risk of injury. This is in sharp contrast to a cutting blade which may injure the patient or the surgeon if mishandled.

Other additions may also be placed on the handpiece in various locations. This may include a sensor stem 12 including a sensor to report temperature or a light to illuminate the surgical area.

Figure 2:
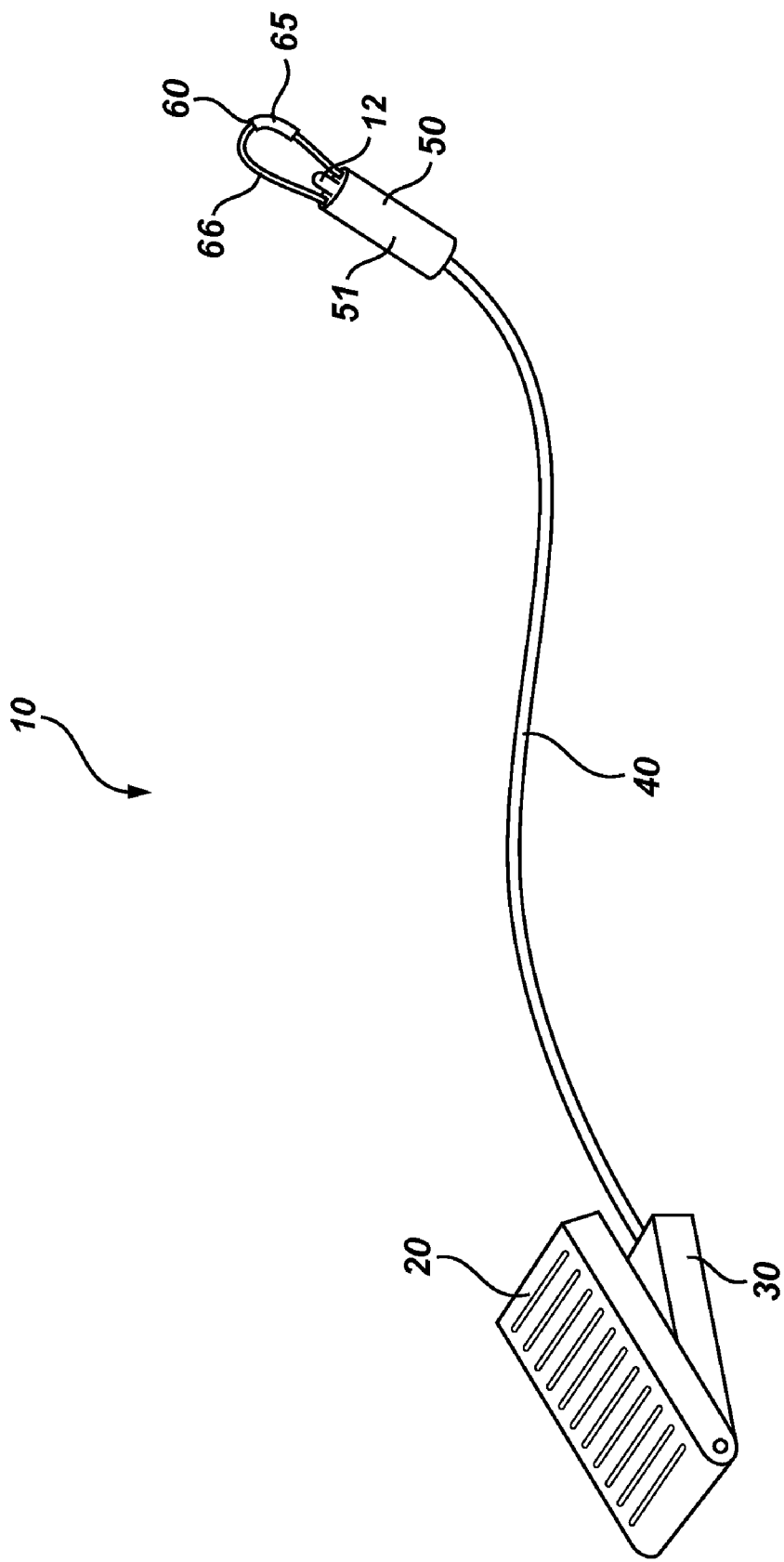
FIG. 2 shows a perspective view of an alternate embodiment of a thermal surgical tool system in accordance with the present invention.

Turning now to FIG. 2, a perspective view of an alternate embodiment of a thermal surgical system 10 is shown. In FIG. 2, the power source 30 is contained within the foot pedal 20. Depending on the application and power required, the instrument may even be entirely battery powered for relatively low power applications. An alternate embodiment for low power requirements may include the battery, power adjustment and power delivery, all self-contained in the handle 51 of the handheld surgical tool 50. Furthermore, a wireless communication module can be employed to send and receive information from the handheld surgical tool 50, including status and control settings that would enable users to monitor system performance and alter power settings remotely from the handheld surgical tool 50 itself.

It is our understanding that this thermal solution may provide advantages over monopolar and bipolar electrical systems currently available because the thermal damage may remain very close to the ferromagnetic surface of the coated region, whereas monopolar and bipolar electrical tissue ablation may frequently cause tissue damage for a distance away from the point of contact. It is our understanding that this method may also overcome disadvantages of other thermal devices based upon resistive heating, which may require more time to heat and cool, and thus present greater patient risk, while potentially having higher voltage requirements at the point of heating.

Furthermore, the thin ferromagnetic coating 65, disposed along a small segment of the conductor, may reduce the heating of other non-target material in the body, such as blood when working within the heart in atrial ablation—which can lead to complications if a clot is formed. The small thermal mass of the conductor wire 66, and localization of the heating to a small region provided by the construction of the tool (i.e. ferromagnetic coating 65 and adjacent structures) provides a reduced thermal path for heat transfer in directions away from the location of the ferromagnetic coating 65. This reduced thermal path may result in the precise application of heat at only the point desired. As this technology alone does not employ a spark or an arc like monopolar or bipolar technology, risks of ignition, such as by anesthetic gasses within or around the patient by sparks, are also reduced.

The thermal surgical tool system 10 may be used for a variety of therapeutic means—including sealing, "cutting" or separating tissue, coagulation, or vaporization of tissue. In one configuration, the thermal surgical tool system 10 may be used like a knife or sealer, wherein the surgeon is actively "cutting" or sealing tissue by movement of the ferromagnetic coating 65 through tissue. The thermal action of the embodiments disclosed here may have distinct advantages including substantial reduction, if not elimination, of deep tissue effects compared with those associated with monopolar and bipolar RF energy devices.

In another configuration, the ferromagnetic coated conductor 60 may be inserted into a lesion and set to a specific power delivery or variable power delivery based on monitored temperature. The thermal effects on the lesion and surrounding tissue may be monitored until the desired thermal effect is achieved or undesired effects are noticed. One advantage of the application of the ferromagnetic coated conductor is that it may be cost-effective compared to microwave or thermal laser modalities and avoids the undesired tissue effects of microwave lesion destruction. Thus, for example, a surgeon can insert the ferromagnetic coated conductor into a tumor or other tissue to be destroyed and precisely control the tissue damage that is created by activating the handheld surgical tool 50.

Sensors may be used to monitor conditions of the handheld surgical tool 50 or the tissue, such as an infrared detector or sensor stem 12. For instance, the temperature of the device or tissue may be important in performing a procedure. A sensor in the form of a thermocouple, a junction of dissimilar metals, thermistor or other temperature sensor may detect the temperature at or near the ferromagnetic coating 65 or tissue. The sensor may be part of the device, such as a thermocouple placed as a part of the conductor or near the ferromagnetic coating, or separate from the handheld surgical tool 50, such as a separate tip placed near the tissue or ferromagnetic coating 65. The temperatures may also be correlated with tissue effects, seen in FIG. 27. Other useful conditions to monitor may include, but are not limited to, color, spectral absorption, spectral reflection, temperature range, water content, proximity, tissue type, transferred heat, tissue status, impedance, resistance, voltage and visual feedback (i.e. a camera, fiberoptic or other visualization device).

The handheld surgical tool 50 may be configured for repeat sterilization or single patient uses. More complex devices may be useful for repeat sterilization, while more simple devices may be more useful for single patient use.

A method for treating or cutting tissue may include the steps of: selecting a surgical tool having a cutting edge and a conductor disposed adjacent the cutting edge, at least a portion of which is coated with a ferromagnetic material; cutting tissue with the cutting edge; and applying oscillating electrical energy to the conductor to heat the ferromagnetic material and thereby treating the cut tissue.

Optional steps of the method may include the steps of: causing hemostasis within the cut tissue; using the heated ferromagnetic material to incise tissue; or using the heated ferromagnetic material to cause vascular endothelial welding.

Figure 3:
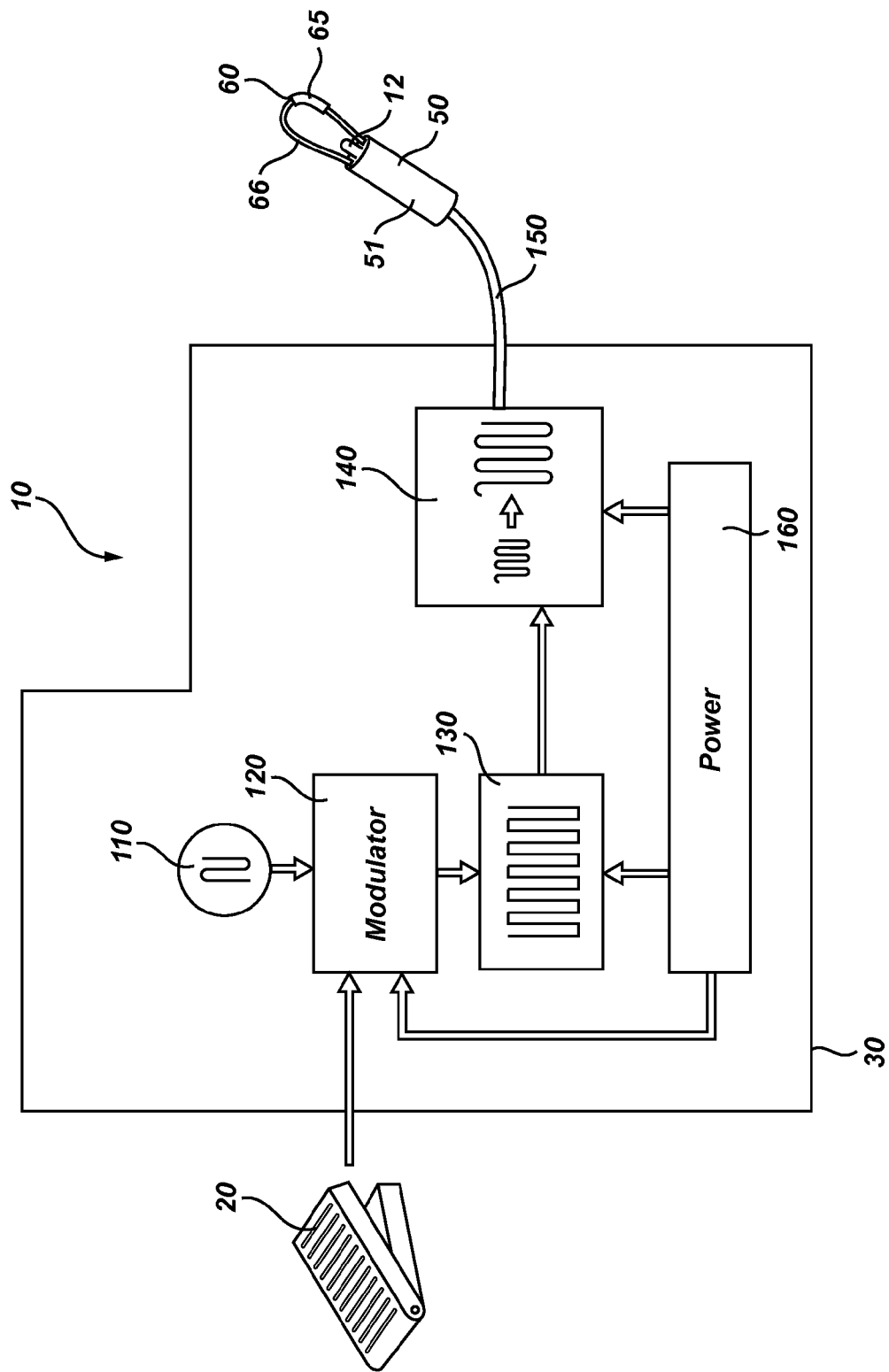
FIG. 3 shows a diagram of a thermal surgical tool system in accordance with the principles of the present invention.

Referring now to FIG. 3, a diagram of an embodiment of the adjustable thermal surgical tool system 10 is shown. The power delivery to the ferromagnetic coating 65 is controlled by a modulated high frequency waveform. The modulated waveform allows power delivery to be controlled in a manner that adjustably modifies, allows or blocks portions of the waveform based on the desired power delivery.

In FIG. 3, an initial waveform 110 is passed through a modulator 120 receiving commands from a foot pedal 20. The waveform is created by an oscillator 130 to the desired frequency, and modulated by the modulator 120, which may include, but is not limited to, one or more of amplitude, frequency or duty cycle modulation, including a combination thereof. The resultant signal is then amplified by an amplifier 140. The amplified signal is sent across a tuned cable 150, meaning that the cable is tuned to provide a standing wave with maximum current and minimum voltage at the location of the ferromagnetic coating 65 of the handheld surgical tool 50. Alternatively, the cable 150 may not be tuned, but a circuit may be placed in the handle 51 to impedance match the ferromagnetic coated conductor 60 as a load to the power source 30.

The thermal surgical tool system 10 may be tuned by specifying the location of the ferromagnetic coating 65 with respect to the amplifier 140 (such as cable length) and tuning the high frequency signal to approximately a resonant standing wave such that current is maximized at the location of the ferromagnetic coating 65.

It should be recognized that the surgical tool may operate in a dynamic environment. Thus when used herein, approximately a standing wave means that a circuit may be tuned such that the signal may be near an optimal standing wave but may not achieve it, may only achieve the wave for small amounts of time, or may successfully achieve a standing wave for longer periods of time. Similarly, any use of "standing wave" without the modifier of approximate should be understood to be approximate in the context of the thermal surgical tool.

One method for achieving such current maximization is to connect the ferromagnetic coated conductor 60 to a cable 150 that is an odd multiple of one-quarter wavelengths in length and connected to the output of the amplifier 140. The design of the circuit having a resonant standing wave is intended to optimize power delivery to the ferromagnetic coating. However, in one embodiment, the power source 30 could be positioned at the location of (or closely adjacent to) the ferromagnetic coating 65, and tuning could be achieved with electrical components, all within a single handheld, battery-powered instrument. Alternatively, electrical components necessary for impedance matching can be located at the output stage of the amplifier 140. Further, electrical components, such as a capacitor or inductor, can be connected in parallel or series to the ferromagnetic coated conductor 60 at the location of the connection of the conductor wire 66 to the cable 150, in order to complete a resonant circuit.

Dynamic load issues can be caused by the interaction of the ferromagnetic coated conductor 60 with various tissues. These issues may be minimized by the standing current wave being maximized at the load location. Multiple different frequencies can be used, including frequencies from 5 megahertz to 24 gigahertz, preferably between 40 MHz and 928 MHz. In some regulated countries it may be preferable choose frequencies in the ISM bands such as bands with the center frequencies of 6.78 MHz, 13.56 MHz, 27.12 MHz, 40.68 MHz, 433.92 MHz, 915 MHz, 2.45 GHz, 5.80 GHz, 24.125 GHz, 61.25 GHz, 122.5 GHz, 245 GHz. In one embodiment, the oscillator 130 uses an ISM Band frequency of 40.68 MHz, a class E amplifier 140, and a length of coaxial cable 150, all of which may be optimized for power delivery to a ferromagnetic coated tungsten conductor 60 with a ferromagnetic coating 65 consisting of a thickness of between 0.05 micrometer and 500 micrometers, and preferably between 1 micrometer and 50 micrometers. A useful estimate may be to start the ferromagnetic coating thickness at 10% of the conductor diameter, and up to 5 cm long. However, the ferromagnetic coating may be disposed as far along the length or along multiple regions of the conductor as where heating may be desired. (The ferromagnetic coating 65 may be formed from a Nickel Iron (NiFe) alloy, such as NIRON™ from Enthone, Inc. of West Haven, Conn., or other ferromagnetic coatings, including Co, Fe, $FeOFe_2O_3$, $NiOFe_2O_3$, $CuOFe_2O_3$, $MgOFe_2O_3$, MnBi, Ni, MnSb, $MnOFe_2O_3$, $Y_3Fe_5O_{12}$, $CrO_2$, MnAs, Gd, Dy, EuO, magnetite, yttrium iron garnet, aluminum, PERMALLOY™, and zinc.)

The size of the conductor, size of the ferromagnetic coating, associated thicknesses, shape, primary geometry, composition, power supply and other attributes may be selected based on the type of procedure and surgeon preferences. For example, a brain surgeon may desire a small instrument in light handheld package designed for quick application within the brain, while an orthopedic surgeon may require a larger device with more available power for operation on muscle.

The conductor may be formed from copper, tungsten, titanium, stainless steel, platinum and other materials that may conduct electricity. Considerations for the conductor may include, but are not limited to mechanical strength, thermal expansion, thermal conductivity, electrical conduction/resistivity, rigidity, and flexibility. It may be desirable to form the conductor wire 66 of more than one material. Connection of two dissimilar metals may form a thermocouple. If the thermocouple were placed in the vicinity of or within the ferromagnetic coating, the thermocouple provides a temperature feedback mechanism for the device. Further, some conductors may have a resistivity that correlates to temperature, which may also be used to measure temperature.

The tuning of the power source 30 also reduces the amount of high frequency energy radiating into the patient to near zero, as voltage is low, and ideally zero, at the location of the ferromagnetic coating 65. This is in contrast to monopolar devices, which require a grounding pad to be applied to the patient, or bipolar devices, both of which pass current through the tissue itself. The disadvantages of these effects are well known in the literature.

In many of these embodiments discussed herein, the combination of cable length, frequency, capacitance and inductance may also be used to adjust efficiency and tool geometry by tuning the power source 30 to deliver maximum power to the ferromagnetic coating 65, and therefore, maximum heat to the tissue. A tuned system also provides for inherent safety benefits; if the conductor were to be damaged, the system would become detuned, causing the power delivery efficiency to drop, and may even shut down if monitored by an appropriate safety circuit.

The amount of power delivered to the patient tissue may be modified by several means to provide precise control of tissue effects. The power source 30 may incorporate a modulator 120 for power delivery as described above. Another embodiment uses modification of the magnetic field by altering the geometry of the conductor wire 66 and the ferromagnetic coating 65 through which it passes, such as would be caused by a magnet. Placement of the magnet nearby the ferromagnetic coating 65 would similarly alter the induction effect and thereby change the thermal effect.

While modulation has been discussed as a method to control power delivery, other methods may be used to control power delivery. In one embodiment, the output power, and correspondingly the temperature, of the tool is controlled by tuning or detuning the drive circuit, including the conductor wire 66 and ferromagnetic coated conductor 60.

Figure 4A:
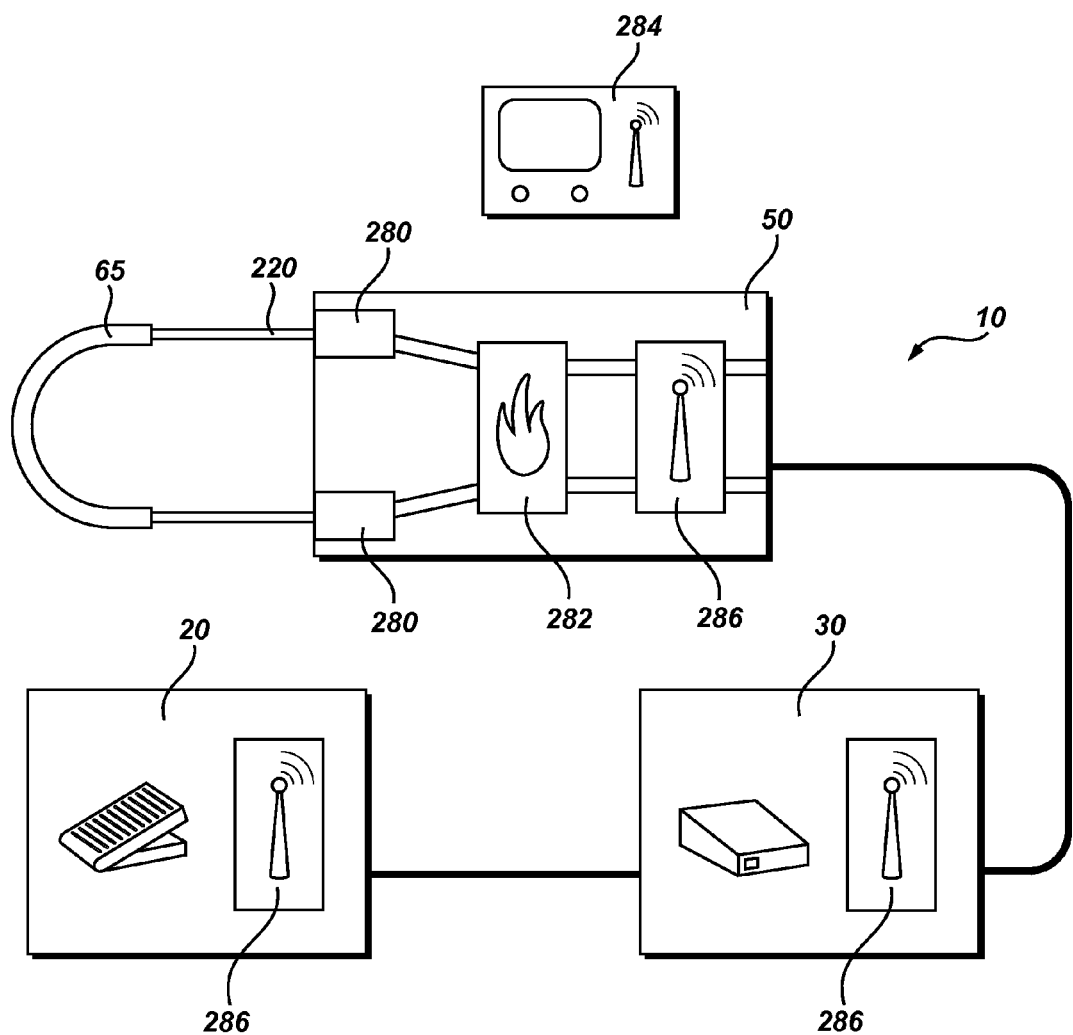
FIG. 4A shows a thermal surgical tool system with heat prevention terminals, heat sink, and wireless communication devices.

Turning now to FIG. 4A, a thermal surgical tool system 10 with connectors which attach to opposing first and second ends of a wire conductor is shown. The conductors as shown in FIG. 4A may be formed by heat prevention terminals 280, such as crimp connectors that provide thermal isolation. One or more heat sinks 282, and wireless communication devices 286 may also be included. The wire conductor 220 may be connected to the handheld surgical tool 50 by terminals 280 and/or a heat sink 282 at opposing first and second ends of the conductor. Portions of the conductor may extend into the handle into terminals, while the ferromagnetic coating portion of the conductor may extend beyond the handle. The terminals 280 may have a poor thermal conductance such that the terminals 280 reduce the heat transfer from the conductor into the handheld surgical tool 50. In contrast, the heat sink 282 may draw any residual heat from the terminals 280 and dissipate the heat into other mediums, including the air. Connectors and connections may also be achieved by wire bonding, spot and other welding, in addition to crimping.

Preventing thermal spread may be desirable because the other heated portions of the handheld surgical tool 50 may cause undesired burns, even to the operator of the handheld surgical tool 50. In one embodiment, terminals 280 are used to conduct the electric current, but prevent or reduce thermal conduction beyond the ferromagnetic coated conductor.

The thermal surgical tool may also communicate wirelessly. In one embodiment, the user interface for monitoring and adjusting power levels may be housed in a remote, wirelessly coupled device 284. The wirelessly coupled device may communicate with a wireless module 286 contained within the thermal surgical tool system 10, including the handheld surgical tool 50, the control system (such as foot pedal 20), and/or the power subsystem 30. By housing the control interface and display in a separate device, the cost of the handheld surgical tool 50 portion may be decreased. Similarly, the external device may be equipped with more processing power, storage and, consequently, better control and data analysis algorithms.

Figure 4B:
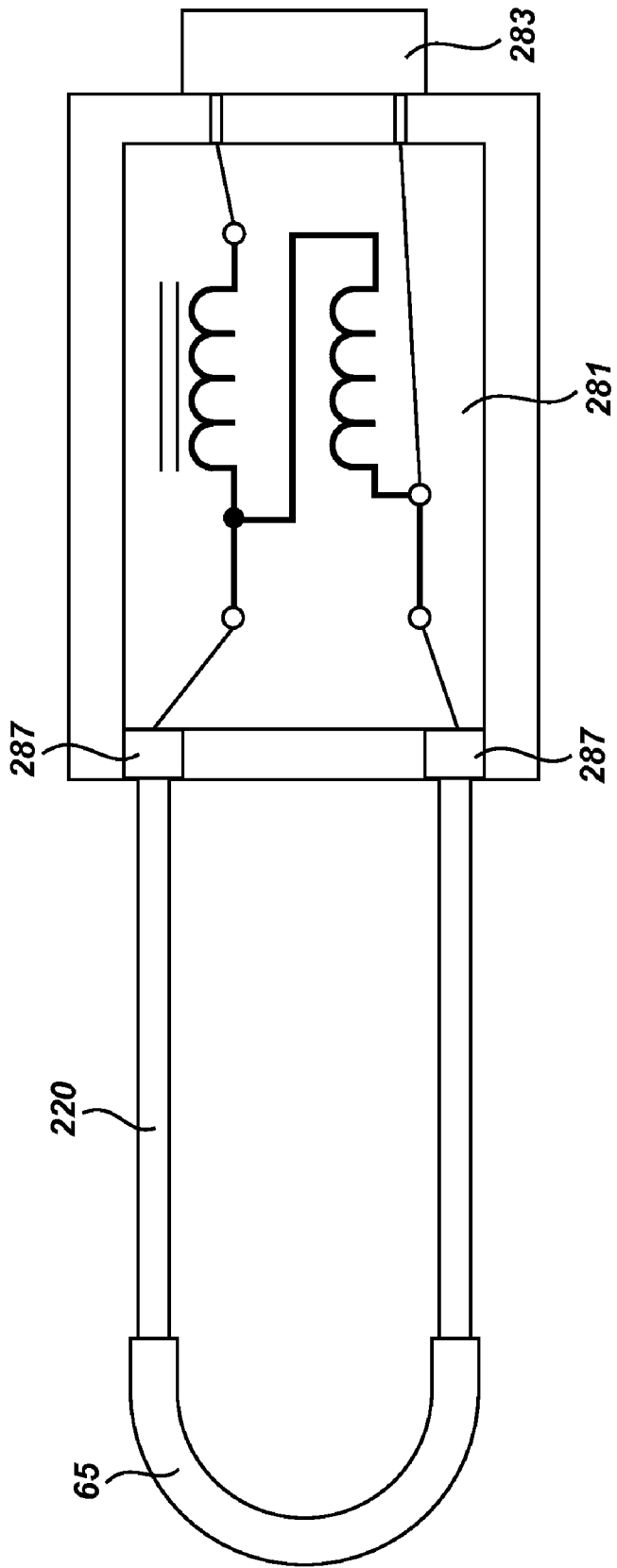
FIG. 4B shows a thermal surgical tool system with impedance matching network.

Turning now to FIG. 4B, a thermal surgical tool system with impedance matching network is shown. The impedance matching network may match the output impedance of the signal source to the input impedance of the load. This impedance matching may aid in maximizing power and minimizing reflections from the load.

In one embodiment, the impedance matching network may be a balun 281. This may aid in power transfer as the balun 281 may match the impedance of the ferromagnetic coated conductor terminals 287 to the amplifier cable terminals 283 (shown here as a coaxial cable connection). In such a configuration, some baluns may be able to act as a heat sink and provide thermal isolation to prevent thermal spread from the thermal energy at the ferromagnetic coating 65 transferred by the wire conductor 220 to terminals 287. The appropriate matching circuitry may also be placed on a ceramic substrate to further sink heat away or isolate heat away from the rest of the system, depending on the composition of the substrate.

It should be recognized that these elements discussed in FIGS. 4A and 4B can be used in conjunction with any of the embodiments shown herein.

Figure 5:
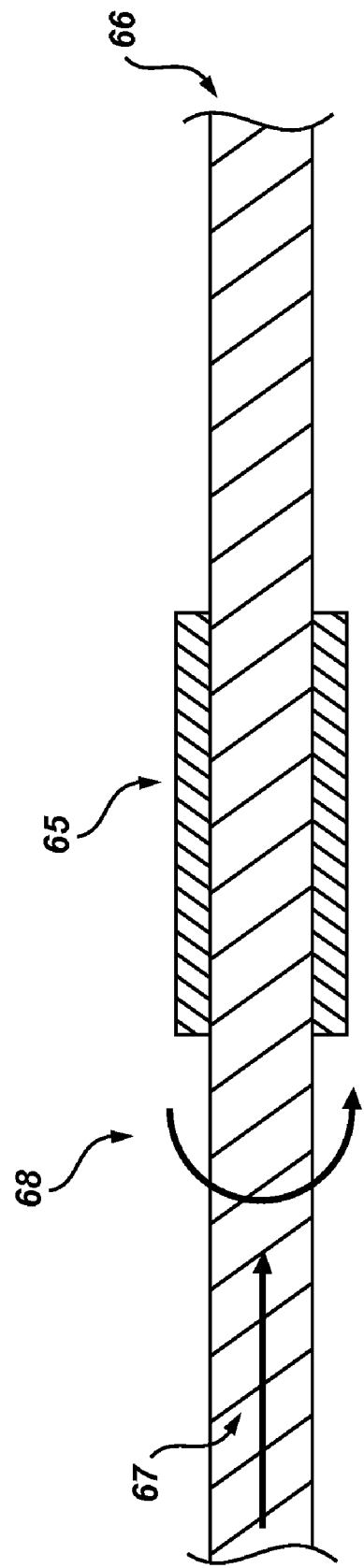
FIG. 5 shows a close-up, side cross-sectional view of a single layer ferromagnetic coated conductor tip in accordance with one aspect of the present invention.

Turning now to FIG. 5, a longitudinal cross section of the ferromagnetic coated conductor is shown. As an alternating current 67 is passed through conductor 66, a time varying magnetic field 68 is induced around conductor 66. The time varying magnetic field 68 is resisted by the ferromagnetic coating 65, causing the ferromagnetic coating 65 to dissipate the inductive resistance to the time varying magnetic field 68 as heat. Should the ferromagnetic coating 65 reach its Curie point, the magnetic resistive properties of ferromagnetic coating 65 become substantially reduced, resulting in substantially decreased resistance to time varying magnetic field 68. As there is very little mass to the ferromagnetic coating 65, the magnetic field causes the ferromagnetic coating 65 to quickly heat. Similarly, the ferromagnetic coating 65 is small in mass compared to conductor 66 and therefore heat will quickly dissipate therefrom due to thermal transfer from the hot ferromagnetic coating 65 to the cooler and larger conductor 66, as well as from the ferromagnetic coating 65 to the surrounding environment.

It should be appreciated that while the figures show a solid circular cross-section, the conductor cross-section may have various geometries. For instance, the conductor may be a hollow tubing such that it reduces thermal mass. Whether solid or hollow, the conductor may also be shaped such that it has an oval, triangular, square or rectangular cross-section.

As is also evident from FIG. 5, the ferromagnetic coating may be between a first section (or proximal portion) and a second section (or distal portion) of the conductor. This may provide the advantage of limiting the active heating to a small area, instead of the entire conductor. A power supply may also connect to the first and second section to include the ferromagnetic coating within a circuit providing power.

A method of using the surgical tool may include the steps of: selecting a conductor and plating a ferromagnetic coating upon the conductor.

Optional steps to the method may include: selecting a size of a conductor having a ferromagnetic coating disposed on a portion thereof according to a desired procedure; selecting a thermal mass of a conductor having a ferromagnetic coating disposed on a portion thereof according to a desired procedure; selecting a conductor from the group of loop, solid loop, square, pointed, hook and angled; configuring the oscillating electrical signal to heat the coating to between 37 and 600 degrees Centigrade; configuring the oscillating electrical signal to heat the coating to between 40 and 500 degrees Centigrade; causing the coating to heat to between about 58-62 degrees Centigrade to cause vascular endothelial welding; causing the coating to heat to between about 70-80 degrees Centigrade to promote tissue hemostasis; causing the coating to heat to between about 80-200 degrees Centigrade to promote tissue searing and sealing; causing the coating to heat to between about 200-400 degrees Centigrade to create tissue incisions; or causing the coating to heat to between about 400-500 degrees Centigrade to cause tissue ablation and vaporization. Treatment may include incising tissue, causing hemostasis, ablating tissue, or vascular endothelial welding.

Figure 6:
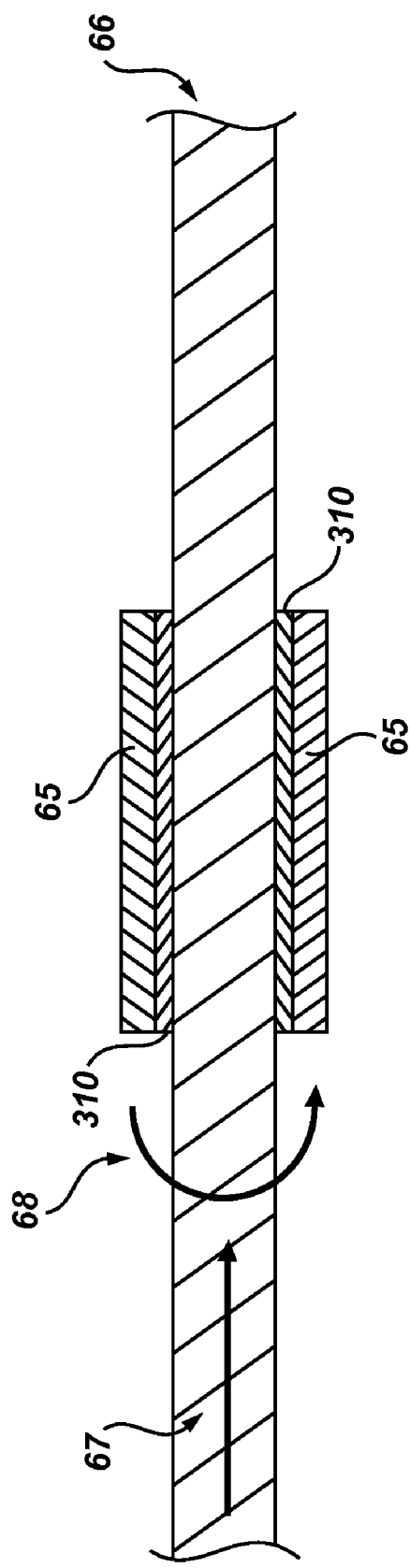
FIG. 6 shows a close-up, side cross-sectional view of a single layer ferromagnetic coated conductor tip with a thermal insulator in accordance with one aspect of the present invention.

Turning now to FIG. 6, a close-up, longitudinal cross-sectional view of a single layer cutting tip with a thermal insulator 310 is shown. A layer of thermal insulator 310 may be placed between the ferromagnetic coating 65 and the conductor 66. Putting a layer of thermal insulator 310 may aid in the quick heating and cool-down (also known as thermal response time) of the tool by reducing the thermal mass by limiting the heat transfer to the conductor 66.

The thickness and composition of the thermal insulator may be adjusted to change the power delivery and thermal response time characteristics to a desired application. A thicker coating of thermal insulator 310 may better insulate the conductor 66 from the ferromagnetic coating 65, but may require an increased power compared with a thinner coating of thermal insulator 310 in order to induce a magnetic field sufficient to cause the ferromagnetic coating to heat.

In FIGS. 7A-7G a plurality of embodiments are shown in which the surgical tip 210 is a tool which includes a wire conductor 220 which has a portion of its length coated with a relatively thin layer of ferromagnetic coating 65. As shown in FIGS. 7A-7G, the ferromagnetic coating 65 may be a circumferential coating around a wire conductor 220. When the wire conductor 220 is excited by a high frequency oscillator, the ferromagnetic coating 65 will heat through induction according to the power delivered, with an absolute limit provided by its Curie temperature. Because of the small thickness of ferromagnetic coating 65 and the tuned efficiency of high frequency electrical conduction of the wire at the position of the ferromagnetic coating 65, the ferromagnetic coating 65 will heat very quickly (i.e. a small fraction of a second) when the current is directed through the wire conductor 220, and cool down quickly (i.e. a fraction of a second) when the current is stopped.

Figure 7A:
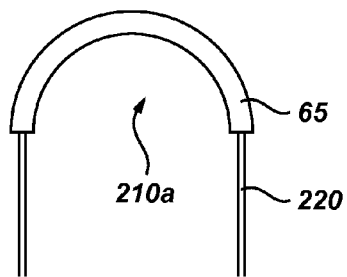
FIG. 7A shows a close-up view of ferromagnetic coated conductor surgical tool tip with a loop geometry in accordance with one aspect of the present invention.
Figure 7B:
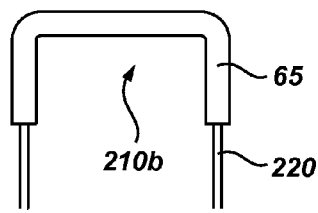
FIG. 7B shows a close-up view of a ferromagnetic coated conductor surgical tool tip with a generally square geometry in accordance with one aspect of the present invention.
Figure 7C:
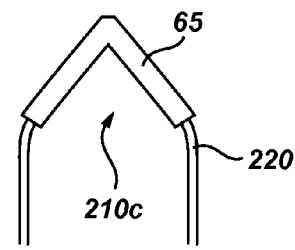
FIG. 7C shows a close-up view of a ferromagnetic coated conductor surgical tool tip with a pointed geometry.
Figure 7D:
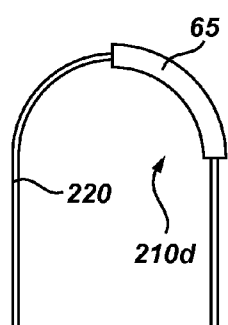
FIG. 7D shows a close-up view of a ferromagnetic coated conductor surgical tool tip with an asymmetrical loop geometry.
Figure 7E:
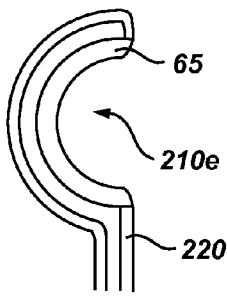
FIG. 7E shows a close-up view of a ferromagnetic coated conductor surgical tool tip with a hook geometry in which the concave portion may be used for therapeutic effect, including cutting.
Figure 7F:
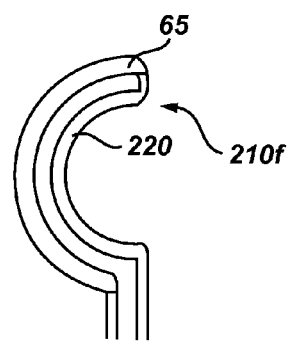
FIG. 7F shows a close up view of a ferromagnetic coated conductor surgical tool tip with a hook geometry in which the convex portion may be used for therapeutic effect, including cutting.
Figure 7G:
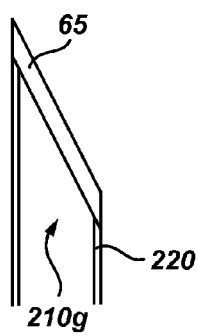
FIG. 7G shows a close up view of a ferromagnetic coated conductor surgical tool tip with an angled geometry.

Turning now to FIGS. 7A, 7B, 7C, 7D, 7E, 7F AND 7G, ferromagnetic coated conductor surgical tips 210a, 210b, 210c, 210d, 210e, 210f and 210g are shown. In each of these embodiments, a portion of wire conductor 220 is bent and coated with a ferromagnetic coating 65 such that the ferromagnetic coating 65 is only exposed to tissue where the desired heating is to occur. FIGS. 7A and 7B are loop shapes that can be used for tissue cutting or excision, depending upon the orientation of the tool to the tissue. FIG. 7A shows a rounded geometry, while FIG. 7B shows a squared geometry. FIG. 7C shows a pointed geometry for heated tip applications that can be made very small because the process of tissue dissection, ablation, and hemostasis requires only a small contact point. FIG. 7D shows an asymmetric tool with a loop geometry, where the ferromagnetic coating 65 is only disposed on one side of the tool. FIG. 7E shows a hook geometry where the ferromagnetic coating 65 is disposed on the concave portion of the hook. FIG. 7F shows a hook geometry where the ferromagnetic coating 65 is disposed on the convex portion of the hook. FIG. 7G shows an angled geometry, which may be used in similar situations as a scalpel. Use of these various geometries of ferromagnetic coating 65 upon a wire conductor 220 may allow the surgical tip to act very precisely when active and to be atraumatic when non-active.

In one representative embodiment, the electrical conductor may have a diameter of 0.01 millimeter to 1 millimeter and preferably 0.125 to 0.5 millimeters. The electrical conductor may be tungsten, copper, other metals and conductive non-metals, or a combination such as two dissimilar metals joined to also form a thermocouple for temperature measurement. The electrical conductor may also be a thin coating of conductor, such as copper, dispersed around a non-metallic rod, fiber or tube, such as glass or high-temperature plastic, and the conductive material, in-turn, may be coated with a thin layer of ferromagnetic material. The magnetic film forms a closed magnetic path around the electrically conductive wire. The thin magnetic film may have a thickness about 0.01-50% and preferably about 0.1% to 20% of the cross-sectional diameter of the wire. Due to the close proximity of the coating to the wire, a small current can produce high magnetic fields in the coating and result in significant temperatures. Since the magnetic permeability of this film is high and it is tightly coupled to the electrical conductor, low levels of current can result in significant hysteresis losses.

It is therefore possible to operate at high frequencies with low alternating current levels to achieve rapid inductive heating up to the Curie point. The same minimal thermal mass allows rapid decay of heat into tissue and/or the conductor with cessation of current. The tool, having low thermal mass, provides a rapid means for temperature regulation across a therapeutic range between about 37 degrees Celsius and 600 degrees Celsius, and preferably between 40 and 500 degrees Celsius.

While Curie point has been previously described as a temperature cap, instead, here a material with a Curie point beyond the anticipated therapeutic need may be selected and the temperature can be regulated below the Curie point.

While some tip geometries are shown in FIGS. 7A through 7G, it is anticipated that multiple different geometries of the ferromagnetic coated conductor 60 may be used.

Figure 8:
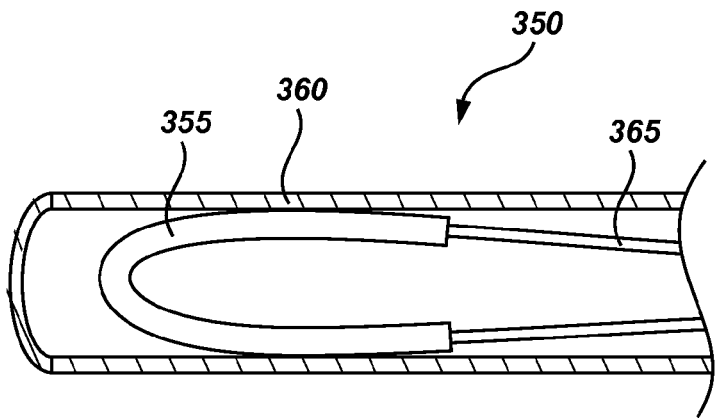
FIG. 8 shows a cut-away view of a retracted snare.

Turning now to FIG. 8, a cut-away view of a snare 350 in a retracted position is shown. A ferromagnetic coating is placed on a conductor to form a snare loop 355 and then placed within a sheath 360. While retracted, the snare loop 355 may rest within a sheath 360 (or some other applicator, including a tube, ring or other geometry designed to reduce the width of the snare when retracted). The sheath 360 compresses the snare loop 355 within its hollow body. The sheath 360 may then be inserted into a cavity where the target tissue may be present. Once the sheath 360 reaches the desired location, the snare loop 355 may be extended outside the sheath 360, and end up deployed similar to FIG. 9A. In one embodiment, the conductor 365 may be pushed or pulled to cause extension and retraction of the snare loop 355.

Figure 9A:
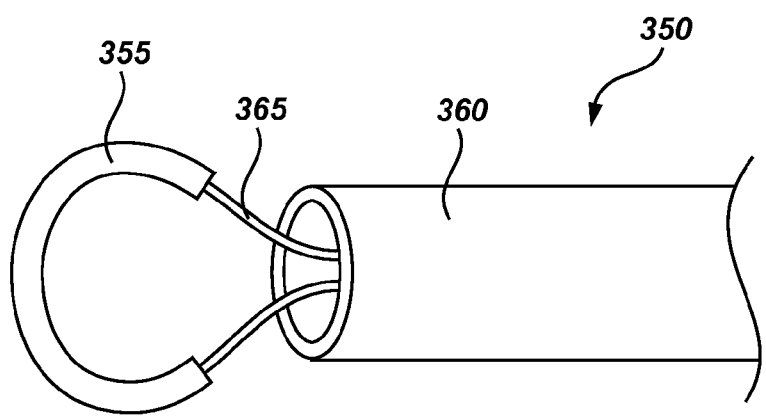
FIG. 9A shows a side view of an extended snare.

Turning now to FIG. 9A a side view of a snare 350 in an extended position is shown. Once extended, the snare loop 355 may be used in several different ways. In one embodiment, the snare loop 355 may be placed substantially around the target tissue, such that the tissue is within the snare loop 355. The ferromagnetic coating may then be caused to be inductively heated as discussed above. The snare loop 355 is then retracted back into the sheath 360 such that the target tissue is separated and removed from tissue adjacent the target tissue. The desired temperature range or power level may be selected for hemostasis, increased tissue separation effectiveness or other desired setting. For example, in one embodiment, the snare 350 is configured for nasal cavity polyp removal.

In another use, the snare 350 may be configured for tissue destruction. Once within the desired cavity, the snare may be extended such that a portion of the snare loop 355 touches the target tissue. The snare loop 355 may then be inductively heated such that a desired tissue effect occurs. For example, in one embodiment, the sheath may be placed near or in the heart and the snare loop 355 inductively heated to cause an interruption of abnormal areas of conduction in the heart, such as in atrial ablation.

Figure 9B:
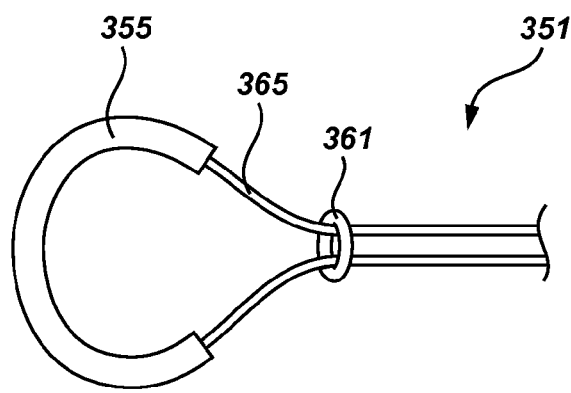
FIG. 9B shows an alternate embodiment of an extended snare.

Turning now to FIG. 9B, an alternate embodiment of a snare 351 is shown. The applicator may be a ring 361 instead of a sheath as in FIG. 9A. Similar to the sheath, the ring 361 may be used to force the loop into an elongated position. Various devices could be used to hold the ring in place during use.

A method of separating tissue may include the steps of: selecting a conductor having a ferromagnetic coating disposed on a portion thereof; placing the portion of the conductor having the ferromagnetic coating within a tube; inserting the tube into a cavity; deploying the portion of the conductor having the ferromagnetic coating within the cavity; and delivering an oscillating electrical signal to the conductor so as to heat the ferromagnetic coating while the heated ferromagnetic coating is in contact with a target tissue.

Optional steps may include: deploying step further comprises placing the ferromagnetic coating substantially around the target tissue; retracting the ferromagnetic coating portion of the conductor into the tube; causing hemostasis in the target tissue; forming the conductor into a bent geometry such that a portion of the conductor remains within the tube; and touching a ferromagnetic covered portion of the bent geometry to the target tissue.

A method of removing tissue may include the steps of: selecting a conductor having at least one portion having a ferromagnetic conductor disposed thereon; and placing the ferromagnetic conductor around at least a portion of the tissue and pulling the ferromagnetic conductor into contact with the tissue so that the ferromagnetic conductor cuts the tissue.

Optional steps may include: using a conductor having a plurality of ferromagnetic conductors in an array or passing an oscillating electrical signal through the conductor while the ferromagnetic material is in contact with the tissue.

Figure 10A:
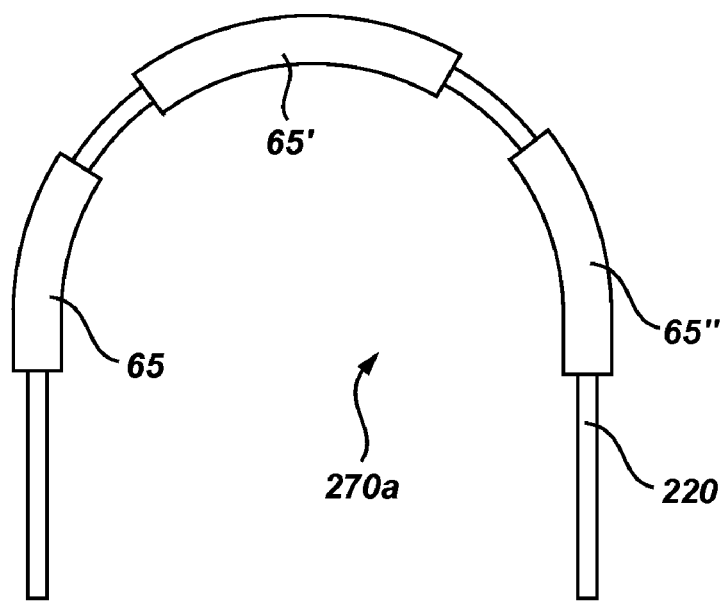
FIG. 10A shows a close-up view of a ferromagnetic coated conductor surgical tool with a loop geometry and linear array of coatings.

Turning now to FIG. 10A, a close-up view of a cutting tip with a loop geometry and linear array of coatings is shown. While the above embodiments have disclosed a continuous ferromagnetic coating on a conductor, in another embodiment, there are more than one coating separated by gaps on a single conductor. This is termed a linear array of ferromagnetic elements (an example of a parallel array of ferromagnetic elements can be seen in FIGS. 18A-18C).

Figure 10B:
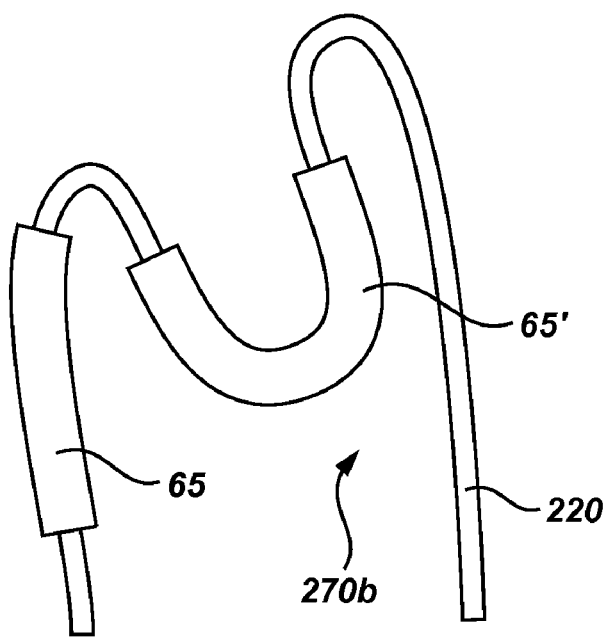
FIG. 10B shows a close up view of a ferromagnetic coated conductor surgical tool with an alternate hook geometry and linear array.

In one embodiment, a loop geometry 270a may have multiple ferromagnetic coatings 65, 65', and 65" which are separated by gaps on a wire conductor 220. In another embodiment shown in FIG. 10B, a close up view of a cutting tip with an alternate hook geometry 270b and linear array of ferromagnetic coatings 65 and 65' is shown on a wire conductor 220. The linear array may include the advantage of allowing flexibility in building a desired thermal geometry.

The conductor 220 which may be formed of an alloy having shape memory, such as Nitinol (nickel titanium alloy). A Nitinol or other shape memory alloy conductor can be bent into one shape at one temperature, and then return to its original shape when heated above its transformation temperature. Thus, a physician could deform it for a particular use at a lower temperature and then use the ferromagnetic coating to heat the conductor to return it to its original configuration. For example, a shape memory alloy conductor could be used to form a snare which changes shape when heated. Likewise, a serpentine shape conductor can be made of Nitinol or other shape memory alloy to have one shape during use at a given temperature and a second shape at a higher temperature. Another example would be for a conductor which would change shape when heated to expel itself from a catheter or endoscope, and then enable retraction when cooled.

In another embodiment, the ferromagnetic coatings may be formed in such a way that an individual coating among the linear array may receive more power by tuning the oscillating electrical energy. The tuning may be accomplished by adjusting the frequency and/or load matching performed by the power source to specific ferromagnetic coatings.

Figure 11:
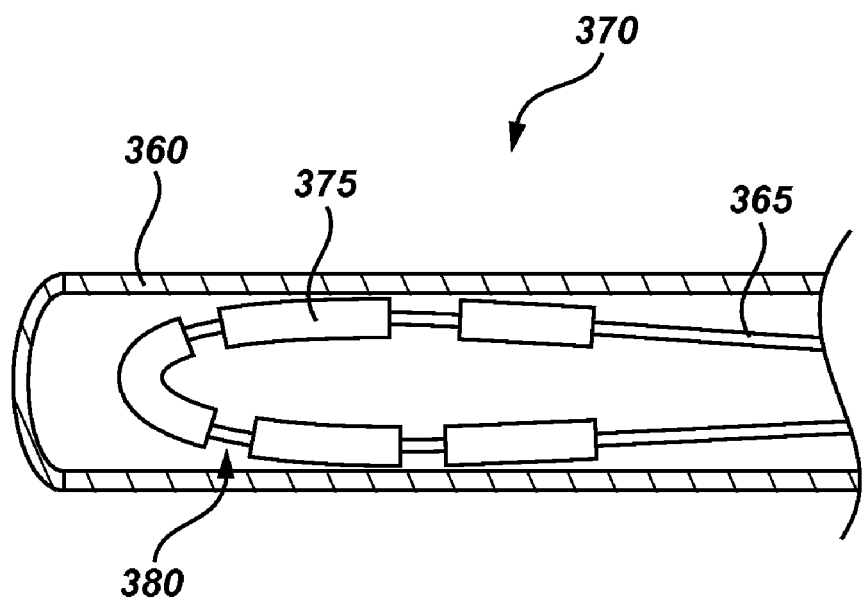
FIG. 11 shows a cut-away view of a retracted snare with an array of coatings.

Turning now to FIG. 11, a cut-away view of a snare tool 370 with a linear array of coatings in a retracted position is shown. In some embodiments, some ferromagnetic coatings may lack the elasticity to effectively bend into a retracted position. Therefore, individual coating segments 375 may be separated by gaps 380 such that the conductor 365 may be flexed while the coating segments 375 may remain rigid.

Figure 12:
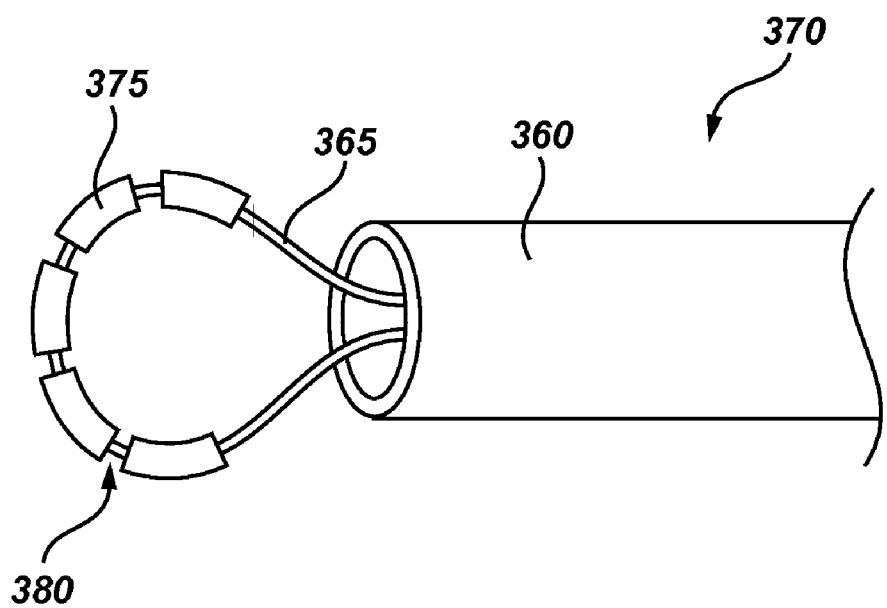
FIG. 12 shows a side view of an extended snare with a linear array of coatings.

Similarly, the snare tool 370 may be extended, as seen in FIG. 12. The gaps 380 between the coating segments 375 may be adjusted such that the heating effect will be similar in the gaps 380 as the coating segments. Thus, the snare tool 370 with linear array may act similar to the snare with flexible coating in FIGS. 8 and 9.

Turning now to FIG. 13, a cross-sectional view of a single layer cutting tip in the ferromagnetic-coated region is shown. The ferromagnetic coating 65 is disposed over a wire conductor 220. The ferromagnetic coating 65 provides several advantages. First, the ferromagnetic coating 65 is less fragile when subjected to thermal stress than ferrite beads, which have a tendency to crack when heated and then immersed in liquid. The ferromagnetic coated conductor 60 has been observed to survive repeated liquid immersion without damage. Further, the ferromagnetic coating 65 has a quick heating and quick cooling quality. This is likely because of the small amount of ferromagnetic coating 65 that is acted upon by the magnetic field, such that the power is concentrated over a small area. The quick cooling is likely because of the small amount of thermal mass that is active during the heating. Also, the composition of the ferromagnetic coating 65 may be altered to achieve a different Curie temperature, which would provide a maximum self-limiting thermal ceiling attribute to the device.

Turning now to FIGS. 14A, 14B and 15, a multilayer surgical tool tip is shown. A cross section of 14A along the 221 line may result in FIG. 14B which shows alternating layers of wire conductor 220 and 220' and ferromagnetic coating 65 and 65'. Heating capacity may be increased by layering thin layers of alternating conductor 220 and 220' material and ferromagnetic coating 65 and 65', while still maintaining quick heating and cooling advantages. FIG. 15 shows an axial cross-sectional view from FIG. 14A along the 390 line. The alternating layers of conductor 220 and 220', and ferromagnetic coating 65 and 65' may also be seen.

Figure 16:
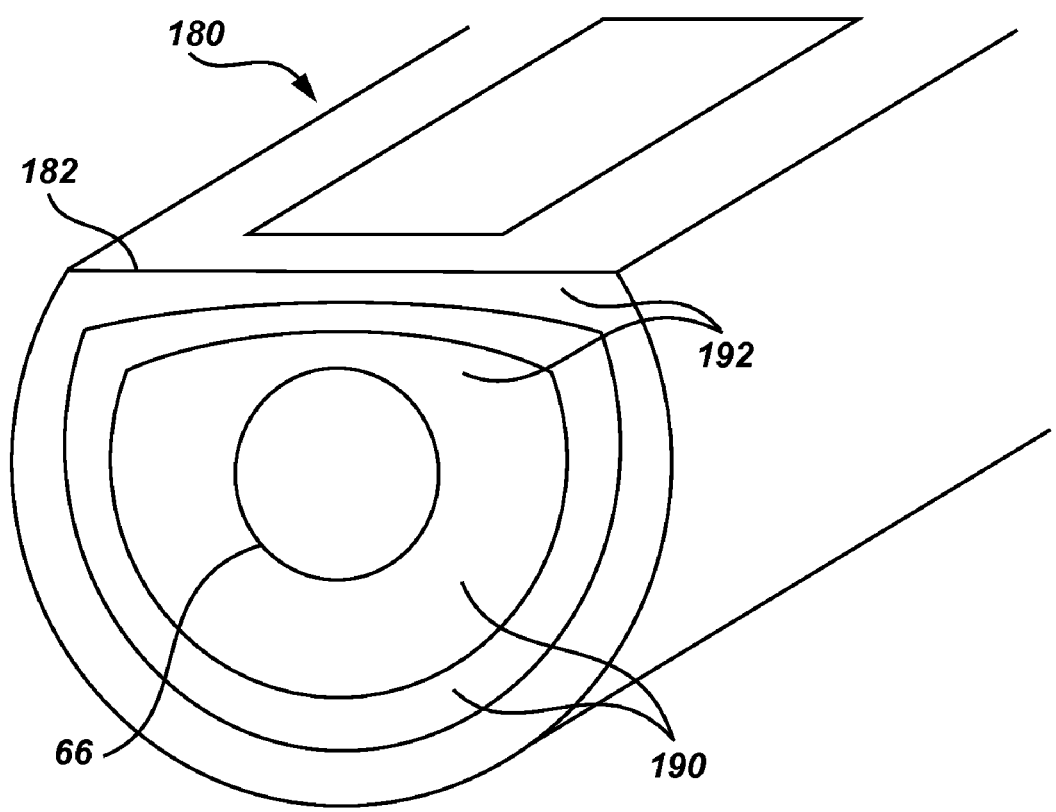
FIG. 16 shows a cross-sectional view of a flattened side cylindrical geometry ferromagnetic coated conductor showing electromagnetic lines of flux; in accordance with one aspect of the present invention.

Turning now to FIG. 16, a flattened side cylindrical geometry is shown. The flat surface 180 can be manufactured to cause a thin plating 182 of ferromagnetic coating on the conductor 66 relative to the thicker plating around the rest of the conductor 66. This thin plating 182 may result in selective first onset heating in this flat surface 180. Inductive heating may be proportional to flux density within the magnetically permeable coating. In one embodiment, an asymmetrically thinned coating has a small cross sectional thickness and may generate higher hysteresis losses in the form of heat. Thus, a therapeutic temperature may be achieved with yet lower power at the flat surface 180 with higher flux density 192 compared to a cooler opposite side with a diminished flux density 190. An advantage is that fast temporal response and distributed optimal heating at the tissue interface may be enhanced.

Figure 17:
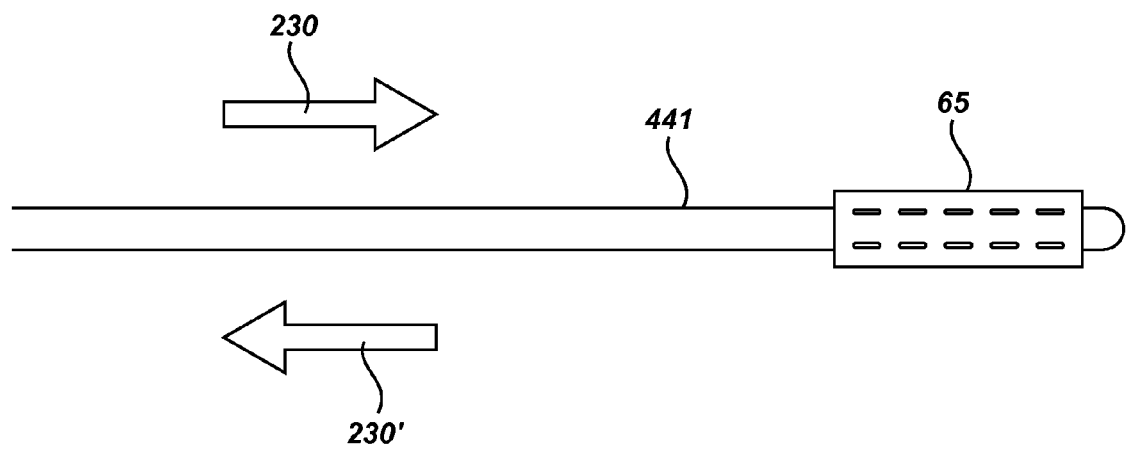
FIG. 17 shows a closed conductor tip in accordance with another aspect of the present invention.

Turning now to FIG. 17, the ferromagnetic coating 65 may also be configured to focus the temperature increase on the outside of the ferromagnetic coating 65, further reducing the time needed to cool the ferromagnetic coating 65 in a relatively high power application. An example of such a configuration is shown in FIG. 17, wherein the fields generated by the current flow 230 and 230' (the arrows) may have a cancelling effect with respect to each other within the ferromagnetic coating 65 surrounding both conductors, keeping the ferromagnetic material between the looped conductor 441 cooler than the ferromagnetic material at the perimeter.

Turning now to FIGS. 18A-18D, several surgical tip 194 geometries are demonstrated. In FIG. 18A, a surgical tip 194a with a single small diameter electrically conductive wire plated with the thin film magnetic material 196 is shown. In FIG. 18B, the surgical tip 194b with two small diameter electrically conductive wires plated with the thin film magnetic material 196' is shown. In FIG. 18C, a surgical tip 194c with three small diameter electrically conductive wires plated with the thin film magnetic material 196" are shown. It is thus contemplated that a tip geometry may consist of a plurality of small diameter electrically conductive wires plated with the thin film magnetic material. Such a design maintains the temporal heat responsiveness (rapid onset, rapid offset) essential to the dynamic surgical environment due to minimal mass of the ferromagnetic coated conductor. It is thus possible to configure a flat tine with two or more spaced wires as a practical monothermal or multithermal tool. Further, the tips 194a, 194b and 194c may also be exchangeable as seen in FIG. 18D, which has a receptacle 198 for the tips 194 in FIGS. 18A-18C. It will be appreciated that the generator system may be configured to adjust the power jointly delivered to two or more of the conductors and that a user control (as shown in other figures) can be provided for that purpose.

The ferromagnetic coating 65 can be used to contact the tissue directly, or, a non-stick coating, such as TEFLON (PTFE), or similar material, could be applied over the ferromagnetic coating and conductor to prevent sticking to the tissue. Alternatively, the ferromagnetic coating could be coated with another material, such as gold, to improve biocompatibility, and/or polished, to reduce drag force when drawing through tissue. The ferromagnetic coating could also be coated by a thermally-conductive material to improve heat transfer. In fact, a single coating may be selected to have multiple desirable properties.

Turning now to FIGS. 19 to 22, the ferromagnetic coated conductor may be attached to a primary geometry. The primary geometry may provide an attachment surface or an internal site for the conductor with a ferromagnetic coating. Thus the advantages of the ferromagnetic coating on a conductor may be combined with the advantages of the primary geometry and its corresponding material. The primary geometry may be selected for various reasons, including but not limited to, material strength, rigidity, heat conduction, resistance to thermal heat transfer, surface area, or additional functionality.

As used herein, a primary geometry means a structure to which a ferromagnetic coated conductor may be attached and which defines the shape of the tool. For example, a primary geometry could be a scalpel, tines of forceps, the face of a spatula, or a ball shape at the end of a probe. The conductor geometry, therefore, may be disposed upon the primary geometry, may extend through a hole in the primary geometry, and/or be embedded in the primary geometry. For example, a primary geometry may be a scalpel, while the conductor geometry may be the serpentine shape of a ferromagnetic coated wire upon the primary geometry.

Figure 19A:
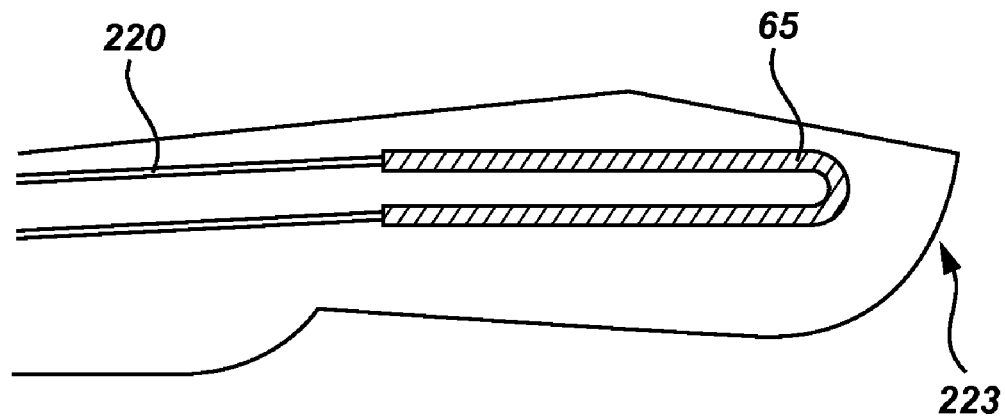
FIG. 19A shows a normally cold cutting scalpel with alternate inductive ferromagnetic thermal function.
Figure 19B:
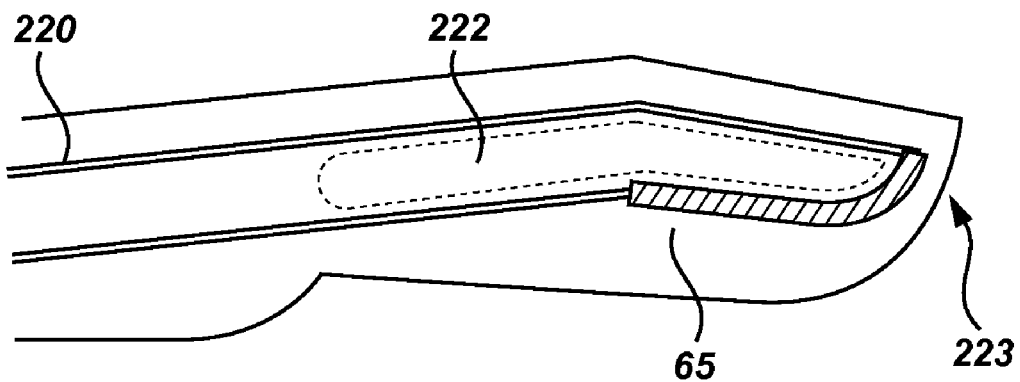
FIG. 19B shows an alternate embodiment of a normally cold cutting scalpel with alternate inductive ferromagnetic thermal function.

Turning now to FIGS. 19A and 19B, a cold cutting scalpel 223 with alternate inductive ferromagnetic thermal function is shown. The cold cutting scalpel 223 may be used for cutting through the application of a blade having a cutting edge and having a secondary thermal function activated when required, such as for coagulation. In the embodiments shown in FIGS. 19A and 19B, this is achieved by placing a ferromagnetic coated wire conductor 220 upon the side of a scalpel shaped primary geometry, which can cut tissue without activation of the conductor or ferromagnetic coating 65. The cold cutting scalpel 223 may be used classically to make incisions in tissue. However, if the patient begins to bleed, the cold cutting scalpel 223 operator may activate the ferromagnetic coated conductor and place the side of the cold cutting scalpel 223 (and correspondingly, the ferromagnetic coated conductor) upon the bleeding tissue. The thermal effect may then cause the tissue to seal and cease bleeding. After deactivation of the ferromagnetic coated conductor, the scalpel operator may then return to making incisions with the benefits of a cold cutting scalpel.

There are several advantages to use of such a cold cutting scalpel 223. The dual-use tool does not require the cold cutting scalpel 223 operator to remove one tool and replace it with another, causing risk of further damage and delay. Due to the ferromagnetic coating 65, the cold cutting scalpel 223 may also have a quick thermal response time (the heat-up and cool-down time) in the region of the ferromagnetic coating 65 such that the cold cutting scalpel 223 may be used on the targeted area and reduce waiting time. In cases where it may be desirable to heat the entire cold cutting scalpel, thermal response time may be further reduced by removing a center portion 222 of the blade (as seen in FIG. 19B), resulting in a non-contiguous portion of the blade that may occur between or adjacent to the conductor path. Removing the center portion 222 of the blade may further reduce the thermal mass and correspondingly the thermal response time.

In one embodiment, related to FIG. 19B, the ferromagnetic coating may be limited to a part of the scalpel, such as the tip of the cold cutting scalpel 223. This limiting would cause only the tip to heat, while the remaining portions of the primary geometry would remain at a lower temperature. This limiting of the heating to a portion of the primary geometry in proximity to the ferromagnetic coating may provide a higher degree of accuracy and usefulness in smaller spaces. Similarly, the ferromagnetic coated wire conductor 220 may form a pattern, such as a zigzag or serpentine pattern, across the surface of the cold cutting scalpel 223 to increase the heating coverage of the surface.

Scalpel effects may also be enhanced by the thermal effects of the ferromagnetic coated wire conductor 220. In one embodiment, the scalpel may have multiple parts with different temperature ranges addressable to each part. For example, energy to the scalpel blade may be used to cut, while energy to the sides of the blade may be used to coagulate tissue walls. In another embodiment, the ferromagnetic coated wire conductor 220 may be activated to provide additional cutting ability when moving through more difficult tissue. In another embodiment, the ferromagnetic coated conductor may be activated to provide a more smooth cutting process in conjunction with the scalpel blade. A user control may be used to select a power setting to be delivered by a power source, which may be correlated with a desired temperature or tissue effect.

Turning now to FIG. 20A, a thermal surgical tool with a spatula shaped geometry is shown. The spatula 224 may have a ferromagnetic coating 65 on a wire conductor 220 that follows the perimeter of the spatula shape as shown. In an alternate embodiment, the ferromagnetic coated portion of the wire conductor 220 may form a pattern across the surface of the geometry such that the surface is more evenly covered by the ferromagnetic coated portion of the wire conductor 220.

A spatula geometry may be useful for various tissue effects and procedures. In one embodiment, the spatula is used for hemostasis or tissue welding during surgery. After an incision has been made, if needed, the spatula may be applied to the incised tissue to achieve hemostasis or even tissue welding. In another embodiment, the spatula is pressed into tissue and thermal energy is used for tissue ablation.

Turning now to FIG. 20B, the thermal surgical tool with a spatula shaped geometry is shown in forceps form. The spatula forceps 225 may be used in combination such that each spatula has a separate power control or the forceps may have a power control in common. Such a tool can be used to clamp vessels to stop blood flow, and then cause hemostasis and cutting of the vessels with heat.

Turning now to FIGS. 20C and 20D, a side view of FIG. 20A is shown in two different embodiments. The ferromagnetic coating and wire conductor may be attached to the primary geometry in several ways. In one embodiment shown in 20C, the ferromagnetic coating 65 and conductor may be attached to the surface of the primary geometry. Alternatively in 20D, the ferromagnetic coating 65 and conductor may be embedded within the primary geometry. Depending upon the desired effect, the tools depicted in FIGS. 20A, 20B, 20C and 20D can be applied to tissue in such a manner that the side of the tool on which the ferromagnetic coated conductor 65 is located can contact the tissue, or the opposite side can be applied to the tissue.

Figure 21A:
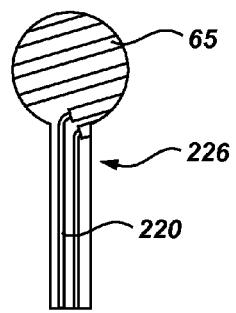
FIG. 21A shows a thermal surgical tool with a ball shaped geometry and horizontal winding.
Figure 21B:
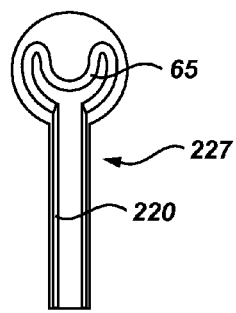
FIG. 21B shows an alternate embodiment of a thermal surgical tool with a ball shaped geometry and horseshoe configuration.
Figure 21C:
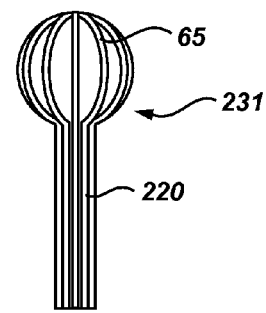
FIG. 21C shows an alternate embodiment of a thermal surgical tool with a ball shaped geometry and vertical orientation.

Turning now to FIGS. 21A, 21B and 21C, a thermal surgical tool with a ball shaped geometry is shown. In one embodiment, a horizontally wrapped ball 226 or a vertically wrapped ball 231 may be internally or externally wrapped with a wire conductor 220 with a ferromagnetic coating 65 as seen in FIG. 21A and FIG. 21C. In another embodiment, shown in FIG. 21B, a ball geometry 227 may contain a wire conductor 220 with a ferromagnetic coating prepared in another shape, such as a horseshoe shape. In the embodiments, a ball-shaped heating element may be formed which can be used to coagulate or provide a therapeutic effect over a large surface area of tissue. The ball may also be effective in tissue ablation, as it may radiate thermal energy in most, if not all, directions.

Figure 22A:
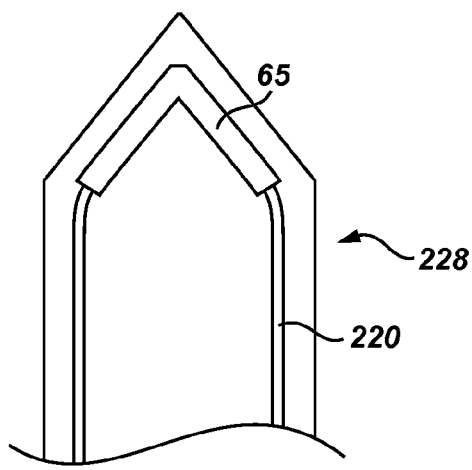
FIG. 22A shows a thermal surgical tool with a pointed geometry.

Turning now to FIG. 22A, a thermal surgical tool with a pointed geometry is shown. The pointed tool 228 may have a ferromagnetic coating 65 on a wire conductor 220 that follows the perimeter of the pointed tool shape as shown. In an alternate embodiment, the ferromagnetic coated portion of the wire conductor 220 may form a pattern across the point surface of the geometry such that the point surface is more evenly covered by the ferromagnetic coated portion of the wire conductor 220. The pointed tool 228 may be particularly useful for making incisions that penetrate layers of tissue, providing a means for coagulation while cutting, such as coagulation of tissue around the site of trocar insertion for laparoscopic surgery.

Figure 22B:
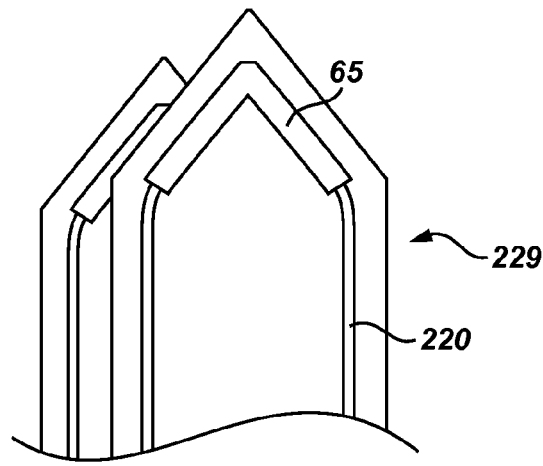
FIG. 22B shows a thermal surgical tool with a pointed geometry in a forceps configuration.

Turning now to FIG. 22B, the thermal surgical tool with a pointed geometry is shown in forceps form. The pointed forceps 229 may be used in combination such that each pointed geometry has a separate power control or the forceps may have a power control in common. Such a tool can be configured for achieving hemostasis and cutting in small vessel ligation.

While some primary geometries have been shown in singular form, the primary geometries may be used in combination. This may include two or more of the same primary geometry or differing primary geometries, including forceps applications. Each primary geometry may be commonly controlled for power or have separate power controls for each primary geometry. Furthermore, solid primary geometries may be altered similar to the scalpel primary geometry shown above such that portions of the primary geometries may be removed to reduce thermal mass and correspondingly, thermal response time.

While some of the primary geometries have been shown to have symmetrical construction, the primary geometries may have asymmetrical or directional construction such that only a portion of the primary geometry would be active. This may be accomplished by placing the ferromagnetic coating only on the portion of conductor wire residing on the area of the primary geometry desired to be active. For example, the spatula geometry may be configured to be active in one area if the ferromagnetic coated conductor is not symmetrically positioned on the spatula structure. This may be further enhanced by providing a pattern, such as a zigzag or serpentine pattern, on the desired active portion of the geometry.

Figure 22C:
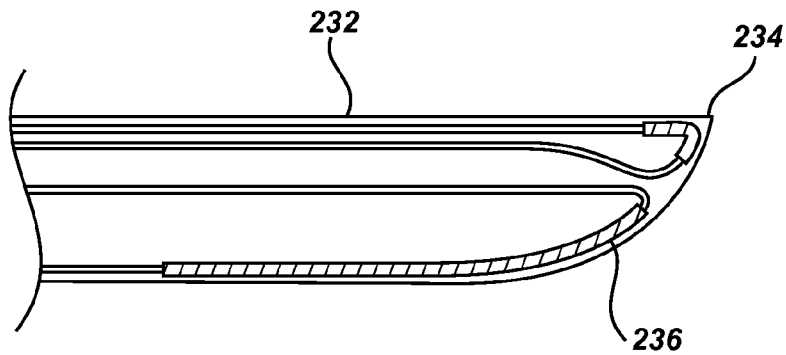
FIG. 22C shows a thermal surgical tool having two different activatable thermal zones.

In another embodiment, a portion of the primary geometry may be activated. By using multiple conductors with a ferromagnetic coating 65 attached to different portions of a primary geometry, a portion of the primary geometry may be selectively activated. For example, a scalpel geometry 232 may be divided into a tip portion 234 and a face portion 236 as shown in FIG. 22C. A scalpel operator may then choose whether to activate only the tip or the tip in conjunction with the face of the scalpel geometry, depending on the surface area desired. Similarly, in a forceps application, the forceps may be divided into inside and outside portions. If the forceps operator desires to remove something that may be surrounded by the forceps, such as a polyp, the internal portions may be activated while the external portions remain deactivated. If opposing sides of a void need to be sealed, the outside surfaces of the forceps may be activated.

By using multiple conductors with a ferromagnetic coating 65 attached to different portions of a primary geometry and separately controlled power sources, different portions of the primary geometry may be activated at the same time for different uses or effects. For example, an edge portion of a primary geometry may be activated for cutting while the blade portion may be activated for hemostasis.

A method of treating tissue may thus include the steps of: selecting a primary geometry having a conductor disposed thereon, the conductor having a ferromagnetic coating disposed on a portion thereof; disposing the ferromagnetic coating into contact with the tissue; and delivering an oscillating electrical signal to the conductor so as to heat the ferromagnetic coating and treat the tissue.

Optional steps of the method may include choosing a primary geometry selected from the group of scalpel, spatula, ball and pointed geometry. Treating of the tissue may include incising, causing hemostasis, ablating or vascular endothelial welding.

A method for tissue destruction may include the steps of selecting a conductor having a ferromagnetic coating disposed on a portion thereof; and delivering an oscillating electrical signal to the conductor so as to heat the ferromagnetic coating and destroy tissue.

Optional steps of the method may include monitoring the tissue and ceasing delivery of the oscillating electrical signal to the conductor when the desired tissue destruction has occurred or undesired tissue effects are to be prevented.

A method for forming a surgical instrument may include the steps of: selecting a primary geometry; coating a conductor with ferromagnetic material; and disposing the conductor on the primary geometry.

Optional steps of the method may include providing electrical connections on the conductor configured for receiving oscillating electrical energy.

Figure 23A:
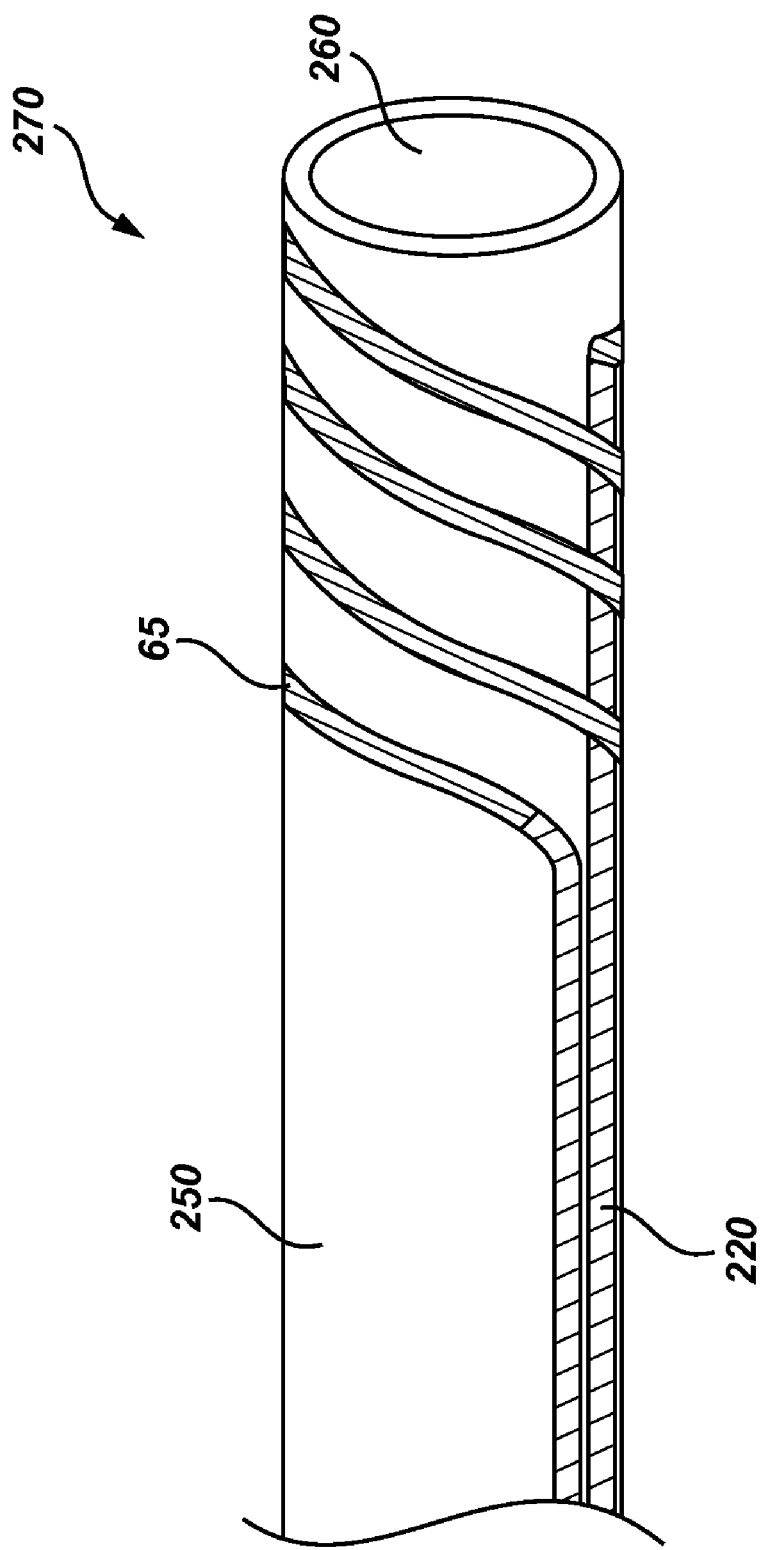
FIG. 23A shows a perspective view of a catheter having a coil of ferromagnetic coated conductor disposed around the tip of the catheter.

Turning now to FIG. 23A, a catheter 270 having a conductor 220 which is at least partially coated with ferromagnetic material disposed around the tip of the catheter is shown. Depending upon the therapeutic effect desired, the location of the coil of ferromagnetic coating 65 could instead be inside the catheter tip, or a single loop of ferromagnetic coated conductor having a circumference which approximates that of the catheter central channel 260 could be located at the end of the catheter tip.

Figure 23B:
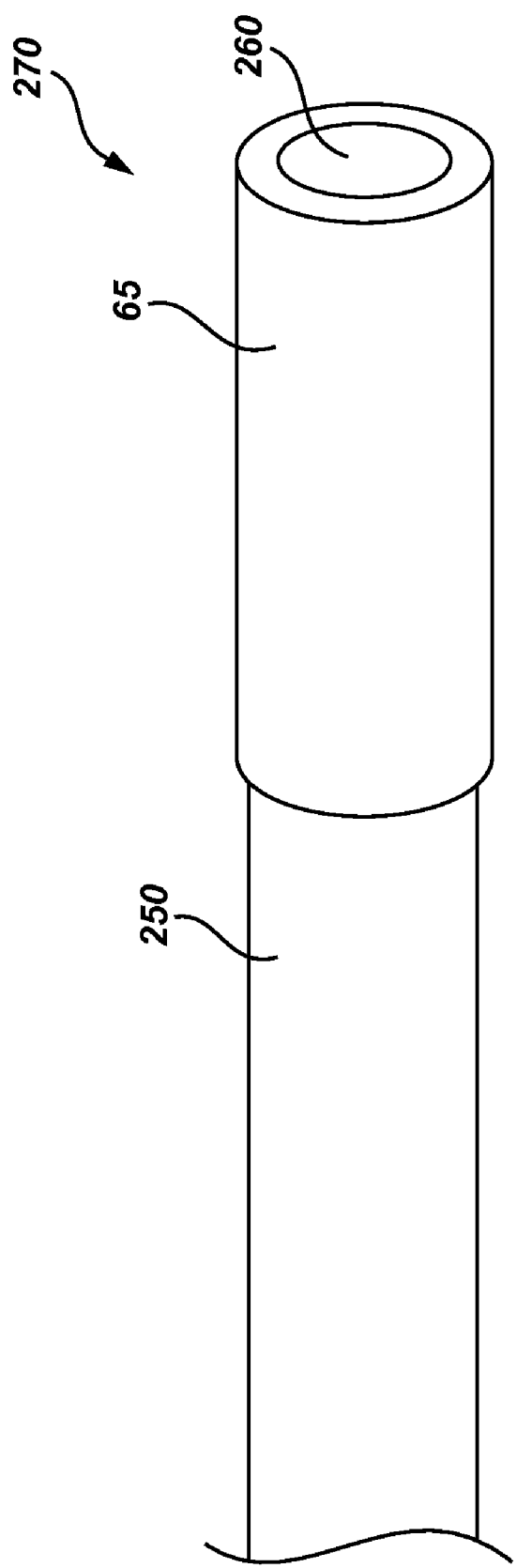
FIG. 23B shows a perspective view of a ferromagnetic coated conductor surgical catheter tip.

In FIG. 23B, another ferromagnetic coated catheter 270 is shown. While in some embodiments the conductor may be a wire, coil, or annular structure, a ferromagnetic coated catheter 270 could also be formed which would serve as an alternate conductor 250 with a ferromagnetic coating 65. In this embodiment, the catheter could consist of two coaxial conductors, separated by an insulator. At the distal tip of the catheter 270, a conductive coating can be applied such that a continuous electrical path is created by the coaxial conductors. The ferromagnetic coating can be dispersed about the external diameter surface near the distal tip of the catheter, as shown in FIG. 23B, or, upon the end of the catheter, on the annular surface connecting the coaxial conductors. This would allow the ferromagnetic coated catheter 270 to perform other functions, such as irrigation, aspiration, sensing, or, to allow viewing access via optical fibers, through a central channel 260, as is common in many interventional as well as open and minimally invasive surgical procedures. Furthermore, the central lumen of the catheter could be used to provide access to other sensing modalities, including, but not limited to, impedance and pH.

It will be appreciated that the catheter 270 or an endoscope could be provided with both a bipolar electrode and/or a thermal element. Thus, the benefits of such a catheter or endoscope could be combined with the multi-mode surgical tool discussed herein.

Figure 24:
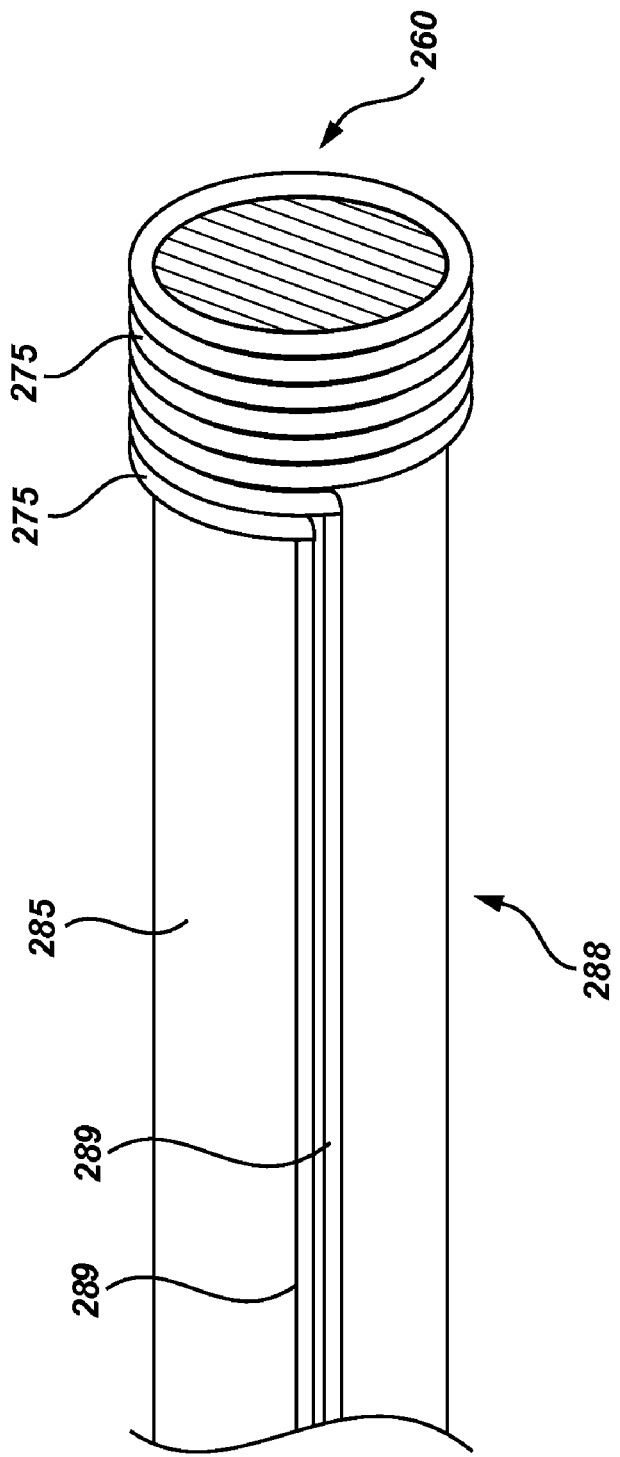
FIG. 24 shows a side view of an alternate embodiment of a ferromagnetic coated conductor surgical catheter tip.

Turning now to FIG. 24, a side view of an alternate embodiment of a ferromagnetic coated conductor surgical tool catheter tip 288 is shown. In one embodiment, the conductor may consist of a ferromagnetic coated conductor positioned on a substrate 285 forming a body with a central channel. The ferromagnetic coating may consist of a plated ferromagnetic coating 275 on top of a conductor 289. The plating may be placed on the outside of the substrate 285 such that the thermal effects are directed externally. This may allow the catheter tip to apply thermal tissue effects to tissue walls.

In another embodiment, the inside of the substrate may contain the conductor 289 and ferromagnetic coating 275 such that the thermal effects are directed internally. An internal coating may allow delivery of a meltable solid to a desired area, such as in fallopian tube sealing and osteosynthesis applications.

Alternatively, the ferromagnetic coating 275 may surround the entrance to the central channel 260, such that the thermal effects may be directed in front of the tip. Having the thermal energy be directed in front of the central channel 260 entrance may aid in taking a tissue sample or removal of material, such as a polyp.

The plating may be accomplished through multiple methods. The substrate 285 may be extruded, molded or formed from various materials including high temperature thermoplastic, glass, or other suitable substrate material. The actual plating may be accomplished through electroplating, electroless plating, vapor deposition, or etching, or some combination thereof. Thus through the plating process, a catheter tip 288 may be formed with a ferromagnetic coating 275 on a conductor 289 with a continuous path.

The catheter may also have multiple channels. One channel may be a deployment channel for the ferromagnetic coated conductor. Another channel may be used for one or more sensors or sources, or even each sensor or source in its own channel—such as a temperature sensor, illumination source and endoscope. Other channels may include delivery, irrigation or aspiration of substances, including those associated with treatment, such as in osteosynthesis or fallopian tube sealing. In fact, the ferromagnetic coating may aid in the melting of such substances.

Figure 25:
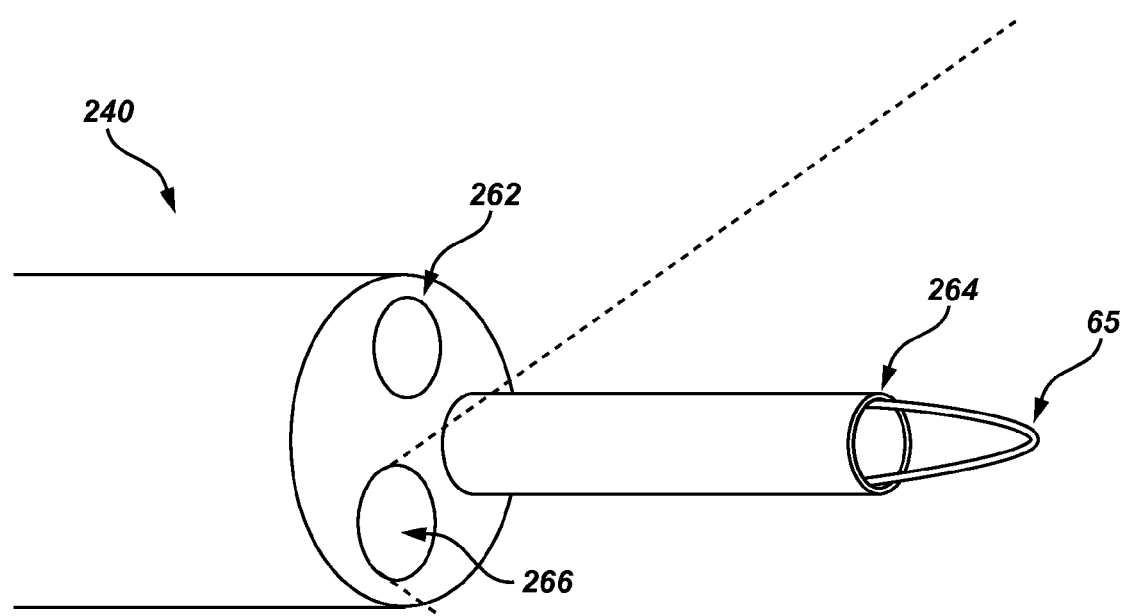
FIG. 25 shows an alternate embodiment of a ferromagnetic coated conductor surgical tip disposed within an endoscope.

Turning now to FIG. 25, an endoscope 240 with a viewing channel 262 of rod lens type or organized fiber bundle type aside a light emitting source 266 is shown. A loop coagulator/cutter 264 is shown which consists of the ferromagnetic coated conductor 65. Such an adaptation is contemplated in snare applications such as colon polypectomy or sealing and cutting applications in various laparoscopic procedures. Other sensing modalities include near field tumor cell detection or infrared heat monitoring. Tool configurations similar to the described endoscope 240 can be embodied in tools that can be delivered to target tissue through the lumen of a catheter.

In one embodiment, tumor cells are caused to be tagged with materials that fluoresce when exposed to ultra-violet light. The endoscope 240 may contain a light source 266, and sensor or optics within the channel 262 that return the detected florescence. The ferromagnetic coating 65 portion of the endoscope 240 may then be directed at the tagged tissue for destruction.

In another embodiment, materials are deposited around target tissue or bone in a solidified condition. Once delivered, the materials are melted to conformation at the site by activation by the endoscope 240 described above. Examples of use of this embodiment include fallopian tube sealing and osteosynthesis. Furthermore, such materials could be removed by melting with the same or similar endoscope 240, and aspirated through a central lumen of the endoscope 240. In yet further applications, materials may be delivered in liquid form, and cured by a thermal heating process induced by the endoscope 240.

Alternatively, the conductor may be part of a bundle of fibers. The fibers may be contained within a catheter or otherwise bundled together. The conductor may have a ferromagnetic coating, while the other fibers may have other purposes that include visual observation, sensing, aspiration, or irrigation.

A method of tissue ablation may include the steps of: selecting a catheter with a ferromagnetic covered conductor; causing the ferromagnetic covered conductor to touch tissue to be ablated; and delivering power to the ferromagnetic covered conductor.

Optional steps may include: directing the catheter to the tissue through the aid of an endoscope; selecting a ferromagnetic coated conductor disposed on the catheter; selecting a ferromagnetic coated conductor contained within the catheter; causing the ferromagnetic coated conductor to be deployed from the catheter; or touching the ferromagnetic coated conductor to the tissue to be ablated.

A method of delivering a substance into a body may include the steps of: selecting a catheter with a ferromagnetic coated conductor; placing a substance in the catheter; inserting the catheter into a body; and causing power to be sent to the ferromagnetic coated conductor.

Optional steps may include: selecting a substance for osteosynthesis; selecting a substance for fallopian tube sealing; or melting the substance in the catheter.

A method of treating tissue may include the steps of: selecting a catheter with a ferromagnetic coated conductor; placing the catheter in contact with tissue; and selecting a power setting. The temperature range may correspond to a temperature range or desired tissue effect. The desired tissue effect may be selected from the group of vascular endothelial welding, hemostasis, searing, sealing, incision, ablation, or vaporization. In fact, the power setting may correspond to a desired tissue effect.

Figure 26:
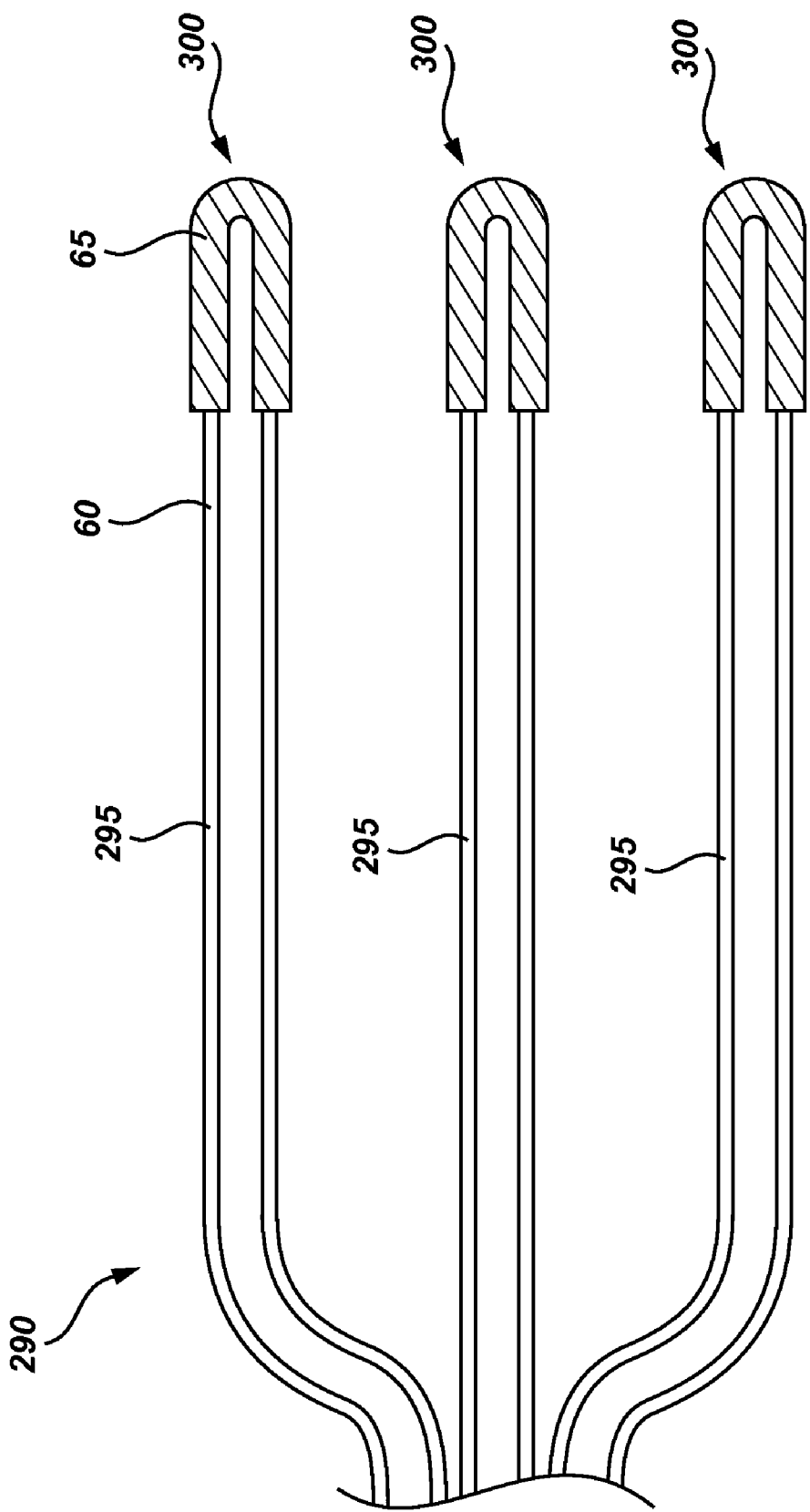
FIG. 26 shows a tissue ablation tool.

Turning now to FIG. 26, a tissue ablation tool 290 is shown. In typical applications of tissue ablation, an arm or tine 295 is inserted into undesired tissue. One or more tips 300 may be activated such that the tissue temperature is raised to a desired level for a desired amount of time. After the activation has succeeded in holding a temperature for a desired amount of time, or undesired effects are noticed, the one or more tips 300 may be deactivated and removed from the tissue.

In one embodiment, a conductor may be contained in one or more arms or tines 295 with tips 300 that may contain ferromagnetic coatings 65. The tips 300 may be inserted into tissue and temperature controlled until tissue destruction occurs or one or more undesired tissue effects occur. The tissue effects may be monitored through sensors in the tines 295 or externally.

Sensors may be placed in multiple ways. In one embodiment, the sensor is placed in the tine and away from a ferromagnetic coated tip 300. In another embodiment, one tip 300 may have a ferromagnetic coating, while an alternate tip 300 may have no coating, but a sensor contained within. The sensors may monitor tissue effects or return signals to be observed or processed. This may include sensors such as temperature sensors, cameras and remote imaging. In another embodiment, the temperature may be monitored through external imaging.

The sensor may thus form part of a feedback loop. By monitoring one or more tissue effects, the ablation tool may self-adjust power settings. This self-adjustment may allow the system to operate below the Curie point and still maintain a desired tissue effect and/or temperature range.

In the case where more than one tip 300 is used, the tips 300 with a ferromagnetic coating 65 may be individually controlled such that the thermal profile is concentrated in the desired area. This may also allow a second tine to monitor tissue effects, while a primary tine is used to perform the thermal function.

While a diagram has been shown of a multi-tip tissue ablation tool in FIG. 26, a single tissue ablation tool may be made in a configuration similar to FIG. 7C.

Besides the advantages of uses in tissue, the surgical tool may also be self-cleaning. In one embodiment, when activated in air, the tool may achieve a temperature sufficient to carbonize or vaporize tissue debris.

While the above embodiments have disclosed a ferromagnetic conductor operating solely in an inductive heating modality, in accordance with the principles of the present invention, a thermal surgical system may be combined with other technology to form multi-mode surgical instruments. The multi-mode surgical instruments may leverage the advantages of multiple energy modalities, while potentially reducing some inherent drawbacks of either modality by itself. (While a few examples are discussed, it will be appreciated that a multi-mode surgical modality can be accomplished by modifying virtually any of the embodiments discussed above).

As used herein, multiplex means communicating the two or more signals over a single channel. In many cases, the channel may be a wire or cable, and the signals may be imposed independently, or simultaneously, over the single channel.

Different modalities may be combined. Thermal modalities may be formed from thermal elements that produce thermal energy and include, but are not limited to, inductive heating, conductive heating and resistive heating devices. Electrosurgery modalities may be formed from electrosurgical elements that transmit electrical energy into the target tissue and include, but are not limited to, monopolar and bipolar modalities. Mechanical modalities may be formed from ultrasonic elements that transmit mechanical energy in the form of pressure waves (also known as ultrasonic energy) into the target tissue and include, but are not limited to ultrasound tissue disruption. These modalities may have different advantages in combination.

Inductive heating may be the result of a substance's resistance to magnetic or electrical forces. Inductive heating may include such effects as the ferromagnetic effect, as described above, or a ferroelectric effect in which substances may resist changes in electric fields.

As used herein, "conductive heating" or "conductive heating element" refer to the transfer of thermal energy from a heat source to an endpoint through one or more intervening elements. For example, a surgical tool may use thermal heat transfer to cause thermal energy to be transferred from a heat source, such as a ferromagnetic inductive heater, through an intervening element, such as a wire, to a surgical tip, the endpoint. The process of conductive heating may be similar to the heat sinks described above; only the thermal transfer is directed to the tissue rather than another medium. See also the description of heat sinks relative to FIG. 4A.

Resistive heating may also be used as a thermal modality. A resistance heating element may resist the passage of electrical current and thus dissipate power in the form of thermal energy.

In the monopolar surgery modality, a surgeon may use a single electrode to pass electrical current through the body. Often, a second electrode is attached to the back, legs or the surgical table to complete the circuit. However, some monopolar devices also operate without a return electrode with low-powered high frequency current because of the body's self-capacitance acting as a return path by the displacement current.

In the bipolar surgery modality, the electric current may be applied to the patient through multiple electrodes. In one embodiment, the electric current is applied through electrodes on opposite tines of forceps. The tissue between the forceps may thus be heated.

In the ultrasound tissue disruption modality, ultrasonic vibrations are used to incise or destroy or ablate tissue in a region through mechanical energy transfer. In one embodiment, a handpiece contains a vibrating component or structure that mechanically transmits the ultrasonic vibrations in tissues.

It is believed that these modalities may have advantages and disadvantages when used as a sole modality. However, when multiple modalities are used together, some disadvantages may be reduced and potential advantages gained.

Figure 27:
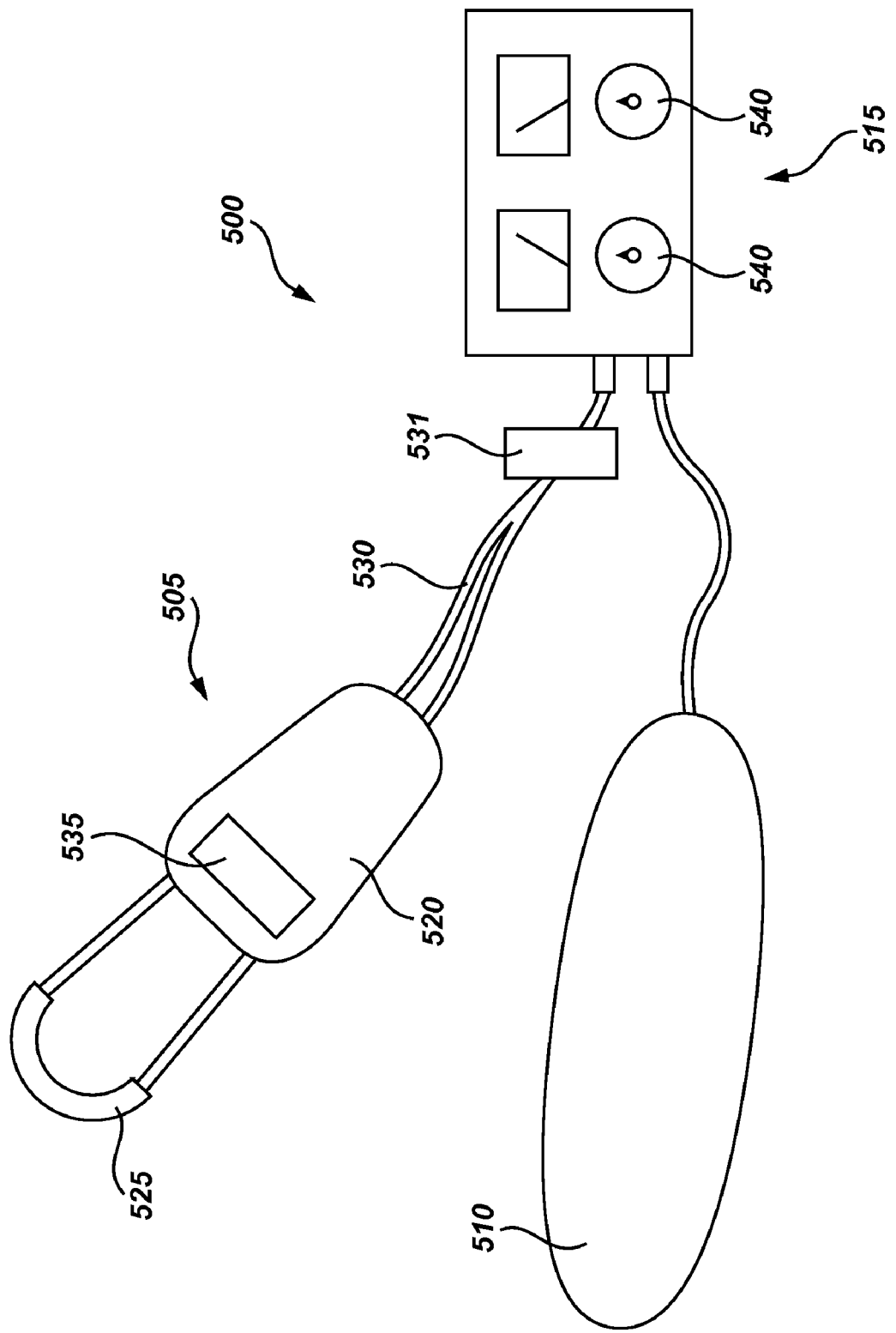
FIG. 27 shows a multi-mode surgical tool with monopolar and thermal modalities.

Turning now to FIG. 27, a multi-mode surgical tool 500 with monopolar and thermal modalities is shown. The multi-mode surgical tool 500 may include a handpiece 505, a secondary electrode 510 and a power supply 515. The power supply 515 may provide two signals to the handpiece 505 to activate the thermal and monopolar modalities in a surgical tip 525. The monopolar modality may then pass current through tissue (typically the patient's body) to a secondary electrode.

In a multiplexed embodiment, the monopolar signal may be prevented from using the cable 530 as the return path by a filter 531. The filter may prevent the monopolar signal from returning along the cable 530, but allow the thermal signal to return along the cable 530. While the filter 531 is shown between the power supply 515 and the handpiece 505, it may be integrated elsewhere along the signal path, including within the power supply, within the handpiece or on the return path just after the ferromagnetic coating.

The signal may be multiplexed in many different ways. The signal may be generated by a specialized signal generator, multiplexed before the amplifier, multiplexed after an amplifier, or even multiplexed at the handpiece.

The handpiece 505 may include a handle 520 and surgical tip 525. In some embodiments, there may be a cable 530 connection between the handpiece 505 and the power supply 515. The handpiece may also contain controls for operating the surgical tip, such as a button 535.

The surgical tip may be constructed in several different ways. One surgical tip may accept a multiplexed signal. Another surgical tip may require separate signal pathways and structures. Thus a surgical tool may have a electrosurgical electrode, such as a monopolar electrode, and a thermal element as separate structures. These structures may be totally separate, adjacent or overlap.

In the multiplexed embodiment, the surgical tip may be constructed of a single ferromagnetic coating upon a conductor. The ferromagnetic coating receives two waveforms corresponding to a monopolar modality and an inductive heating modality. The monopolar waveform is transmitted through the ferromagnetic coating to the patient, while the inductive heating waveform (or signal) is converted to thermal energy at the ferromagnetic coating. A filter may insure the transfer of the monopolar signal to the tissue as it blocks the monopolar electrical signal return path. The monopolar waveform may be between 200 kHz and 2 MHz. Preferably, the monopolar signal may be between 350 kHz and 800 kHz. The inductive heating waveform may be, for example, between 5 MHz to 24 GHz, and preferably between 40 MHz and 928 MHz.

In one embodiment, the monopolar signal is between 350 kHz and 800 kHz. The inductive heating waveform is in the 40.68 MHz ISM band. The waveforms are multiplexed by the power supply 515 and sent along the cable 530 to the handpiece 520. (Alternatively, other methods of multiplexing the waveforms may also be used, such as joining two wires carrying signals after the power supply or other multiplexing methods).

The handpiece 520 connects the cable 530 to the surgical tip 525 which may be composed of a ferromagnetic coating on a conductor. The ferromagnetic coating converts the 40.68 MHz signal into thermal energy, while transmitting the 350 kHz to 800 kHz monopolar signal through the tissue and eventually to the secondary electrode 510.

The monopolar modality may maintain the advantages of cutting, while the inductive heating modality produces hemostasis and may reduce the force required to draw the surgical tip through tissue. Thus, when in use, the surgeon may use RF waveforms suited to cutting, while using the thermal contact of the coated portion for sealing or hemostasis. Thus deep tissue effects associated with RF coagulation or fulguration waveforms or blended waveforms may be minimized while maintaining the benefit of RF cutting. The combined instrument may also be configured with separate RF frequencies or current pathways to optimize both ferromagnetic inductive heating and electrosurgical cutting.

In a separate signal pathway embodiment, the surgical tip 525 may be composed of a monopolar electrode disposed upon a thermal structure. The heat from the thermal structure, such as a ferromagnetic coated conductor, may be transferred through the electrode to tissue. In some embodiments, the thermal structure will be separated from the monopolar electrode by an electrically insulating, thermally conductive coating. The electrode and thermal structure may have individual electrical connections such that the correct signal may be sent to each.

The electrode may also be disposed next to the thermal structure. In one embodiment, the monopolar electrode is arranged such that the electrode encounters the tissue first, thereby cutting or ablating tissue. The trailing thermal structure may then encounter the freshly cut or ablated tissue and apply thermal hemostasis. Thus, it will be apparent that the modalities may be used completely independently, simultaneously on the same tissue, or closely following one another depending on the surgical instruments configuration and the effects desired by the physician.

While the embodiments above discuss the multi-mode surgical tool 500 as using a monopolar modality for cutting and a thermal modality for hemostasis, it should be recognized that either modality may be adapted to other tissue effects, whether the same or different. For example, in one embodiment, the monopole electrode and the thermal element are active at the same time. The monopolar electrode waveform and the thermal element waveform may both be optimized for incising. This may make the incision through tissue easier and more effective. In another embodiment, the thermal structure may be used for incising and the monopolar electrode may be used for hemostasis.

The monopolar multi-mode device may use the functions of either modality in tandem or separately. In fact, the oscillators may be separately adjusted. In an embodiment, a monopolar modality and thermal modality are activated at different times. The monopolar modality is activated to incise tissue. If hemostasis is needed, the thermal portion may be activated on demand, and may remain deactivated until required by the surgeon.

The power supply 515 may control the modalities separately or in tandem. For instance, a press of button 535 may cause both modalities to activate in tandem. Or, the button 535 may be configured to activate one or both modalities. However, the power supply may also control the power delivery to each modality via separate controls 540, which may be separately adjustable.

The multi-mode surgical tool may be disposed upon a catheter. The catheter may allow more functionality such as sensing, visual feedback, irrigation, aspiration, or substance delivery. In fact, the catheter may be flexible or rigid depending on the desired application.

A process of using a thermally adjustable multi-mode surgical tool may include the steps of: generating a first oscillating electrical signal forming an approximate standing wave with maximum current and minimum voltage substantially at a first load disposed along a conductor which has a portion of the conductor coated by ferromagnetic material to create thermal effects in tissue; and generating a second oscillating electrical signal along a conductor to create electrosurgical tissue effects in tissue.

The process may include the optional steps of: creating hemostasis in the tissue; causing tissue cutting; generating the first oscillating electrical signal and the second oscillating electrical signal in a single conductor; or generating the first oscillating electrical signal and the second oscillating electrical signal during overlapping periods of time. In fact the conductor may comprise a monopolar electrode.

A method for incising and sealing tissue may include the steps of: selecting a surgical tool, the tool having a conductor with a ferromagnetic coating disposed on a portion thereof, the tool also having an electrode; disposing the electrode in contact with tissue; disposing the ferromagnetic coating into contact with the tissue; delivering an oscillating electrical signal to the electrode so as incise the tissue; and delivering an oscillating electrical signal to the conductor so as to heat the ferromagnetic coating and seal the tissue.

The method may include the optional steps of: heating the ferromagnetic coating to provide hemostasis and selecting a monopolar electrode.

Figure 28A:
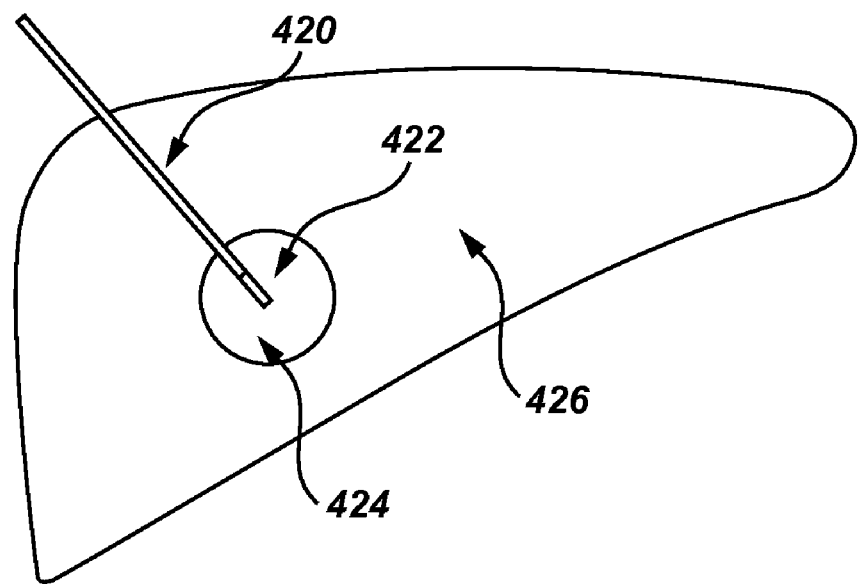
FIG. 28A shows a multi-mode tissue ablation tool within a metastasis in tissue, such as in a liver.
Figure 28B:
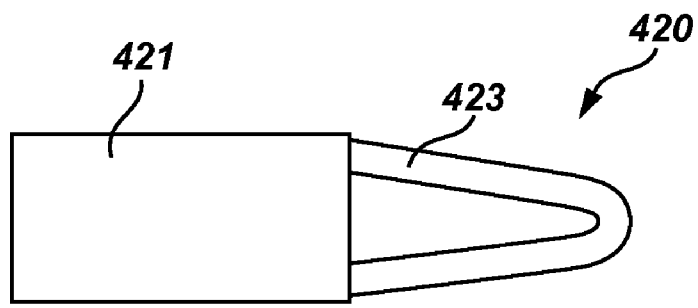
FIG. 28B shows a close-up the ablating probe of FIG. 28A.
Figure 28C:
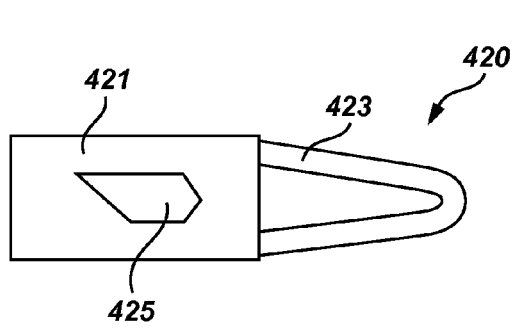
FIG. 28C shows a close-up of an ablating probe with a sensor.

Turning now to FIGS. 28A, 28B and 28C, a lesioning or ablating probe 420 is shown. A lesioning probe may be placed within a lesion and heated to a specified temperature for a specified period of time. Generally, the desire is to kill or ablate the lesion while leaving other tissue minimally effected. During this process, the progression of the heat is monitored such that any unforeseen irregularities may cause the procedure to abort rather than further damage the patient's tissues. This progression is known as the heat shape or shaping effect. The ferromagnetic coating may itself be biocompatible, or, if it is not, it may have at least a portion covered in a second coating, such as a biocompatible material or non-stick material. In one embodiment, a ferromagnetic inductive tip 422 may be covered by a coating of gold (sometimes referred to as a cap). The tip coating of gold may be biocompatible, yet highly heat conductive and therefore practical for a more slow temporal heating and shaping effect. Although gold may be used, other biocompatible materials, such as silver, may be used as well. A conductive coating may aid in the transmission of monopolar energy, if covering the monopolar electrode.

The probe 420 may operate through the use of more than one modality. In one embodiment, an electrode may be optimized for incising for insertion into the tissue, while a thermal element is optimized for tissue ablation. Both the electrode and the thermal element may be contained in or near the tip 422. Thus the electrosurgical element may allow insertion of the instrument into the desired tissue, while the thermal portion may be used for ablation. Similarly, the tool may also be configured for RF tissue ablation and thermal incision.

In one embodiment of a method of using the probe 420, the probe 420 may be guided stereotactically into a tissue to selectively lesion a functional path. Common examples include functional stereotactic brain lesioning in the treatment of movement disorders, pain, and depression. One advantage compared against commonly employed single modality monopolar and single modality bipolar probe configurations is that the shape of the lesion may be controlled by the thermal conduction properties and/or electrical impedance properties, giving the clinician better ability to adjust the shaping effect in the tissue. Alternatively, ablation for intended gradual heat destruction of a tissue can be achieved with similar designs, typically employing higher temperatures. Such an embodiment is easily adapted for treatment of tumor metastases in various organs. Another advantage of the multiple modalities may be giving the ability to target tissue where the electrical and thermal effects overlap, rather than choosing a less perfect targeting of a single modality.

As illustrated in FIG. 28A, the lesioning or ablating probe 420 may be positioned into a metastasis 424 in tissue, e.g. an organ such as the liver 426. Once in the liver, etc., one or both modalities may cause the metastasis 424 to heat to a desired temperature for a desired period of time. Thermal modalities may cause the tip 422 to heat. The shape of the temperature envelope may be examined by temperature sensing and or external means such as ultrasound. Similarly, the electrical effect of an electrical modality may be measured as well, such as impedance measurements. After the elapsed time, the probe 420 may be removed from the lesion. Thus, the undesired tissue of the tumor may be killed while minimizing harm to the surrounding tissues. Distributed tissue ablative effects can be optimized by cross-sectional monitoring of the electrical impedance changes in tissue, as illustrated in bronchial thermoplasty, prostatic hypertrophy, and volumetric reduction (lesioning).

Figure 28D:
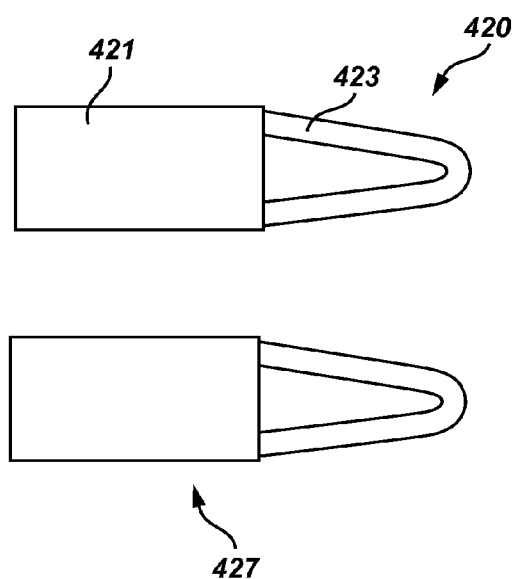
FIG. 28D shows a close-up of a multiple tip ablating probe.

Turning now to FIG. 28B, a close-up of the ablating probe of FIG. 28A is shown. The probe may have an elongate body 421 that ends in a multi-mode tip 420, such as a ferromagnetic coated conductor 423. The multi-mode tip 420 may include a sensor 425 as seen in FIG. 28C. In one embodiment as shown in FIG. 28D, the ablating probe may include a first multi-mode tip 420 and a second tip 427. In one embodiment, the first tip may include the multi-mode functionality and the second tip 427 may contain a sensor. In another embodiment, the first and second tip (also known as a primary tip and secondary tip) may contain multi-mode tips.

A method of tissue ablation may include the steps of: selecting a tip with electrosurgical and thermal modalities; inserting the tip into the undesired tissue; and activating one or more of the modalities within the undesired tissue.

A method for treating tissue may include the steps of: selecting a surgical handpiece and delivering thermal energy at, at least, 58 degrees Celsius to the tissue from the handpiece and delivering electrical energy from the handpiece to the tissue to thereby treat the tissue.

It should be recognized that multi-mode surgical tips with a ferromagnetic coating may have a relevant Curie point large enough to encompass a desired set of therapeutic temperature ranges without crossing the Curie point.

Figure 29:
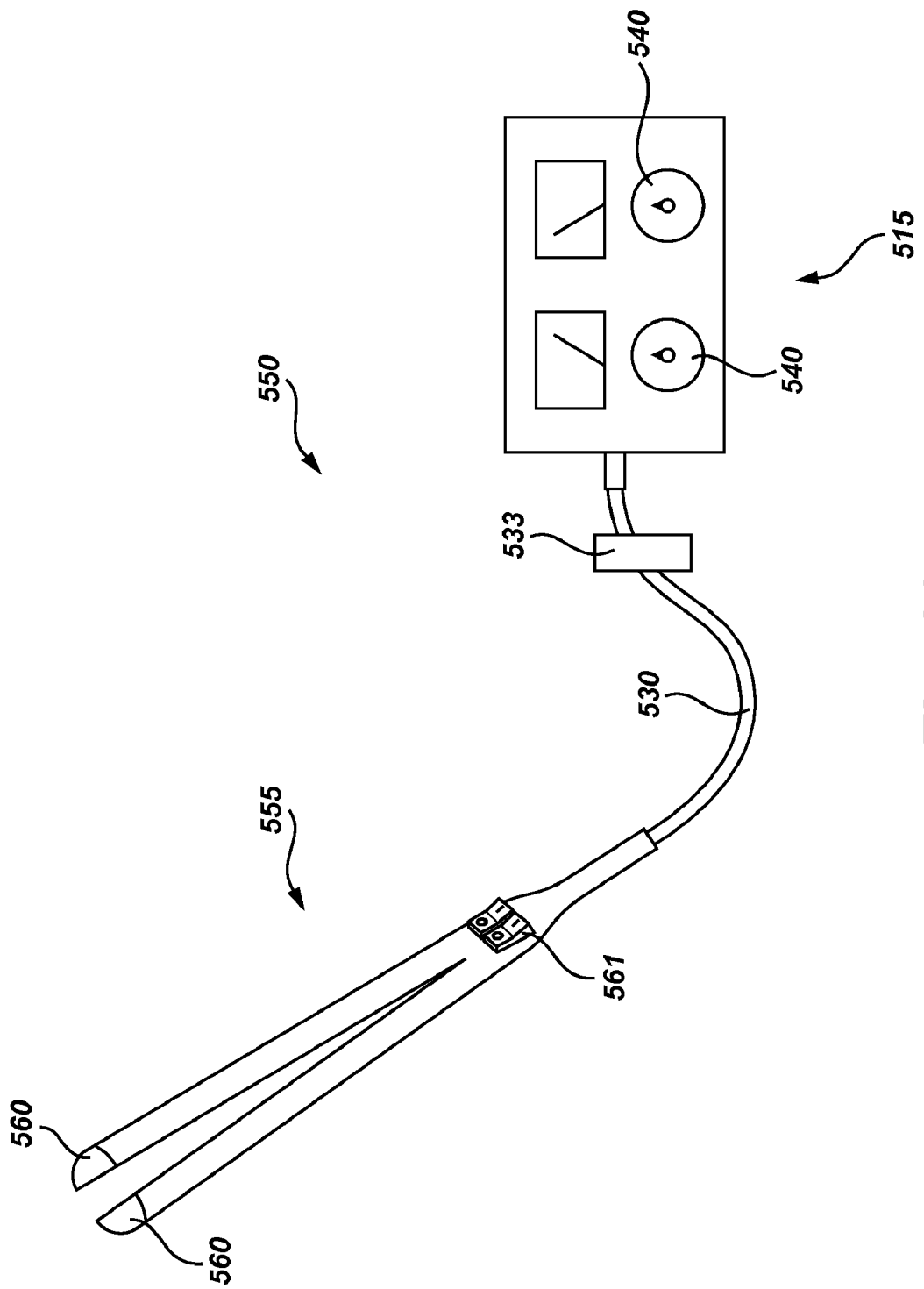
FIG. 29 shows a multi-mode surgical tool with bipolar and thermal modalities.

Turning now to FIG. 29, a multi-mode surgical tool 550 with bipolar and thermal modalities is shown. The power supply 515 may supply bipolar and thermal signals through a cable 530 to multi-mode forceps 555. The bipolar signal may be transferred through a first forceps tip 560 through tissue into a second forceps tip 560 using a bipolar waveform. The thermal signal may be converted into thermal energy by heating elements within one or more of the forceps tips 560.

The multi-mode forceps combine thermal heating and bipolar electrosurgery modalities into a multi-mode forceps tip 560. The forceps tip 560 may allow for cutting using an electrosurgical element, and sealing with the thermal portion to thereby provide improved cutting and sealing of the tissue. The surgical tool may also allow for other tissue effects to be applied to tissue either by both modalities in tandem or as needed. In other words, the electrosurgical modality and the thermal modality may be used at different times or may overlap. For example, a physician may contact tissue with the bipolar element to incise the tissue until he or she encounters undesired bleeding, at which time he or she can dispose the thermal element adjacent the bleeding tissue and activate the thermal modality for hemostasis. This can be done after stopping the bipolar modality, or while the bipolar modality is still being used (e.g. closely following the bipolar modality as the physician incises tissue. Controls 540 can be provided to prevent both being used simultaneously or overlapping, or the user can control when each modality is used.

Similarly, the surgical tool may also use both modalities to apply similar tissue effects or different tissue effects. A control such as a handpiece control 561 may be provided to allow the physician to selectively use the bipolar modality, the thermal modality or both.

As in the monopolar multiplexed environment, the bipolar signal may be prevented from using the electrical return path of the thermal element by a filter 533. Instead, the electrosurgical signal may be directed through tissue to access the return path.

Figure 30:
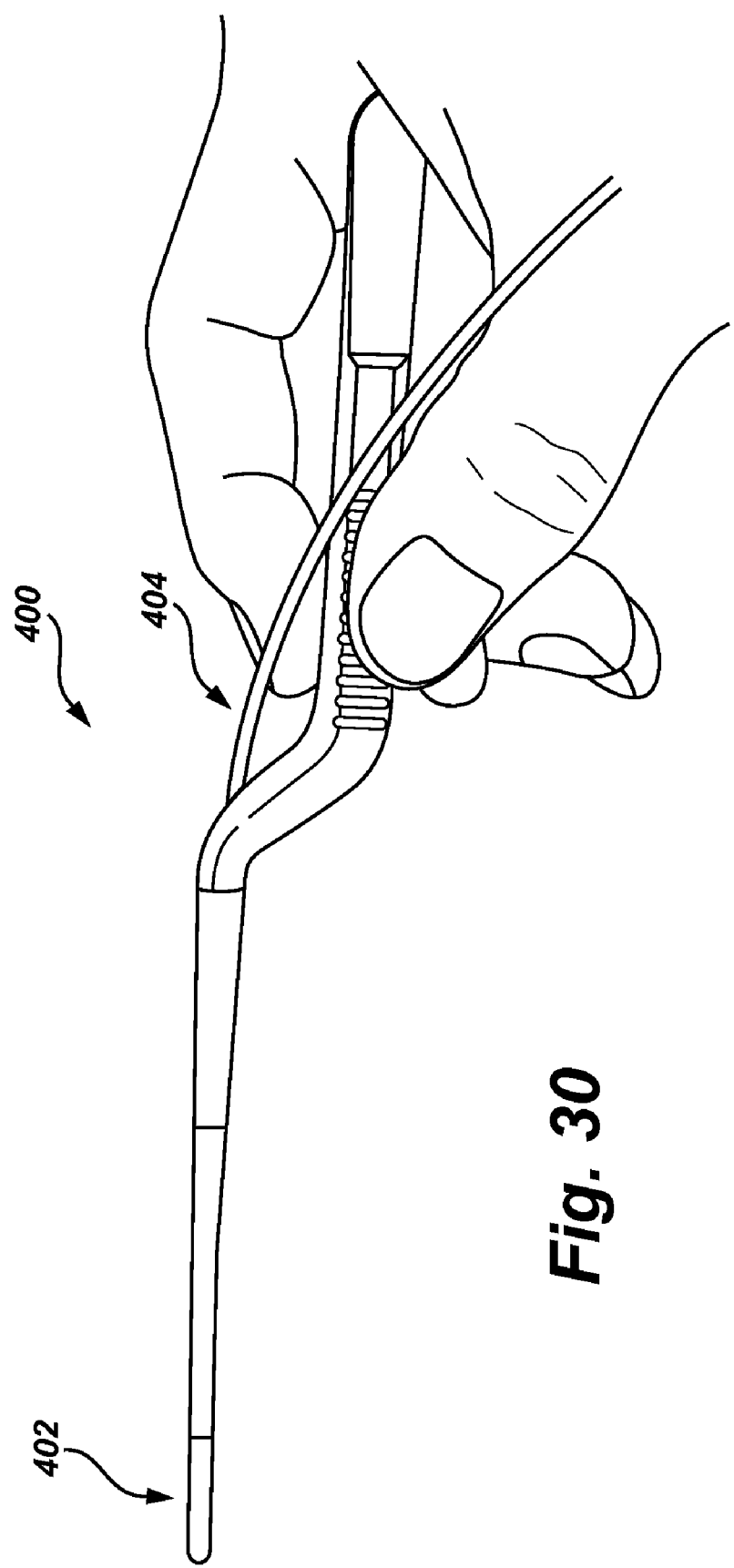
FIG. 30 shows a side view of multi-mode forceps.

Turning now to FIG. 30, a side view of a multi-mode forceps 400 is shown. In one embodiment, a nickel-iron alloy is used for ferromagnetic inductive heating and electrosurgery modalities. The nickel-iron alloy passes low temperature cutting current waveforms into the tissue itself, while absorbing high frequency energy for inductive heating. Low temperature cutting current may have very little hemostatic property, but is also minimally injurious. Thus, low temperature cutting current is a desirable cutting modality. To remedy the lack of hemostatic property, contact thermal sealing by the ferromagnetic coating avoids the deep contact desiccation and disruption effect of coagulation or fulguration waveforms as may be used in electrosurgery. Thus, the addition of a ferromagnetic sealing element provides improved cutting and sealing.

Various adaptations to the multi-mode forceps may be used to achieve desired effects. The combined instrument may multiplex RF frequencies or use separate current pathways 404 to optimize both thermal and electrosurgical modalities. Various tip geometries may be developed for such a hybrid instrument, including coapting bipolar forceps clad at the tips with thin magnetic film. The tip may have a coating 402 or partial coating to aid in conduction of the signal or reducing the amount of coagulum buildup. The RF energy transfer may also be enhanced through the addition of conductive material during surgery, such as the addition of saline solution.

Figure 31A:
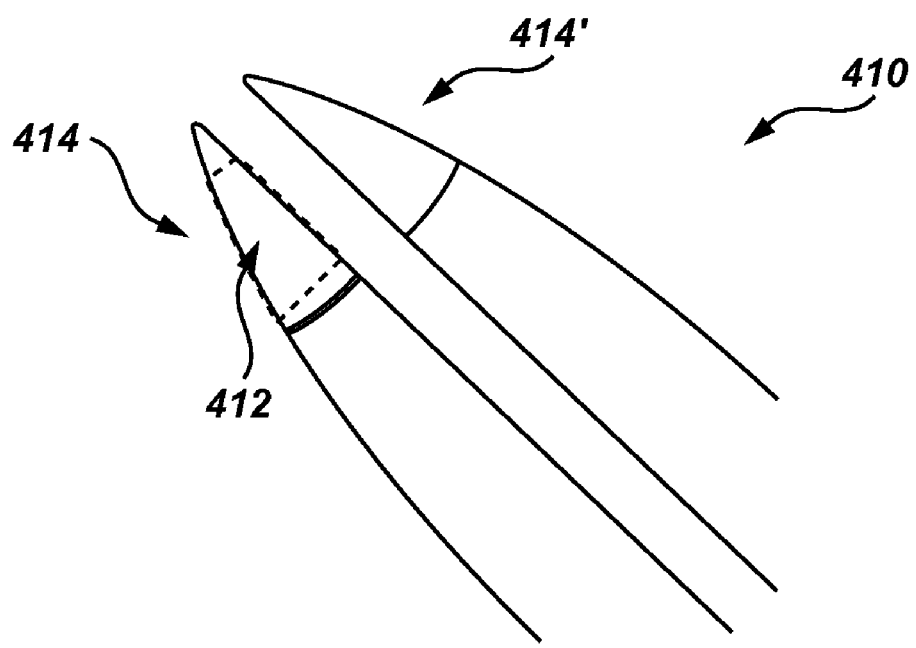
FIG. 31A shows a close up of an alternate embodiment of forceps tips.

Turning now to FIG. 31A, close up of an alternate embodiment of forceps tips 410 is shown. In one embodiment, hemostatic forceps incorporate a ferromagnetic heat source 412 on a first forceps tine 414 and a thermal sensor in an opposite tine 414'. The feedback of the thermal sensor may be reported such that an optimal tissue effect is reached and maintained. The temperature may thus be regulated and power delivery adjusted to provide the desired effect.

Adding a bipolar modality to the forceps tips 410 may improve the singular thermal modality. The sensor may continue to report temperature at the tines 414 or 414', but its output may be used to make decisions on adjustments to both modalities.

Similar to the monopolar-thermal hybrid device, a bipolar-thermal device may contain bipolar electrodes and a thermal element. The bipolar modality and thermal modality may be used together or independently, as needed. Thus, the surgeon may select from the benefits of multiple modalities. For example, to avoid deep tissue effects, the surgeon may avoid blended bipolar waveforms related to hemostasis, but instead use the integrated thermal modality of the forceps for hemostasis. In another embodiment, the surgeon may use the thermal modality for incising soft tissue, but may select to add the bipolar modality with a cutting waveform when more resistant tissue is reached.

A sensor may be placed within a multi-mode device to detect temperature or tissue effects. The information from the sensor may then be used to adjust the output of the multi-mode device. In one embodiment, the sensor may detect tissue charring. The generator may then be notified to scale back the power delivered to the bipolar or thermal system that may have caused the charring.

Figure 31B:
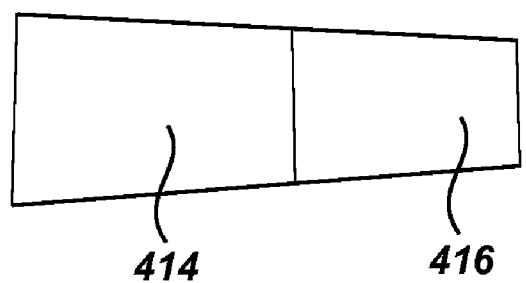
FIG. 31B shows a diagram of a coated forceps tip.

Turning now to FIG. 31B, a diagram of a coated forceps tine 414 is shown. In one embodiment a non-stick covering 416 over the ferromagnetic coating, such as Teflon, may markedly decrease coagulum build-up and the necessity for instrument cleaning. However haphazard application of the coating may also impede the dynamics of rapid temperature acquisition and rapid decay due to its thermal conduction properties. By selecting the coating material by important characteristics, including thermal mass and thickness, desired temperature retention characteristics may be achieved. Furthermore, a non-conductive coating may only be partial, thus reducing the electrosurgical resistance, but keeping the benefit of a non-conductive coating like Teflon.

The bipolar multi-mode surgical tool may also be disposed upon a catheter. The catheter may be rigid or flexible. The catheter may also be configured for aspiration, irrigation, substance delivery, visual feedback, sensing with a sensor, or other applications.

A method of treating tissue may include the steps of: selecting a surgical tool with electrosurgical and thermal modalities; disposing a tip in contact with tissue; and activating at least one of the modalities.

The method may optionally include the steps of: selecting a desired temperature range; selecting a bipolar modality; selecting a power setting corresponding to a desired tissue effect; selecting a thermal modality with a ferromagnetic coated conductor; activating a first modality for incising; activating a second modality for at least one of vascular endothelial welding and hemostasis; activating the modalities such that the modalities active period overlaps; or comprises activating the modalities such that the modalities active period is prevented from overlapping.

A method of incising tissue may include the steps of: selecting a surgical tool with bipolar and inductive heating modalities; activating the bipolar modality for incising; disposing the tip adjacent contact with tissue; and activating the inductive heating modality for at least one of vascular endothelial welding and hemostasis.

The method may optionally include the steps of: comprises maintaining the bipolar modality active while activating the heating modality to thereby incise tissue and create hemostasis at substantially the same time; or using a surgical instrument having a pair of arms with a bipolar electrode and a thermal element on the same arm.

Figure 32A:
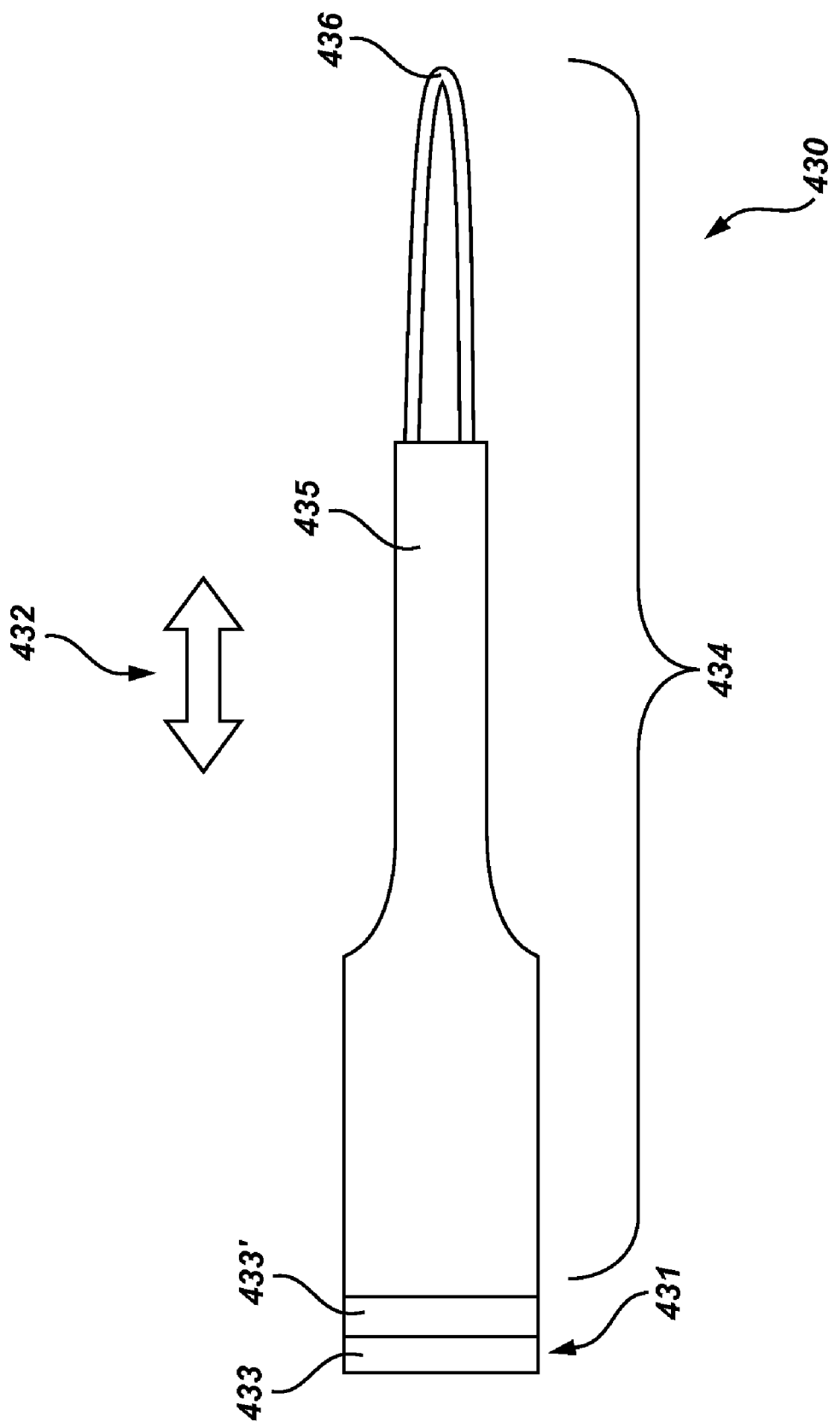
FIG. 32A shows a multi-mode surgical tool with thermal and ultrasonic modalities.

Turning now to FIG. 32A, a multi-mode surgical tool 430 with thermal and ultrasonic modalities is shown. Power is provided to an ultrasonic transducer 431 (which drives a load) to create ultrasonic motion, as shown by arrows 432, of a body 434 that may include an ultrasonic horn 435. During operation, the body 434 may disrupt tissue with the ultrasonic energy, i.e. can incise or help break up undesired tissue. Alternatively, the ferromagnetic coated conductor can be actuated by low frequency mechanical vibrational energy.

As the tissue is disrupted by ultrasonic (or vibrational) energy, a thermal element, such as a coated ferromagnetic wire or ferromagnetic coated conductor 436, at the tip of the body 434 may be heated to achieve a desired thermal effect, such as hemostasis. (The ferromagnetic coating acts as a load for a waveform as discussed above).

While the above diagram is shown to operate linearly, other geometrical motions may be used. For example, in one embodiment, the body oscillates in a circular motion. The rotation may be centered around the axis shown by arrows 432. In another embodiment, the body may oscillate in both the axis direction of arrows 432 and circularly around the axis shown by arrows 432.

In use, a power source provides inductive heating signals, i.e. waveforms as discussed above, to the conductor 436 to provide a thermal modality. At the same time and/or independently, a ultrasonic signal, i.e. a signal which drives an ultrasonic transducer 433 or stack of ultrasonic transducers (433 and 433'), such as piezoelectric transducers, are provided to move the body to create ultrasonic movement. Thus, the body 434 can provide ultrasonic treatment before, during or after thermal treatment is being applied.

The tool may be used for incising, hemostasis, vascular endothelial welding, tissue ablation or a combination thereof. In one embodiment, the ultrasonic modality may be used to incise, while the thermal modality may be used for hemostasis. In another embodiment, the ultrasonic modality is used to insert a tip into tissue and the thermal modality is used for tissue ablation.

Figure 32B:
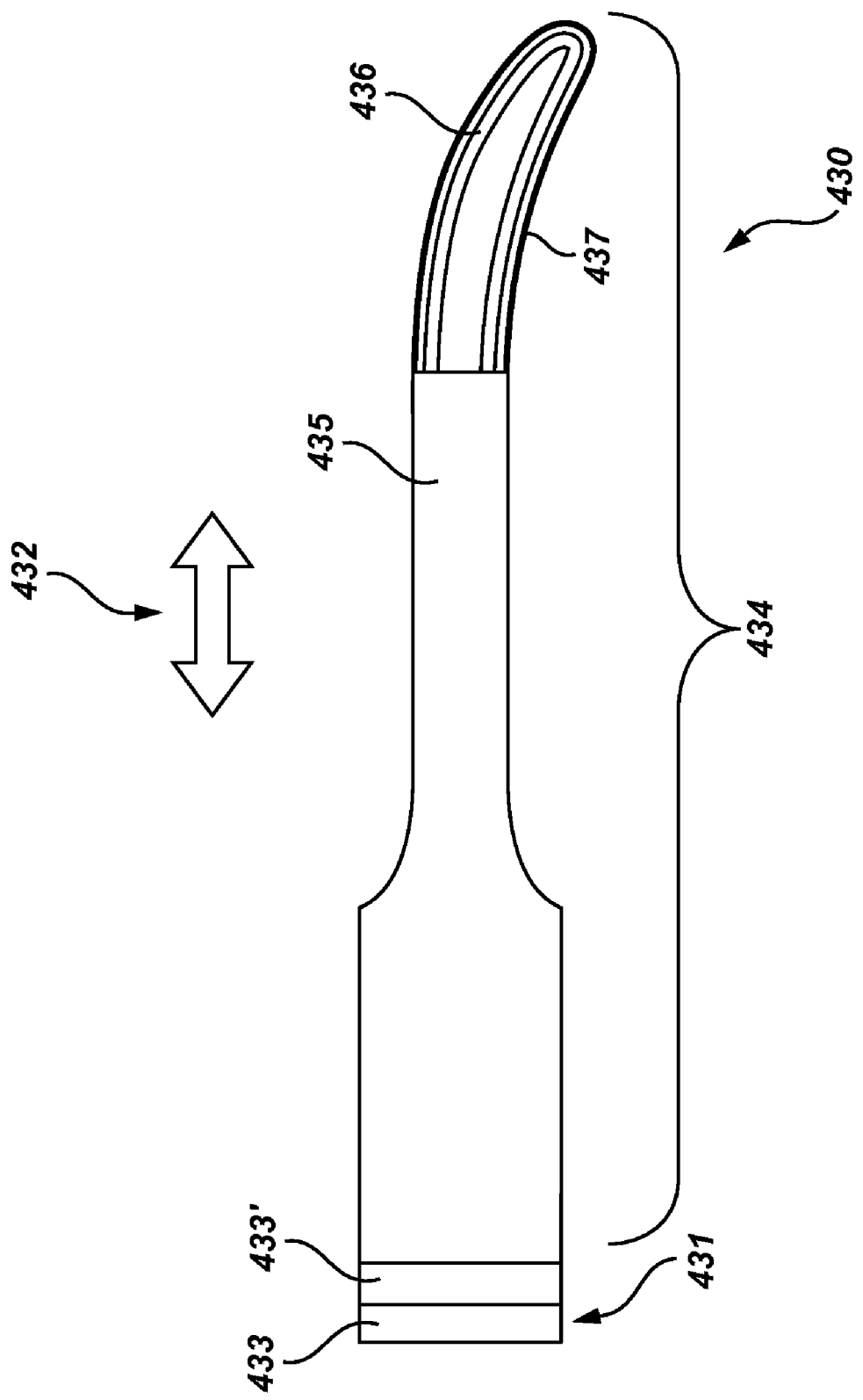
FIG. 32B shows a multi-mode surgical tool with thermal and ultrasonic modalities with a hook primary geometry.

Turning now to FIG. 32B, an multi-mode surgical tool with thermal and ultrasonic modalities and a hook primary geometry 437 is shown. The multi-mode tool 430 may also include a primary geometry to which a thermal element may be attached. Similarly, the thermal element may be configured for various tissue effects.

Figure 32C:
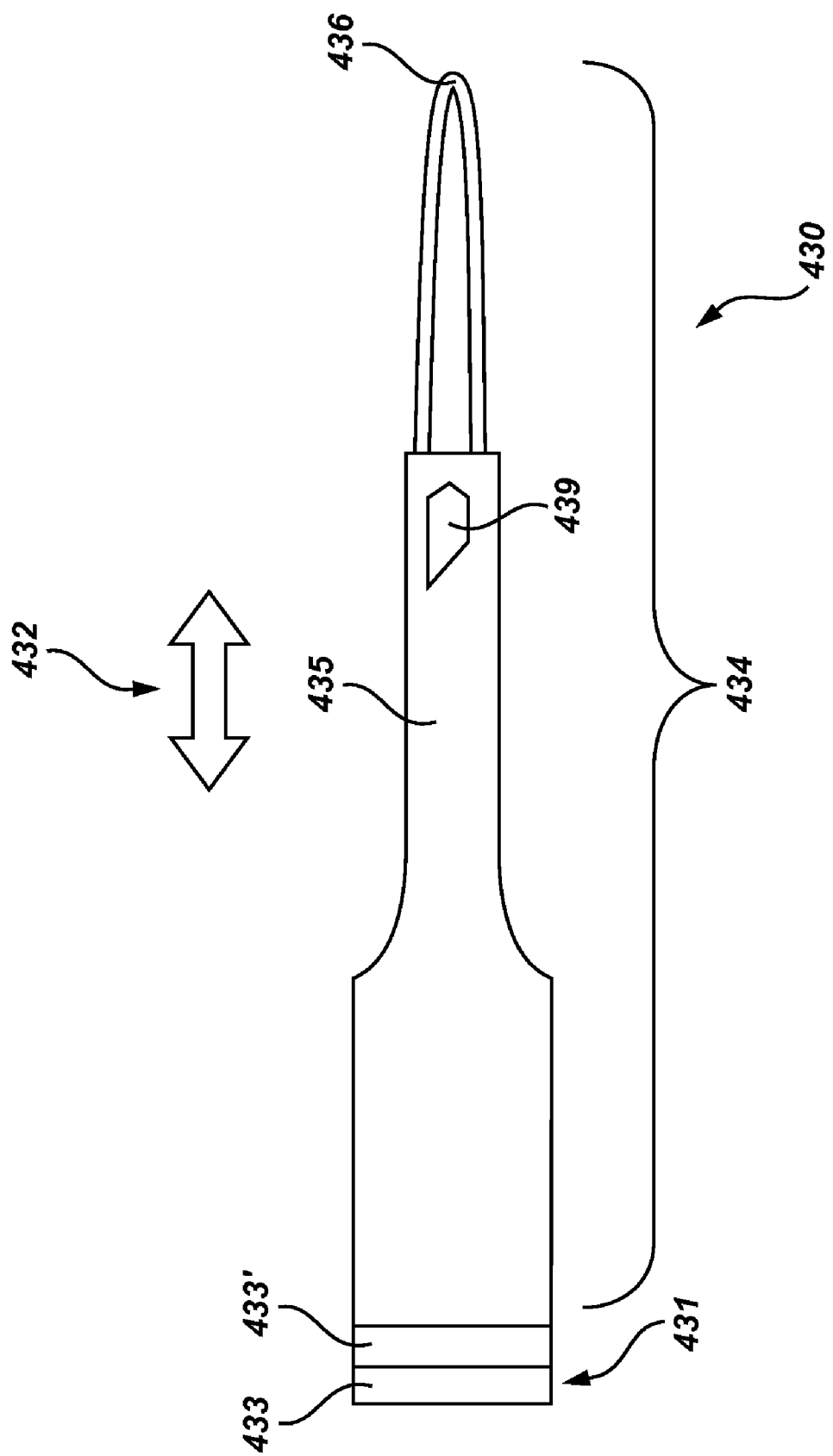
FIG. 32C shows a multi-mode surgical tool with thermal and ultrasonic modalities with a sensor.

Turning now to FIG. 32C, a sensor 439 has been added to FIG. 32A. The sensor may detect tissue effects or even the temperature of the device, similar to other sensors already discussed. Similarly, the sensor may be used as a feedback mechanism in the control of the available modalities, including the power delivery.

Figure 32D:
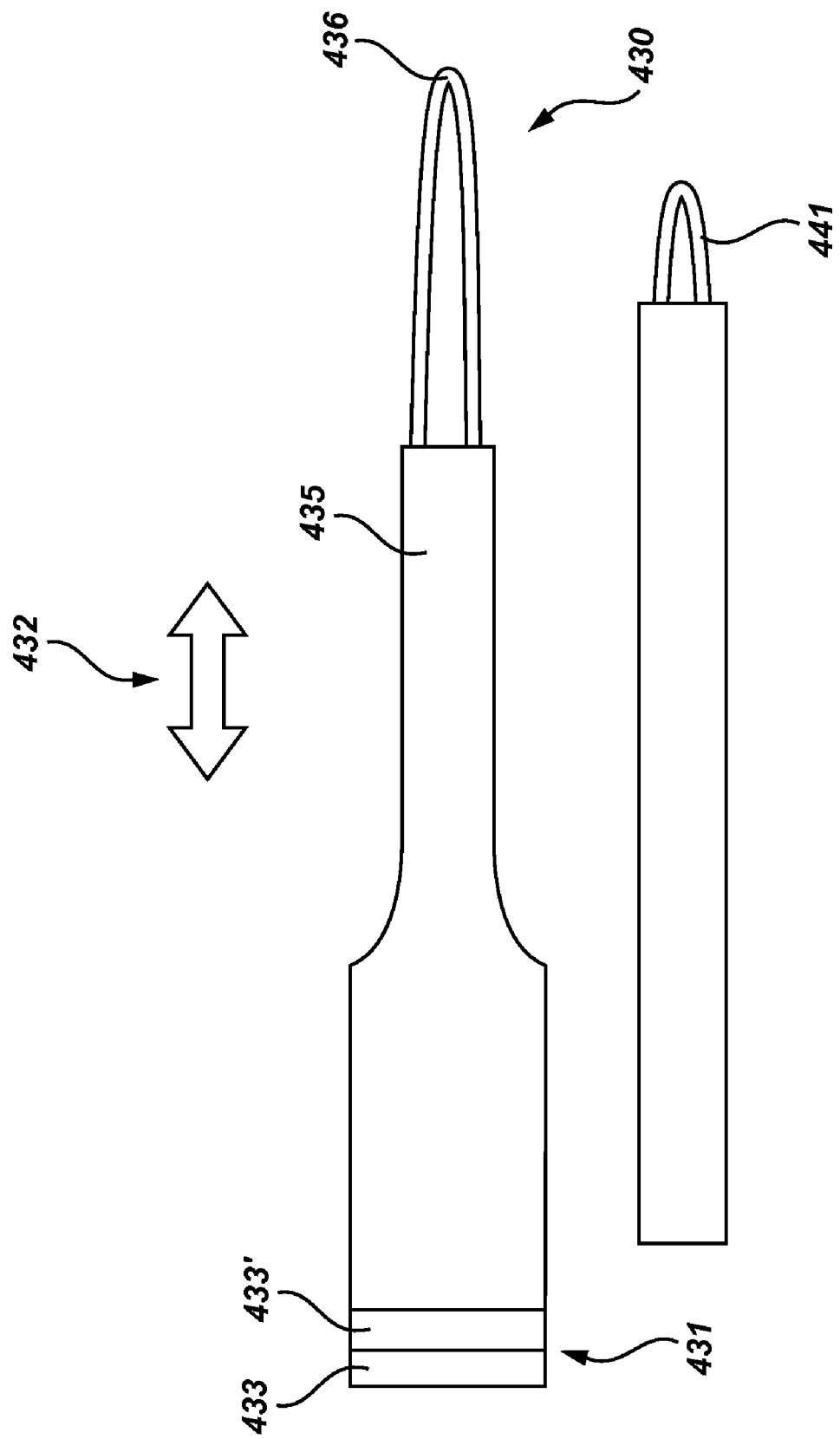
FIG. 32D shows a multi-mode surgical tool with thermal and ultrasonic modalities with a second tip.

Turning now to FIG. 32D, a second tip 441 may be placed in proximity to the first tip 436. The second tip may also contain one or more sensors or another modality, including a multi-mode tip.

Figure 33:
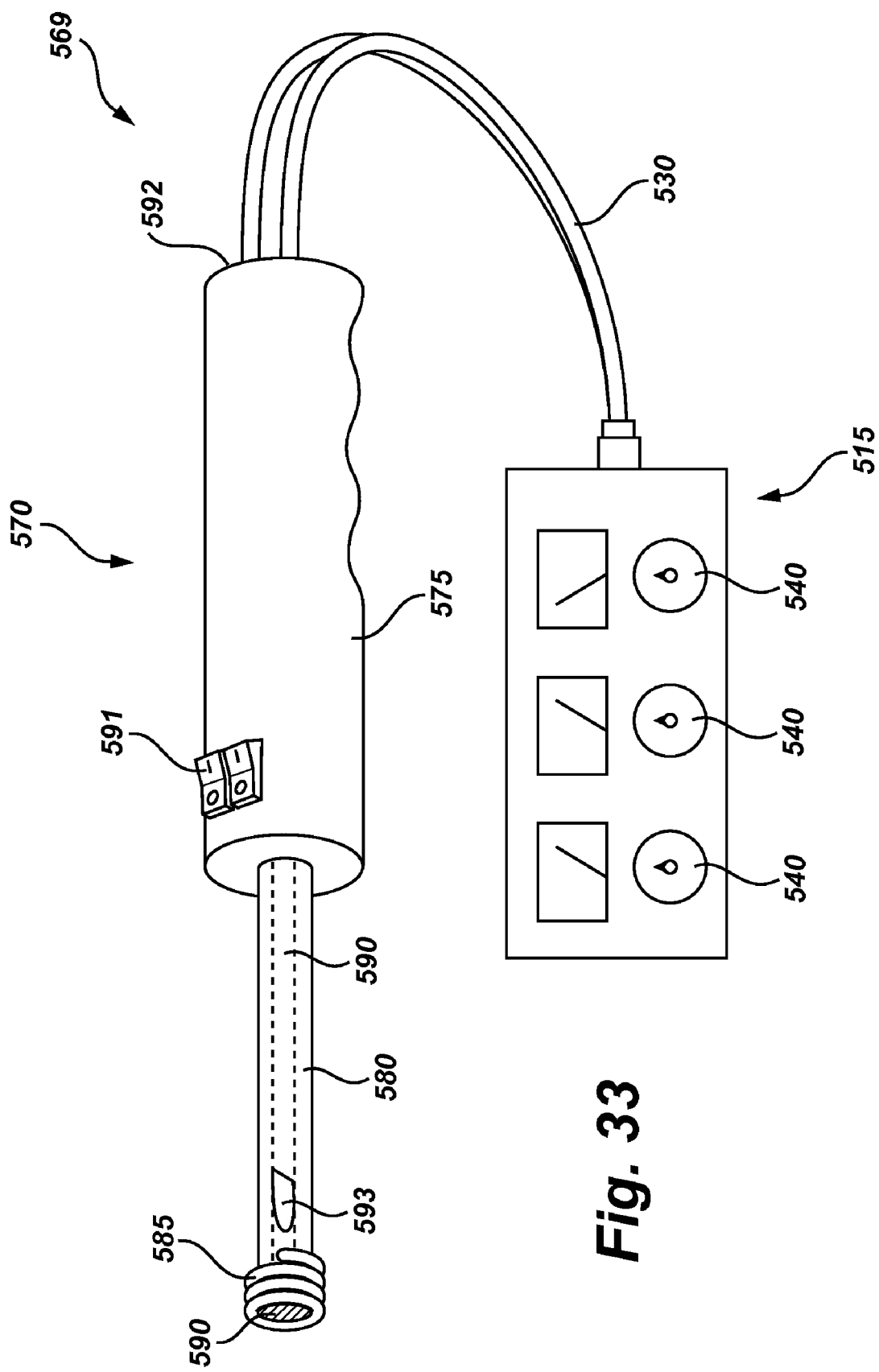
FIG. 33 shows a multi-mode surgical tool with thermal and ultrasonic modalities with aspiration/irrigation and sensor.

Turning now to FIG. 33, a multi-mode surgical tool 569 with thermal and ultrasonic modalities and aspiration/irrigation is shown. The tool 569 includes a power supply 515 with a plurality of controls 540 that may be individually addressable for providing energy and controlling a pump (if desired) for irrigation or aspiration, to a handpiece 570 via a cable 530. The handpiece 570 includes an oscillating body 580 and a thermal element 585.

The power supply 515 may provide ultrasonic and thermal signals to drive respective loads (i.e. the body 580 and the thermal element 585). (A similar power supply could be used with the embodiment shown in FIG. 32). The power supply 515 may provide individual or multiplexed signals to the handpiece 570. Each signal may be individually controlled by controls 540, buttons 591 or in some cases, jointly controlled by activation of the handpiece. In fact, the suction may also be controlled in the same manner—individually or jointly.

In addition to signals to create ultrasonic and thermal energy, the power supply 515 may be configured to provide suction, for example, through a lumen or aspirating bore 590, through the grip 575 of the handpiece 570 and through a tube/cable 530 to a reservoir. In the embodiment shown in FIG. 33, the reservoir may be contained in the power supply 515.

The handpiece 570 may contain a grip 575, body 580 (which forms a lumen, bore or catheter) and surgical tip 585. In one embodiment, the grip 575 contains an actuator or control 591 that causes ultrasonic vibration of tip of the body or catheter 580. The tip of the catheter 580 may include a heating element, such as a ferromagnetic coated conductor 585. As the ultrasonic or thermal energy is applied to the tissue, the catheter bore 590 may aspirate any disrupted tissue, including fat, or associated effects.

In one embodiment, the multi-mode surgical tool 569 may provide a delivery or irrigation mechanism. In one embodiment, a substance may be placed in the catheter lumen 590. The ultrasonic mode may be used to disrupt enough tissue to arrive at a targeted delivery site for the substance to be deposited. At the targeted location, the thermal element of the multi-mode surgical tool 569 may be activated such that the substance may melt and be deposited at the delivery site. If needed, the thermal element may be used for hemostasis or tissue welding during the insertion or removal of the tool.

Similarly, the tool 569 may be used for delivery of other substances through the catheter. While much of the discussion above centers on aspiration, the tool may be used to deliver substances through the catheter. For instance, the tool 569 may be used to deliver saline solution, medication, etc., including in a heated state if desired.

In one embodiment, the catheter may have a plurality of bores. One bore may be configured to aspirate, while another bore may be configured to irrigate.

Like the other embodiments discussed above, variety of sensors 593 may be used. They could be disposed in the body 580 or could be inserted through the lumen 590. This could be accomplished via a port 592. It will be appreciated that the sensors could be temperature sensors, sensors which monitor tissue condition, devices for visualization, i.e. cameras, CCD sensors or fiber-optic wires, etc. Additionally, the power source 515 could be made to react to the sensor, such as, for example, adjusting to keep heat in the thermal element 585 in a desired range for the desired effect in the tissue, i.e. hemostasis, vascular welding, searing, incision or ablation.

A process of delivering power to a thermally adjustable multi-mode surgical tool may include the steps of: delivering a first oscillating signal to a conductor configured such that the first oscillating electrical signal forming an approximate standing wave with maximum current and minimum voltage substantially at a first load comprising a portion of the conductor coated by ferromagnetic material; and delivering a second oscillating signal to a second electrical connection configured such that a second oscillating electrical signal will drive an ultrasonic transducer to thereby move a second load ultrasonically.

The process may include the optional steps of: placing the first load adjacent tissue and wherein first oscillating electrical signal heats a thermal element to a temperature causing hemostasis in the tissue and the second oscillating electrical signal causes the second load to incise tissue; applying suction adjacent the first load and second load to aspirate incised tissue; or multiplexing the first oscillating signal and the second oscillating signal in a communications channel to the first load and second load.

A method for incising and sealing tissue may include the steps of: selecting a surgical tool having a conductor with a ferromagnetic coating disposed on a portion thereof and an transducer which drives a body; disposing the body and ferromagnetic coating into contact with the tissue; delivering an oscillating electrical signal to the transducer so as incise the tissue; and delivering an oscillating electrical signal to the conductor so as to heat the ferromagnetic coating and apply heat to the tissue.

The method may also include the optional steps of: heating the ferromagnetic coating to promote tissue hemostasis or selecting a ultrasonic transducer.

A method for tissue ablation may include the steps of: selecting a tip with ultrasonic and thermal modalities; inserting the tip into the undesired tissue; and activating one or more of the modalities within the undesired tissue.

The method may include the optional steps of: selecting a ferromagnetic coating as the thermal modality and aspirating residue from an area proximate to the undesired tissue.

It will be appreciated that the various waveforms discussed for the thermal element may be used with each of the embodiments discussed herein. Additionally, it will be appreciated that aspects such sensors and control responsive to sensors may be applied to each of the embodiments and are therefore not repeated in detail with respect to each. Likewise, aspects of the thermal element, such as the use of a non-stick coating, and formation of the thermal element may be used across embodiments if desired.

Several advantages may be noted in use of embodiments of the present invention. In one embodiment, optimal thermal hemostatic effect in association with tissue ultrasound disruption and suction can be achieved for tumor debulkment as applied in solid organs, like the brain. Alternatively, laparoscopic vascular dissection and detachment can be more optimally achieved compared to ultrasonic effects alone.

While a catheter has been discussed only with respect to the ultrasonic modality, it should be noted that the catheter embodiment may be applied to any of the multi-mode energy modalities and achieve each of the benefits provided by the aspiration, sensors, etc. Similarly many of the benefits of the ultrasonic and thermal multi-mode catheter embodiment may be achieved with the other multi-mode embodiments. Those skilled in the art will appreciate modifications to such embodiments to provide these multiple modalities of treatment.

Figure 34:
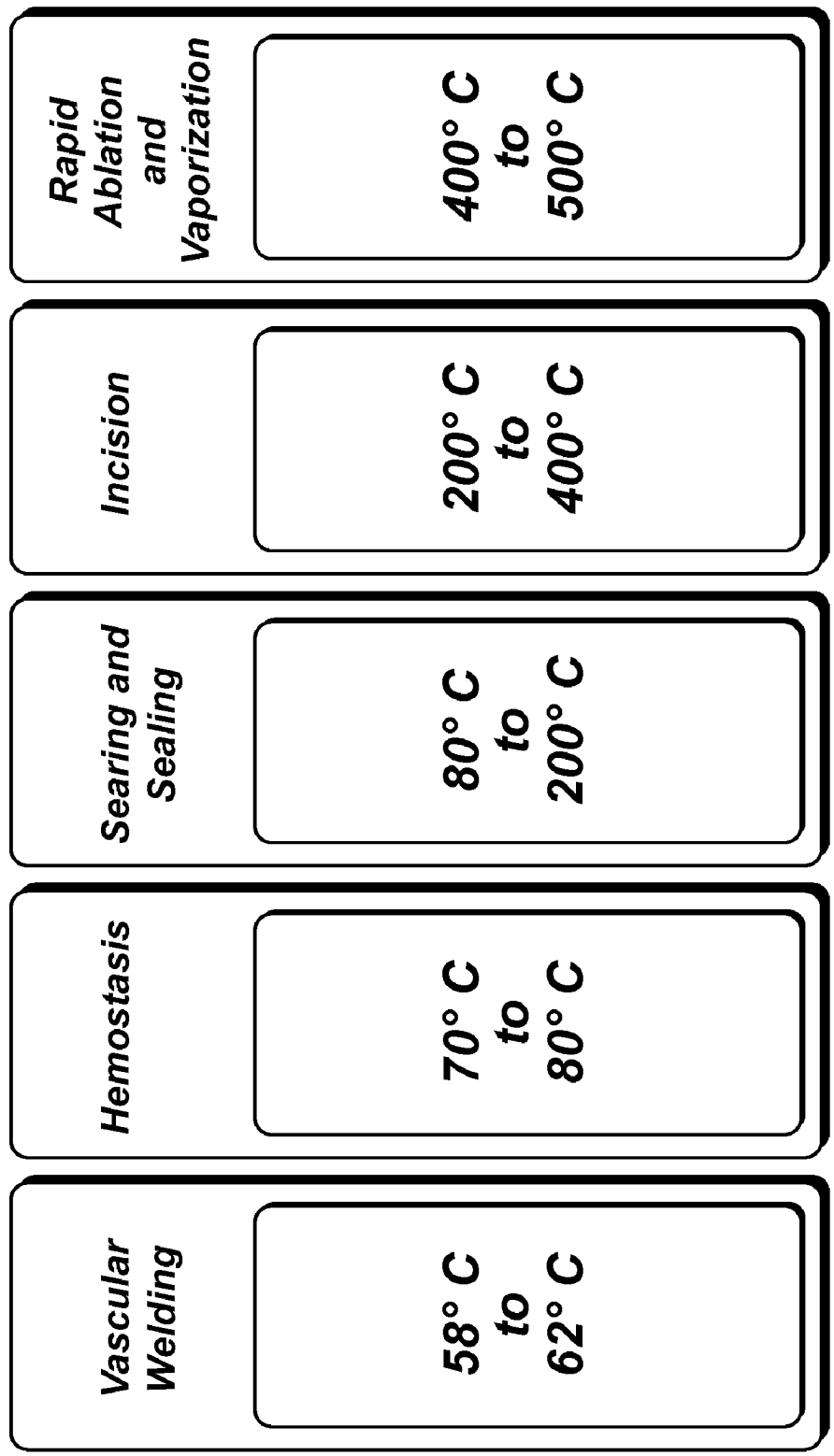
FIG. 34 shows a thermal spectrum as related to tissue effects.

Turning now to FIG. 34, a temperature spectrum is disclosed. Tissue may react differently at different temperatures and thus temperature ranges will result in different treatments for tissue. Specific tissue treatments are somewhat variable due to inconsistencies including tissue type and patient differences. The following temperatures have been found to be useful. Vascular endothelial welding may be optimal at 58-62 degrees Centigrade. Tissue hemostasis without sticking may be optimally achieved at 70-80 degrees Centigrade. At higher temperatures, tissue searing and sealing may occur more quickly, but coagulum may build-up on the instrument. Tissue incision may be achieved at 200 degrees Centigrade with some drag due to vaporization at the edges. Tissue ablation and vaporization may occur rapidly in the 400-500 degree Centigrade range. Thus, by controlling the temperature the "treatment" of tissue which the device delivers can be controlled, be it vascular endothelial welding, tissue incision, hemostasis or tissue ablation.

According to the spectrum disclosed above, power delivery settings corresponding to the desired temperature range may be included in the power delivery switch. In one embodiment, the foot pedal may have several stops that indicate to the surgeon the likely tip temperature range of the current setting.

It will be appreciated that the thermal surgical tool system in accordance with the present invention will have a wide variety of uses. Not only can it be used on humans, it can also be use to cut tissue of other animals, such as in the context of a veterinarian or simply cutting tissues or biomaterials, such as those used for implantation, into smaller pieces for other uses.

Certain embodiments of the surgical system may have broad application within surgery as well. A loop geometry may have advantages in cutting, coagulation and biopsy applications. A blade geometry may have advantages for cutting and hemostasis applications. The point geometry may have advantages in dissection and coagulation applications, and in particular, neurodissection and coagulation. However, the application of a geometry may be further configured and tailored to an application by diameter, length, material characteristics and other characteristics discussed above.

While the present invention has been described principally in the area of surgical tools and the treatment of live tissue (though it can be used on dead tissue as well), it will be understood that a tool made in accordance with the present invention and the methods discussed herein may have other uses. For example, a cutting tool could be formed for butchering meat. Whether the meat is fresh or frozen, the tool can be useful. For example, a cutting blade which is heated to a high temperature will cut through frozen meat. However, when power is no longer supplied, the "cutting" edge is safe to the touch. Likewise, cutting meat with a hemostasis setting would slightly sear the exterior of the meat, locking in juices. Other uses of the instruments discussed herein will be understood by those skill in the art in light of the present description.

There is thus disclosed an improved multi-mode thermally adjustable surgical tool. It will be appreciated that numerous changes may be made to the present invention without departing from the scope of the claims.

What is claimed is:

1. A multi-mode surgical tool comprising:
an electrosurgical electrode for treating tissue by passing electrical energy through the tissue; and a thermal surgical element for generating heat and conducting said heat from the thermal element to tissue to thereby treat the tissue, the thermal surgical element comprising:
an elongate conductor for receiving electrical energy; and
a ferromagnetic coating disposed circumferentially about the elongate conductor;
wherein delivering electrical energy to the elongate conductor causes the ferromagnetic coating to heat to a temperature of between about 40 degrees Centigrade and below a Curie temperature of the thermal surgical element;
wherein the elongate conductor of the thermal surgical element is also the electrosurgical electrode; and
wherein the ferromagnetic coating, when heated, is movable between air and liquid without causing fracturing of the ferromagnetic coating.

2. The multi-mode surgical tool of claim 1, wherein the electrosurgical electrode is a monopolar electrode.

3. The multi-mode surgical tool of claim 1, further comprising a handle, wherein a section of the elongate conductor extends to and from the handle, and wherein the ferromagnetic coating covers less than all of the section of the elongate conductor extending from the handle.

4. The multi-mode surgical tool of claim 1, wherein the electrosurgical electrode is configured to operate as a monopolar electrode and wherein the elongate conductor is a wire.

5. The multi-mode surgical tool of claim 1, further comprising a single conductive pathway for delivering a multiplexed signal to both the electrosurgical electrode and the thermal surgical element.

6. The multi-mode surgical tool of claim 5, wherein the tool further comprises a signal generator for generating a multiplexed signal.

7. The multi-mode surgical tool of claim 5, wherein the multiplexed signal further comprises a monopolar signal.

8. The multi-mode surgical tool of claim 7, wherein the monopolar signal is between 200 kHz and 2 MHz.

9. The multi-mode surgical tool of claim 8, wherein the monopolar signal is between 350 kHz and 800 kHz.

10. The multi-mode surgical tool of claim 7, wherein the multiplexed signal further comprises an inductive heating signal.

11. The multi-mode surgical tool of claim 10, wherein the inductive heating signal is between 5 MHz and 24 GHz.

12. The multi-mode surgical tool of claim 11, wherein the inductive heating signal is between 40 MHz and 928 MHz.

13. The multi-mode surgical tool of claim 3, further comprising a catheter, wherein the electrosurgical electrode and the thermal surgical element are disposed upon the catheter.

14. The multi-mode surgical tool of claim 13, wherein the catheter is rigid.

15. The multi-mode surgical tool of claim 13, wherein the catheter is flexible.

16. The multi-mode surgical tool of claim 13, wherein the catheter is configured for aspiration.

17. The multi-mode surgical tool of claim 13, wherein the catheter is configured for substance delivery.

18. The multi-mode surgical tool of claim 13, wherein the catheter further comprises at least one sensor.

19. The multi-mode surgical tool of claim 13, wherein the catheter further comprises means for generating visual feedback.

20. A multi-mode surgical tool comprising:
a tip comprising an electrical conductor forming a physically continuous conductive pathway having an exposed portion that extends to and from the tip;
a ferromagnetic coating covering a first part of the exposed portion of the electrical conductor, the ferromagnetic coating being selected from ferromagnetic coatings which will convert some frequencies of oscillating electrical energy into thermal energy thereby causing the ferromagnetic coating to heat and will pass other frequencies of oscillating electrical energy into tissue;
wherein the heated ferromagnetic coating is moveable between a first environment and a second environment without causing the ferromagnetic coating to fracture even when the first environment and the second environment have a large temperature differential.

21. The multi-mode surgical tool of claim 20, further comprising a signal generator for sending a multiplexed signal into the electrical conductor.

22. The multi-mode surgical tool of claim 20, wherein the electrical conductor further comprises an electrosurgical electrode.

23. The multi-mode surgical tool of claim 22, wherein the electrosurgical electrode is a monopolar electrode.

24. The multi-mode surgical tool of claim 20, wherein the ferromagnetic coating is configured to simultaneously disperse thermal energy and oscillating electrical energy into tissue.

25. A thermally adjustable multi-mode surgical tip comprising:
a cable;
a small diameter electrical conductor having a proximal and distal end, wherein the proximal end is configured to receive radiofrequency energy from the cable;
a thin plating of ferromagnetic material disposed circumferentially about the small diameter electrical conductor, wherein the thin plating of ferromagnetic material is configured with a Curie point sufficiently high to encompass a desired set of therapeutic temperature ranges;
wherein the small diameter electrical conductor further comprises an electrosurgical element configured to receive power from the cable and configured to release radiofrequency energy into nearby tissue; and
wherein the thin plating of ferromagnetic material, when heated, is movable between air and liquid without causing the thin plating of ferromagnetic material to crack.

26. The multi-mode surgical tool of claim 25, wherein the electrosurgical element is a monopolar element.

27. The multimode surgical instrument of claim 1, wherein the thermal surgical element is configured to reach a sufficient temperature for self-cleaning when a power source is applied thereto.

28. The multi-mode surgical tool of claim 1, further comprising a power source configured to deliver an oscillating current to the thermal surgical element.

29. The multi-mode surgical tool of claim 28, further comprising a sensor disposed adjacent the thermal surgical element.

30. The multi-mode surgical tool of claim 29, wherein the power source is configured to react to the sensor.

31. The multi-mode surgical tool of claim 29, wherein the sensor is configured to measure tissue properties.

32. The multi-mode surgical tool of claim 29, wherein the sensor is configured to allow visual observation of tissue.

33. The multi-mode surgical tool of claim 28, wherein the power source is configured to measure a temperature indicator of the ferromagnetic coating and adjust an output to maintain a predetermined therapeutic temperature range in tissue.

34. The multi-mode surgical tool of claim 20, further comprising a temperature sensor disposed adjacent the electrical conductor for measuring temperature.

35. The multi-mode surgical tool of claim 31, wherein the sensor is configured to measure transferred heat.

* * * * *